United States Patent [19]

Froehler et al.

[11] Patent Number: 5,830,653
[45] Date of Patent: Nov. 3, 1998

[54] METHODS OF USING OLIGOMERS CONTAINING MODIFIED PYRIMIDINES

[75] Inventors: Brian Froehler; Rick Wagner, both of Belmont; Mark Matteucci, Burlingame; Robert J. Jones, Millbrae; Arnold J. Gutierrez, San Jose; Jeff Pudlo, Burlingame, all of Calif.

[73] Assignee: Gilead Sciences, Inc., Foster City, Calif.

[21] Appl. No.: 473,481

[22] Filed: Jun. 7, 1995

Related U.S. Application Data

[60] Division of Ser. No. 976,103, Nov. 25, 1992, Pat. No. 5,645,985, which is a continuation-in-part of Ser. No. 965,941, Oct. 23, 1992, abandoned, which is a continuation-in-part of Ser. No. 935,444, Aug. 25, 1992, abandoned, which is a continuation-in-part of Ser. No. 799,824, Nov. 26, 1991, Pat. No. 5,484,908.

[51] Int. Cl.$^6$ .............................. C12Q 1/68; C12N 5/06; C12N 5/10; C07H 21/00
[52] U.S. Cl. .............................. 435/6; 435/325; 435/375; 514/44; 536/24.5
[58] Field of Search .............................. 435/6, 28, 69.1, 435/91.1, 172.3, 240.1, 240.2, 320.1, 325, 375; 514/44; 536/23.1, 23.2, 24.3, 24.5

[56] References Cited

U.S. PATENT DOCUMENTS

| | | | |
|---|---|---|---|
| 4,415,732 | 11/1983 | Caruthers et al. | 536/27 |
| 4,458,066 | 7/1984 | Caruthers et al. | 536/27 |
| 4,725,677 | 2/1988 | Köster | 536/27 |
| 4,959,463 | 9/1990 | Froehler et al. | 536/27 |
| 5,013,830 | 5/1991 | Ohtsuka et al. | 536/25.1 |
| 5,034,506 | 7/1991 | Summerton et al. | 528/391 |
| 5,204,455 | 4/1993 | Froehler et al. | 536/22.1 |
| 5,256,775 | 10/1993 | Froehler | 536/25.6 |
| 5,264,423 | 11/1993 | Cohen et al. | 514/44 |
| 5,264,564 | 11/1993 | Matteucci | 536/23.1 |
| 5,272,057 | 12/1993 | Smulson | 435/6 |
| 5,399,676 | 3/1995 | Froehler | 536/23.1 |
| 5,440,040 | 8/1995 | Gronowitz | 544/216 |
| 5,466,786 | 11/1995 | Buhr et al. | 536/26.26 |
| 5,495,009 | 2/1996 | Matteucci et al. | 536/25.3 |
| 5,596,086 | 1/1997 | Matteucci et al. | 536/22.1 |

FOREIGN PATENT DOCUMENTS

| | | |
|---|---|---|
| 1311201 | 12/1992 | Canada . |
| 0 486 477 A2 | 12/1987 | European Pat. Off. . |
| 0486477 A2 | 12/1987 | European Pat. Off. . |
| 0 251 786 A3 | 1/1988 | European Pat. Off. . |
| 0 269 574 | 6/1988 | European Pat. Off. . |
| 0 286 028 A2 | 10/1988 | European Pat. Off. . |
| 0 375 408 A1 | 6/1990 | European Pat. Off. . |
| 0 415 901 A2 | 3/1991 | European Pat. Off. . |
| 0 492 590 A1 | 12/1991 | European Pat. Off. . |
| WO 88/08001 | 10/1988 | WIPO . |
| WO 89/12060 | 12/1989 | WIPO . |
| WO 89/12061 | 12/1989 | WIPO . |
| WO 90/06934 | 6/1990 | WIPO . |
| WO 90/15884 | 12/1990 | WIPO . |
| WO 91/06626 | 5/1991 | WIPO . |
| WO 92/02258 | 2/1992 | WIPO . |
| WO 92 05186 | 4/1992 | WIPO . |
| WO 92/05186 | 4/1992 | WIPO . |
| WO 92/06102 | 4/1992 | WIPO . |
| WO 92/09705 | 6/1992 | WIPO . |
| WO 92/10590 | 6/1992 | WIPO . |

OTHER PUBLICATIONS

Graessmann et al. Inhibition of SV40 gene expression by microinjection of small antisnese RNA and DNA molecules. Nucleic acid Res. 19(1): 53–59,1990.

Booras et al. Evidence for positive and negative regulation in the promoter of the chicken d1–crystallin gene. Developmental Biol. 127(1):209–219.

Alderfer et al., "Comparative Studies on Homopolymers of Adenylic Acid Possessing Different C–2' Substituents of the Furanose. Poly(deoxyriboadenylic acid), Poly(riboadenylic acid), Poly(2'–0–methyladenylic acid), and Poly(2'–0–ethyladenylic acid)," Biochem 13(8):1615–1622 (1974).

Kielanowska et al., "Preparation and Properties of Poly'–O–Ethylcytidylic Acid," Nuc Acids Res 3(3):817–824 (Mar. 1976).

Ransford et al., "2–O–Ethyl Pyrimidine Nucleosides (1)," J Carbohydrates Nucls Nuclt 1(3):275–278 (1974).

Guathier–Rouviere et al., "Casein kinase II induces c–fos expression via the serum response element pathway and p67srf phosphorylation in living fibroblasts," Embo J 10(10):2921–2930 (1991).

Hollon et al., "Variation in Enzymatic Transient Gene Expression Assays," Anal Biochem 182:411–418 (1989).

Lamb et al., "Demonstration in Living Cells of an Intragenic Negative Regulatory Element within the Rodent c–fos Gene," Cell 61:485–496 (1990).

(List continued on next page.)

Primary Examiner—George C. Elliott
Assistant Examiner—Thomas G. Larson
Attorney, Agent, or Firm—Daryl D. Muenchau

[57] ABSTRACT

Novel oligomers are disclosed which have enhanced ability with respect to forming duplexes or triplexes compared with oligomers containing only conventional bases. The oligomers contain the bases 5-(1-propynyl)uracil, 5-(1-propynyl) cytosine or related analogs. The oligomers of the invention are capable of (i) forming triplexes with various target sequences such as virus or oncogene sequences by coupling into the major groove of a target DNA duplex at physiological pH or (ii) forming duplexes by binding to single-stranded DNA or to RNA encoded by target genes. The oligomers of the invention can be incorporated into pharmaceutically acceptable carriers and can be constructed to have any desired sequence, provided the sequence normally includes one or more bases that is replaced with the analogs of the invention. compositions of the invention can be used as pharmaceutical agents to treat various diseases such as those caused by viruses and can be used for diagnostic purposes in order to detect viruses or disease conditions.

15 Claims, 29 Drawing Sheets

OTHER PUBLICATIONS

Riabowol et al., "Microinjection of fos–Specific Antibodies Blocks DNA Synthesis in Fibroblast Cells.," Mol Cell Biol 8(4)1670–1676 (Apr. 1988).

Hobbs et al., "Palladium–Catlyzed Synthesis of Alkynylamino Nucleosides. A Universal Linker for Nucleic Acids," J Org Chem 54:3420–3422 (1989).

Kumar et al., "Synthesis and Antiviral Activity of Novel–5(1–Azido–2–haloethyl) and 5–(1–Azido–, amino–, or methoxyethyl) Analogs of 2'–Deoxyuridine," J Med Chem 36:2470–2474 (1993).

Leusink et al., "Studies in Group IV Organometallic Chemistry XXIV. Structure of Products Obtained in the Hydrostannation of Ethynes," J Organometal Chem 9:285–294 (1967).

Loke et al., "Characterization of oligonucleotide transport into living cells," Proc Natl Acad Sci 86:3474–3478 (1989).

Robins et al., "Nucleic Acid Related Compounds. 31. Smooth and Efficient Palladium–Copper Catalyzed Coupling of Terminal Alkynes with 5–Iodouracil Nucleosides," Tet Lett 22:421–424 (1981).

Robins et al., "Nucleic Acid Related Compounds. 39. Efficient Conversion of 5–Iodo to 5–Alkynyl and Derived 5–Substituted Uracil Bases and Nucleosides," J Org Chem 48:1854–1862 (1983).

Robins et al., "Solvent, Not Palladium Oxidation State, is the Primary Determinant for Successful Coupling of Terminal Alkynes with Iodo–Nucleosides," Tet Lett 31(26):3731–3734 (1990).

Vincent et al., "Alcynyl–5 Desoxy–2' Uridines Par Couplages D'Organozinciques Acetyleniques Avec L'iodo–5 0–3', 5'–Bis(Trimethylsilyl) Desoxyuridine, Catalyses Par Des Complexes Organopalladies et de Nickel," Tet Lett 22:945–947 (1981).

Augustyns et al., "Incorporation of hexose nucleoside analogues into oligonucleotides: synthesis, base–pairing properties and enzymatic stability," Nuc Acids Res 20:4711–4716 (1992).

Chiang et al., "Antisense Oligonucleotides Inhibit Intercellular Adhesion Molecule 1 Expression by Two Distinct Mechanisms," J Biol Chem 266:18162–18171 (1991).

Clivio et al., "Synthesis of Dinucleoside Phosphates Containing Sulfur Substutited Nucleobase: 4–Thiouracil, 4–Thiothymine and 6–Mercaptopurine," Tet Lett 33:69–72 (1992).

Connolly et al., "Synthesis and properties of oligonucleotides containing 4–thiothymidine, 5–methyl–2–pyrimidinone–1–b–D(2'–deoxyriboside) and 2–thiothymidine," Nuc Acids Res 17:4957–4974 (1989).

Cooney et al., "Site–Specific Oligonucleotide Binding Represses Transcription of the Human c–myc Gene In Vitro," Science 241:456–459 (1988).

De Clercq et al., "Nucleic Acid Related Compounds. 40. Synthesis and Biological Acitivities of 5–Alkynyluracil Nucleosides," J Med Chem 26:661–666 (1983).

Egholm et al., "Peptide Nucleic Acids (PNA). Oligonucleotide Analogues with an Achiral Peptide Backbone," J Am Chem Soc 114:1895–1897 (1992).

Fedorovo et al., "Complementary addressed modification of double–stranded DNA within a ternary complex," Febs 228:273–276 (1988).

Felgner et al., "Lipofection: A highly efficient, lipid–mediated DNA–transfection procedure," Proc Natl Acad Sci 84:7413–7417 (1987).

Froehler et al., "Oligodeoxynucleotides Containg C–5 Propyne Anaologs of 2'–Deoxyuridine and 2'–Deoxycytidine," Tet Lett 33:5307–5310 (1992).

Froehler et al., "Triple–Helix Formation and Cooperative Binding by Oligodeoxynucleotides with a 3'–3' Internucleotide Junction," Biochem 31:1603–1609 (1992).

Froehler et al., "Triple–Helix Formation by Oligodeoxynucleotides Containing the Carbocyclic Analogs of Thymidine and 5–Methyl–2–deoxycytidine," J Am Chem Soc 114:8320–8322 (1992).

Goodchild et al., "Structural Requirements of Olefinic 5–Substituted Deoxyuridines for Antiherpes Activity," J Med Chem 26:1252–1257 (1983).

Iverson et al., "Nonenzymatic Sequence–Specific Cleavage of Single–Stranded DNA to Nucleotide Resolution. DNA Methyl Thioether Probes," J Am Chem Soc 109:1241–1243 (1987).

Knorre et al., "Reactive oligonucleotide derivatives and sequence–specific modification of nucleic acids," Biochimie 67:785–789 (1985).

Lee et al., "Interaction of Psoralen–Derivatized Oligodexoyribonucleoside Methylphosphonates with Single–Stranded DNA," Biochem 27:3197–3203 (1988).

Lee et al., "Poly(pyrimidine) • poly(purine) synthetic DNAs containing ???," Nuc Acids Res 12:6603–6614 (1984).

Maher et al., "Inhibition of DNA Binding Proteins by Oligonucleotide–Directed Triple Helix Formation," Science 245:725–730 (1989).

Matteucci et al., "Synthesis and Crosslinking Properties of a Deoxyoligonucleotide Containing N[6],N[6]–Ethanodeoxyadenosine," Tet Lett 28:2469–2472 (1987).

Meyer et al., "Efficient, Specific Cross–Linking and Cleavage of DNA by Stable, Synthetic Complementary Oligodeoxynucleotides," J Am Chem Soc 111:8517–8519 (1989).

Murakami et al, "Highly sensitive detection of DNA using enzyme–linked DNA–probe. 1. Colorimetric and fluorometric detection," Nuc Acids Res 17(14)5587–5595 (1989).

Nielson et al., "Sequence–Selective Recognition of DNA by Strand Displacement with a Thymine–Substituted Polyamide," Science 254:1497–1500 (1991).

Ötvös et al., "Substrate specificity of DNA polymerases. I. Enzyme–catlysed incorporation of 5–(1–alkenyl)–2'–deoxyuridines into DNA," Nuc Acids Res 15:1763–1777 (1987).

Ötvös et al., "Substrate specificity of DNA polymerases. II. 5–(1–Alkynyl)–dUTPs as substrates of the Klenow DNA polymerase enzyme," Chem Ab 107(23):214012g (1987).

Ono et al., "Triplex Formation of an Oligonucleotide Containing 2'–0–Methylpseudoisocytidine with a DNA Dupliex at Neutral pH," J Org Chem 57:3225–3230 (1992).

Rahim, "Preparation of 5–prop–1–ynyl–1–(5–0–trimethyl . . . ," Chem Ab 113(25):231937d (1990).

Rahim et al., "5–Alkynl pyrimidine nucleosides as potent selective inhibitors of varicella–zoster virus," Antiviral Chem & Chemo 3:293–297 (1992).

Reynolds et al., "Synthesis of Thymidine Dimers Containing Internucleoside Sulfonate and Sulfonamide Linkages," J Org Chem 57:2983–2985 (1992).

Robins et al., "Nucleic acid related compounds. 38. Smooth and high–yield iodination and chlorination at C–5 of uracil bases and p–totuyl–protected nucleosides," Can J Chem 60:554–557 (1982).

Uhlmann et al., "Antisense Oligonucleotides: A New Therapeutic Principle," Chem Rev. 90:543–584 (1990).

Valko et al., "Application of chromatographic retention data in an investigation of a quantitative structure –nucleotide incorporation rate relationship," J Chromatog 506:35–44 (1990).

Valko et al., "Correlation of Nucleotide Incorporation Rate and HPLC Retention Parameters of Substituted Nucleosides," J Liquid Chromatog 12:2103–2116 (1989).

van der Krol et al., "Modulation of Eukaryotic Gene Expression by Complementary RNA or DNA Sequences," Biotechniques 6:958–976 (1988).

Vasseur et al., "Oligonucleosides: Synthesis of a Novel Methylhydroxylamine–Linked Nucleoside Dimer and Its Incorporation into Antisense Sequences," J Am Chem Soc 114:4006–4007 (1992).

Vlassov et al., "Complementary addressed modification and cleavage of a single stranded DNA fragment with alkylating oligonucleotide derivatives," Nuc Acids Res 14:4065–4076 (1986).

Webb et al., "Hybridization triggered cross–linking of deoxyoligonucleotides," Nuc Acids Res 14:7661–7674 (1986).

Webb et al., "Sequence–Specific Cross–Linking of Deoxyoligonucleotides via Hybridization–Triggered Alkylation," J Am Chem Soc 108:2764–2765 (1986).

Wigerinck et al., "5–(5–Bromothien–2–yl)–2'–deoxyuridine and 5–(5–Chlorothien–2–yl)–2'–deoxyuridine Are Equipotent to (E)–5–(2–Bromovinyl)–2'–deoxyuridine in the Inhibition of Herpes Simplex Virus Type I Replication," J Med Chem 64:2383–2389 (1991).

Albretsen et al, "Optimal Conditions for Hybridization with Oligonucleotides: A Study with myc–Oncogene DNA Probes," Anal Biochem 170:192–202 (1988).

Augustyns et al., "Incorporation of hexose nucleoside analogues into oligonucleotides: synthesis, base–pairing properties and enzymatic stability," Nuc Acids Res 20:4711–4716 (1992).

Balzarini et al., "Incorporation of 5–substituted pyrimidine nucleoside analogs into DNA of a thymidylate synthetase–deficient murine FM3A carcinoma cell line," Chem Ab 103(3):16283a (1985).

Beal et al., "Second Structural Motif for Recognition of DNA by Oligonucleotide–Directed Triple–Helix Formation," Science 251:1360–1363 (1990).

Capobianco et al., "One pot solution synthesis of cyclic oligondeoxyribonucleotides," Nuc Acids Res 18:2661–2669 (1990).

Casey et al, "Rates of formation and thermal stabilties of RNA:DNA and DNA:DNA duplexes at high concentration of formamide," Nuc Acids Res 4(5):1539–1552 (1977).

Chiang et al., "Antisense Oligonucleotides Inhibit Intercellular Adhesion Molecule 1 Expression by Two Distinct Mechanisms," J Biol Chem 266:18162–18171 (1991).

Clivio et al., "Synthesis of Dinucleoside Phosphates Containing Sulfur Substutited Nucleobase: 4–Thiouracil, 4–Thiothymine and 6–Mercaptopurine," Tet Lett 33:69–72 (1992).

Connolly et al., "Synthesis and properties of oligonucleotides containing 4–thiothymidine, 5–methyl–2–pyrimidinone–1–b–D(2'–deoxyriboside) and 2–thiothymidine," Nuc Acids Res 17:4957–4974 (1989).

Cooney et al., "Site–Specific Oligonucleotide Binding Represses Transcription of the Human c–myc Gene In Vitro," Science 241:456–459 (1988).

De Clercq et al., "Nucleic Acid Related Compounds. 40. Synthesis and Biological Activities of 5–Alkynyluracil Nucleosides." J Med Chem 26:661–666 (1983).

Egholm et al., "Peptide Nucleic Acids (PNA). Oligonucleotide Analogues with an Archiral Peptide Backbone," J Am Chem Soc 114:1895–1897 (1992).

Fedorovo et al., "Complementary addressed modification of double–stranded DNA within a ternary complex," Febs 228:273–276 (1988).

Felgner et al., "Lipofection: A highly efficient, lipid–mediated DNA–transfection procedure," Proc Natl Acad Sci 84:7413–7417 (1987).

Froehler et al., "Oligodeoxynucleotides Containing C–5 Propyne Analogs of 2'–Deoxyuridine and 2'–Deoxycytidine," Tet Lett 33:5307–5310 (1992).

Froehler et al., "Triple–Helix Formation and Cooperative Binding by Oligodeoxynucleotides with a 3'–3' Internucleotide Junction," Biochem 31:1603–1609 (1992).

Froehler et al., "Triple–Helix Formation by Oligodeoxynucleotides Containing the Carbocyclic Analogs of Thymidine and 5–Methyl–2'–deoxycytidine," J Am Chem Soc 114:8320–8322(1992).

Goodchild et al., "Structural Requirements of Olefinic 5–Substitituted Deoxyuridines for Antiherpes Activity," J Med Chem 26:1252–1257 (1983).

Griffin et al., "Recognition of Thymine–Adenine Base Pairs by Guanine in a Pyrimidine Triple Helix Motif," Science 245:967–971 (1989).

Hamaguchi et al, "The Effect of Electrolytes on the Stability of the Deoxyribonucleate Helix," J Am Chem Soc 84:1329–1338 (1962).

Horne et al., "Recognition of Mixed–Sequence Duplex DNA by Alternate–Strand Triple–Helix Formation," J Am Chem Soc 112:2435–2437 (1990).

Hutton, James R., "Renaturation kinetics and thermal stability of DNA in aqueous solutions of formamide and urea," Nuc Acids Res 4(10):3537–3555 (Oct. 1977).

Iverson et al., "Nonenzymatic Sequence–Specific Cleavage of Single–Stranded DNA to Nucleotide Resolution. DNA Methyl Thioether Probes," J Am Chem Soc 109:1241–1243 (1987).

Knorre et al., "Reactive oligonucleotide derivatives and sequence–specific modification of nucleic acids," Biochimie 67:785–789 (1985).

Krawczyk et al., "Oligonucleotide–mediated triple helix formation using and N[3]–protonated deoxycytidine analog exhibiting pH–independent binding within the pysiological range," Proc Natl Acad Sci 89:3761–3764 (1992).

Lee et al., "Interaction of Psoralen–Derivatized Oligodexoyribonucleoside Methylphosphonates with Single–Stranded DNA," Biochem 27:3197–3203 (1988).

Lee et al., "Poly(pyrimdine)•poly(purine) synthetic DNAs containing ???," Nuc Acids Res 12:6603–6614 (1984).

Maher et al., "Inhibition of DNA Binding Proteins by Oligonucleotide–Directed Triple Helix Formation," Science 245:725–730 (1989).

Matteucci et al., "Synthesis and Crosslinking Properties of a Deoxyoligonucleotide Containing N[6], N[6]–Ethanodeoxyadenosine," Tet Lett 28:2469–2472 (1987).

Matthews et al, "Analytical Strategies for the Use of DNA Probes," Anal Biochem 169:1–25 (1988).

Meyer et al., "Efficient, Specific Cross–Linking and Cleavage of DNA by Stable, Synthetic Complementary Oligodeoxynucleotides," J Am Chem Soc 111:8517–8519 (1989).

Moser et al., "Sequence–Specific Cleavage of Double Helical DNA by Triple Helix Formation," Science 238:645–650 (1987).

Murakami et al., "Highly sensitive detection of DNA using enzyme–linked DNA–probe, 1. Colorimetric and fluorometric detection," Nuc Acids Res 17(14):5587–5595 (1989).

Nielsen et al., "Sequence–Selective Recognition of DNA by Strand Displacement with a Thymine–Substituted Polyamide," Science 254:1497–1500 (1991).

Ono et al., "Triplex Formation of an Oligonucleotide Containing 2'–0–Methylpseudoisocytidine with a DNA Dupliex at Neutral pH," J Org Chem 57:3225–3230 (1992).

Petrie et al, "A Novel Biotinylate Analogue Derived from Pyrazolo[3,4–d]pyrimidine for Labeling DNA Probes," Bioconj Chem 2:441–446 (1991).

Povsic et al., "Triple Helix Formation by Oligonucleotides on DNA Extended to the Physiological pH Range," J Am Chem Soc 111:3059–3061 (1989).

Praseuth et al., "Sequence–specific binding and photo-crosslinking of a and b oligodeoxynucleotides to the major groove of DNA via triple–helix formation," Proc Natl Acad Sci 85:1349–1353 (1988).

Quartin et al, "Effect of Ionic Strengh on the Hybridization of Oligodeoxynucleotides with Reduced Charge Due to Methylphoshonate Linkages to Unmodified Oligodeoxynucleotides Containing the Complementary Sequence," Biochem 28:1040–1047 (1989).

Rahim, "Preparation of 5–prop–1–ynyl–1–(5–0–trimethyl . . . ," Chem Ab 113(25):231937d (1990).

Rahim et al., "5–Alkynl pyrimidine nucleosides as potent selective inhibitors of varicella–zoster virus," Antiviral Chem & Chemo 3:293–297 (1992).

Reynolds et al., "Snythesis of Thymidine Dimers Containing Internucleoside Sulfonate and Sulfonamide Linkages," J Org Chem 57:2983–2985 (1992).

Robins et al., "Nucleic acid related compounds. 38. Smooth and high–yield iodination and chlorination at C–5 of uracil bases and p–totuyl–protected nucleosides," Can J Chem 60:554–557 (1982).

Shaw et al., "Specific, High–Efficiency, Triple–Helix–Medicated Cross–Linking to Duplex DNA," J Am Chem Soc 113:7765–7766 (1991).

Thompson et al, "Molecular Hybridization with RNA Probes in Concentrated Solutions of Guanidine Thiocyanate," Anal Biochem 163:281–291 (1987).

Uhlmann et al, "Antisense Oligonucleotides: A New Therapeutic Principle," Chem Rev 90:543–584 (1990).

Valko et al., "Application of chromatographic retention data in an investigation of a quantitative structure—nucleotide incorporation rate relationship," J Chromatog 506:35–44 (1990).

Valko et al., "Correlation of Nucleotide Incorporation Rate and HPLC Retention Parameters of Substituted Nucleosides," J Liquid Chromatog 12:2103–2116 (1989).

Van Ness et al, "The use of oligodeoxynucleotide probes in chaotrope–based hybridization solutions," Nuc Acids Res 19(19):5143–5151 (1991).

Vasseur et al., "Oligonucleosides: Synthesis of a Novel Methylhydroxylamine–Linked Nucleoside Dimer and Its Incorporation into Antisense Sequences," J Am Chem Soc 114:4006–4007 (1992).

Vlassov et al., "Complementary addressed modification and cleavage of a single stranded DNA fragment with alkylating oligonucleotide derivatives," Nuc Acids Res 14:4065–4076 (1986).

Vlassov et al., "Sequence–specific chemical modification of double–stranded DNA with alkylating oligodeoxyribonucleotide derivatives," Gene 72:313–322 (1988).

Webb et al., "Hybridization triggered cross–linkiing of deoxyoligonucleotides," Nuc Acids Res 14: 7661–7674 (1986).

Webb et al., "Sequence–Specific Cross–Linking of Deoxyoligonucleotides via Hybridization–Triggered Alkylation," J Am Chem Soc 108:2764–2765 (1986).

Wigerinck et al., "5–(5–Bromothien–2–yl)–2'–deoxyuridine and 5–(5–Chlorothein–2–yl)–2'–deoxyuridine Are Equipotent to (E)–5–(2–Bromovinyl)–2'–deoxyuridine in the Inhibition of Herpes Simplex Virus Type I Replication," J Med Chem 34:2383–2389 (1991).

Young et al., "Triple helix formation inhibits transcription elongation in vitro," Proc Natl Acad Sci 88:10023–10026 (1991).

van de sande, "Parallel Stranded DNA," Science 241:551–557 (1988).

van der Krol et al., "Modulation of Eukaryotic Gene Expression by Complementary RNA or DNA Sequences," Biotechniques 6:958–976 (1988).

Ötvös et al., "Substrate specificity of DNA polymerases. I. Enzyme–catlysed incorporation of 5–(1–alkenyl)–2'–deoxyuridines in DNA," Nuc Acids Res 15:1763–1777 (1987).

Ötvös et al., "Substrate specificity of DNA polymerases. II. 5–(1–Alkynyl)–dUTPs as substrates of the Klenow DNA polymerase enzyme," Chem Ab 107(23):214012g (1987).

(8)

(9)

(10)

(11)

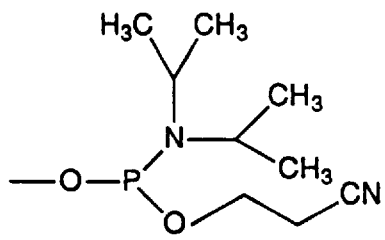
N,N-diisopropylamino-β-cyanoethoxyphosphine
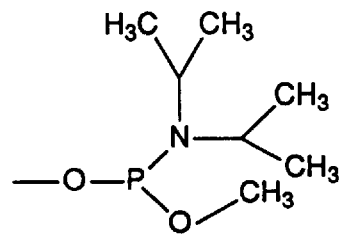
N,N-diisopropylamino-methoxyphosphine
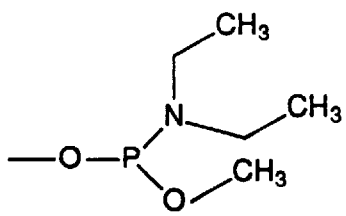
N,N-diethylamino-methoxyphosphine
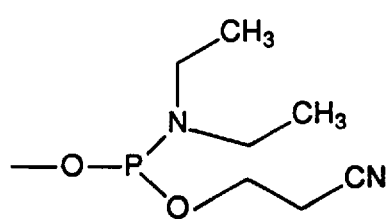
N,N-diethylamino-β-cyanoethoxy phosphine
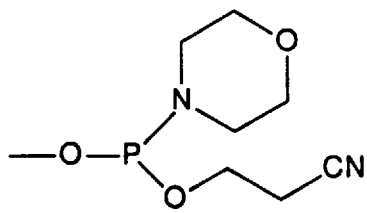
N-morpholino-β-cyanoethoxyphosphine
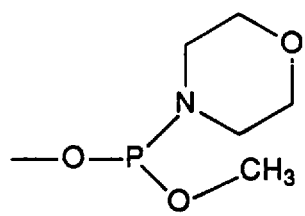
N-morpholino methoxyphosphine
Figure 10-1

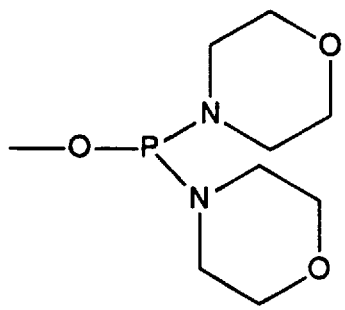
Bis morpholino-phosphine
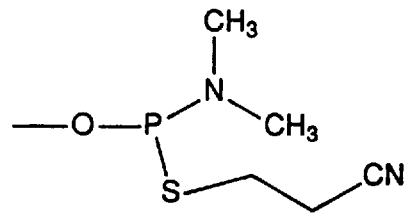
N,N-dimethylamino-
β-cyanoethylmercapto-phosphine
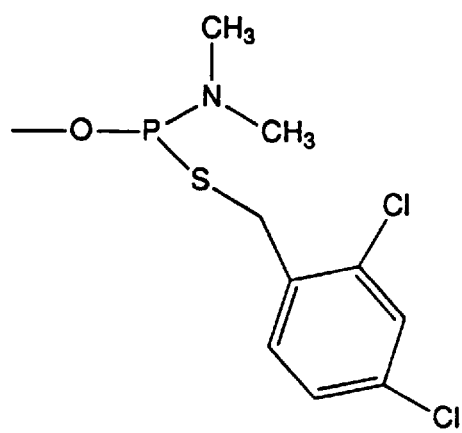
N,N-dimethylamino-
2,4-dichlorobenzylmercapto-
phosphine
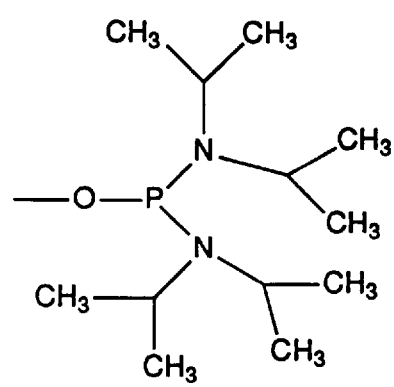
Bis(N,N-diisopropylamino)-
phosphine
Figure 10-2

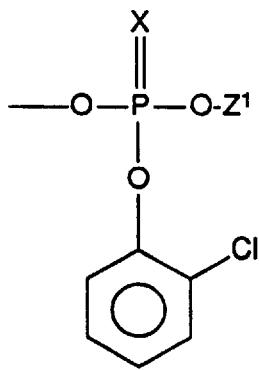
2-chlorophenyl phosphate
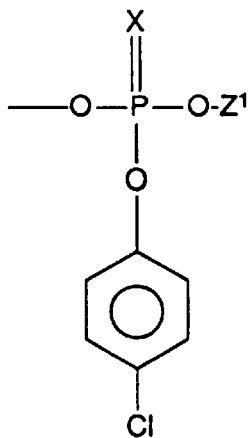
4-chlorophenyl phosphate
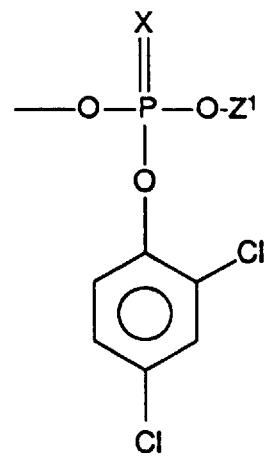
2,4-dichlorophenyl phosphate
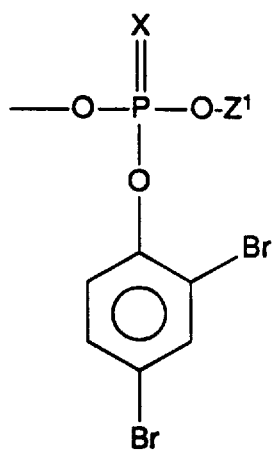
2,4-dibromophenyl phosphate
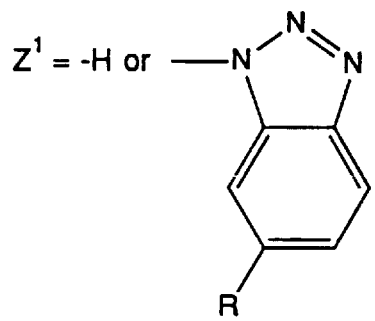
X = O or S
R = H, $NO_2$ and $CF_3$
Figure 10-3

N,N-diisopropylamino-methyl-phosphine

N,N-diethylamino-methyl-phosphine

METHODS OF USING OLIGOMERS CONTAINING MODIFIED PYRIMIDINES

This is a divisional of application Ser. No. 07/976,103 filed on Nov. 25, 1992, now Pat. No. 5,645,985, which is a continuation-in-part of U.S. Ser. No. 07/965,941, filed Oct. 23, 1992, now abandoned, which is a continuation-in-part of U.S. Ser. No. 07/935,444, filed Aug. 25, 1992, now abandoned, which is a continuation-in-part of U.S. Ser. No. 07/799,824, filed Nov. 26, 1991, now Pat. No. 5,484,908.

TECHNICAL FIELD

The invention relates generally to novel nucleomonomer and oligomer analogs, and to oligonucleotide-based therapy and diagnosis by binding of the oligonucleotide analogs to single or double-stranded nucleic acid target sequences. More specifically, the invention concerns oligomers containing certain 5-substituted pyrimidine base residues and intermediates in their synthesis.

BACKGROUND ART

Sequence-specific binding of oligonucleotides both to single-stranded RNA and DNA and to duplex DNA has been demonstrated. The appropriate sequence recognition for binding to single-stranded targets is well known: the A-T and G-C pairing characteristic of duplex formation has been established as the basis for DNA replication and transcription.

More recently, oligonucleotides have been shown to bind in a sequence-specific manner to duplex DNA to form triplexes. Single-stranded nucleic acid, primarily RNA, is the target molecule for oligonucleotides that are used to inhibit gene expression by an "antisense" mechanism (Uhlmann, E., et al, *Chem Reviews* (1990) 90:543–584; van der Krol, A. R., et al, *Biotechniques* (1988) 6:958–976). Antisense oligonucleotides are postulated to exert an effect on target gene expression by hybridizing with a complementary RNA sequence. In this model, the hybrid RNA-oligonucleotide duplex interferes with one or more aspects of RNA metabolism including processing, translation and metabolic turnover. Chemically modified oligonucleotides have been used to enhance their nuclease stability.

Duplex DNA can be specifically recognized by oligomers based on a recognizable nucleomonomer sequence. Two major recognition motifs have been recognized. In an earlier description of a "CT" motif, protonated cytosine residues recognize G-C basepairs while thymine residues recognize A-T basepairs in the duplex. These recognition rules are outlined by Maher III, L. J., et al., *Science* (1989) 245:725–730; Moser, H. E., et al., *Science* (1987) 238:645–650. More recently, an additional motif, termed "GT" recognition, has been described (Beal, P. A., et al, *Science* (1992) 251:1360–1363; Cooney, M., et al., *Science* (1988) 241:456–459; Hogan, M. E., et al., EP Publication 375408). In the G-T motif, A-T pairs are recognized by adenine or thymine residues and G-C pairs by guanine residues.

In both of these binding motifs, the recognition sequence of the oligomer must align with the complementary sequence of the purine chain of-the duplex; thus, recognition, for example, of an A-T pair by a thymine, depends on the location of the adenyl residues along the purine chain of the duplex. An exception to the foregoing is the recent report by Griffin, L. C., et al., *Science* (1989) 245:967–971, that limited numbers of guanine residues can be provided within pyrimidine-rich oligomers and specifically recognize thymine-adenine base pairs; this permits the inclusion of at least a limited number of pyrimidine residues in the homopurine target.

The two motifs exhibit opposite binding orientations with regard to homopurine target chains in the duplex. In the CT motif, the targeting oligonucleotide is oriented parallel to the target purine-rich sequence; in the GT motif, the oligonucleotide is oriented antiparallel (Beal, P. A., et al., *Science* (1990) 251:1360–1363).

The efficiency of binding by C residues in CT motif oligomers is reduced as the pH of hybridization is increased. The protonated tautomer of C ($C^+$) is the binding competent species in Hoogsteen binding, but is present at only low levels at physiological pH. This is consonant with the $pK_a$ of cytosine which is 4.25. Base analogs such as 5-methylcytosine, $pK_a$ 4.35, (Lee, J. S. et al., *Nucleic Acids Res* (1984) 12:6603–6614), 8-oxo-$N^6$-methyladenine (Krawczyk, S. H. et al, *Proc Natl Acad Sci* (1992) 89:3761–3764; International Application No. PCT/US91/08811), pseudoisocytidine (Ono, A., et al, *J Org Chem* (1992) 57:3225–3230; International Application No. PCT/US90/03275) or carbocyclic cytidine (Froehler, B. C., et al, *J Am Chem Soc* (1992) 114:8320–8322; U.S. Pat. application Ser. No. 07/864,873 incorporated herein by reference) have been utilized to obtain binding of CT motif oligomers over an extended pH range.

Sequence-specific targeting of both single-stranded and duplex target sequences has applications in diagnosis, analysis, and therapy. Under some circumstances wherein such binding is to be effected, it is advantageous to stabilize the resulting duplex or triplex over long time periods.

Covalent crosslinking of the oligomer to the target provides one approach to prolong stabilization. Sequence-specific recognition of single-stranded DNA accompanied by covalent crosslinking has been reported by several groups. For example, Vlassov, V. V., et al., *Nucleic Acids Res* (1986) 14:4065–4076, describe covalent bonding of a single-stranded DNA fragment with alkylating derivatives of nucleomonomers complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleomonomer which was capable of activating cleavage (*J Am Chem Soc* (1987) 109:1241–1243). Meyer, R. B., et al., *J Am Chem Soc* (1989) 111:8517–8519, effect covalent crosslinking to a target nucleomonomer using an alkylating agent complementary to the single-stranded target nucleomonomer sequence. Photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Horne, et al., *J Am Chem Soc* (1990) 112:2435–2437.

Use of $N^4,N^4$-ethanocytosine as an alkylating agent to crosslink to single-stranded and double-stranded oligomers has also been described (Webb and Matteucci, *J Am Chem Soc* (1986) 108:2764–2765; *Nucleic Acids Res* (1986) 14:7661–7674; Shaw, J. P., et al, *J Am Chem Soc* (1991) 113:7765–7766). These papers also describe the synthesis of oligonucleotides containing the derivatized cytosine. Matteucci and Webb, in a later article in *Tetrahedron Letters* (1987) 28:2469–2472, describe the synthesis of oligomers containing $N^6,N^6$-ethanoadenine and the crosslinking properties of this residue in the context of an oligonucleotide binding to a single-stranded DNA.

In a recent paper, Praseuth, D., et al., *Proc Natl Acad Sci (USA)* (1988) 85:1349–1353, described sequence-specific binding of an octathymidylate conjugated to a photoactivatable crosslinking agent to both single-stranded and double-stranded DNA.

In addition, Vlassov, V. V. et al., *Gene* (1988) 313–322 and Fedorova, O. S. et al., *FEBS* (1988) 228:273–276, describe targeting duplex DNA with an alkylating agent linked through a 5'-phosphate of an oligonucleotide.

In effecting binding to obtain a triplex, to provide for instances wherein purine residues are concentrated on one chain of the target and then on the opposite chain, oligomers of inverted polarity can be provided. By "inverted polarity" is meant that the oligomer contains tandem sequences which have opposite polarity, i.e., one having polarity 5'→3' followed by another with polarity 3'→5', or vice versa. This implies that these sequences are joined by linkages which can be thought of as effectively a 3'—3' internucleoside junction (however the linkage is accomplished), or effectively a 5'—5' internucleoside junction. Such oligomers have been suggested as by-products of reactions to obtain cyclic oligonucleotides by Capobionco, M. L., et al., *Nucleic Acids Res* (1990) 18:2661–2669. Compositions of "parallel-stranded DNA" designed to form hairpins secured with AT linkages using either a 3'—3' inversion or a 5'—5' inversion have been synthesized by van de Sande, J. H., et al., *Science* (1988) 241:551–557. In addition, triple helix formation using oligomers which contain 3'—3' linkages have been described (Horne, D. A., and Dervan, P. B., *J Am Chem Soc* (1990) 112:2435–2437; Froehler, B. C., et al, *Biochemistry* (1992) 31:1603–1609).

The use of triple helix (or triplex) complexes as a means for inhibition of the expression of target gene expression has been previously adduced (International Application No. PCT/US89/05769). Triple helix structures have been shown to interfere with target gene expression (International Application No. PCT/US91/09321; Young, S. L. et al, *Proc Natl Acad Sci* (1991) 88:10023–10026), demonstrating the feasibility of this approach.

European Patent Application No. 92103712.3, Rahim, S. G., et al (*Antiviral Chem Chemother* (1992) 3:293–297), and International Application No. PCT/SE91/00653 describe pyrimidine nucleomonomer characterized by the presence of an unsaturated group in the 5-position. Propynyl and ethynyl groups are included among the derivatives at the 5-position that are described in the applications.

Synthesis of nucleomonomers having unsaturated alkyl groups at the 5-position of uracil has been described (DeClercq, E., et al, *J Med Chem* (1983) 26:661–666; Goodchild, J., et al, *J Med Chem* (1983)26:1252–1257). Oligomers containing 5-propynyl modified pyrimidines have been described (Froehler, B. C., et al, *Tetrahedron Letters* (1992) 33:5307–5310).

Conversion of 5-propynyl-2'-deoxyuridine, 5-butynyl-2'-deoxyuridine and related compounds to the 5'-triphosphate followed by incorporation of the monomer into oligomers by *E. coli* polymerase has been described (Valko, K., et al, *J Liquid Chromatog* (1989) 12:2103–2116; Valko, K. et al, *J Chromatoa* (1990) 506:35–44). These studies were conducted as a structure to activity analysis of nucleotide analogs having a series of substitutions at the 5- position of uracil. The activity of the nucleotide analogs as substrates for *E. coli* polymerase was examined and correlated with characteristics such as the hydrophobicity of the monomer. No information was presented regarding the properties of oligomers containing the analogs.

European patent application 0492570 published Jul. 1, 1992 describes a method for detecting a target polynucleotide using a single-stranded polynucleotide probe in which an intercalating molecule is attached by a linker which comprises at least 3 carbon atoms and a double bond at the alpha position relative to the base.

PCT patent publication WO 92/02258 describes nuclease resistant, pyrimidine modified oligomers including a substituent group at the 5 or 6 positions, including phenyl. 5-Phenyl-2'-deoxyuridine has been subsequently incorporated into oligomers and shown to decrease the binding affinity of oligomers containing this modification for both single stranded and double stranded target sequences.

DNA synthesis via amidite and hydrogen phosphonate chemistries has been described (U.S. Pat. Nos. 4,725,677; 4,415,732; 4,458,066; 4,959,463).

Oligomers having enhanced affinity for complementary target nucleic acid sequences would have improved properties for diagnostic applications, therapeutic applications and research reagents. Thus, a need exists for oligomers with enhanced binding affinity for complementary sequences. oligomers of the present invention have improved binding affinity for double stranded and/or single stranded target sequences.

BRIEF DESCRIPTION OF FIGURES

FIGS. 4-1 and 4-2 show synthesis of monomers containing 2'-O-allyl modifications.

FIGS. 5-1 and 5-2 show synthesis of o-xylene linked switchback dimers (synthetic method #1).

FIGS. 8-1 and 8-2 show synthesis of trimer linked by a 3'-thioformacetal linkage (method #2).

FIGS. 9-1 and 9-2 show synthesis of dimer linked by a riboacetal linkage (method #3).

FIGS. 10-1, 10-2 10-3 and 10-4 show coupling groups for oligomer synthesis via amidite or triester chemistry.

FIGS. 12-1, 12-2 and 12-3 show oligomer synthesis by (1) hydrogen-phosphonate, (2) amidite chemistry and (3) methyl phosphonate derivatives (method #1).

FIGS. 17-1, 17-2 and 17-3 show oligomers containing amide substitute linkages; repeating nucleomonomer units and exemplary amide-linked oligomer structures.

STRICTURAL FORMULAS

Figure 1:
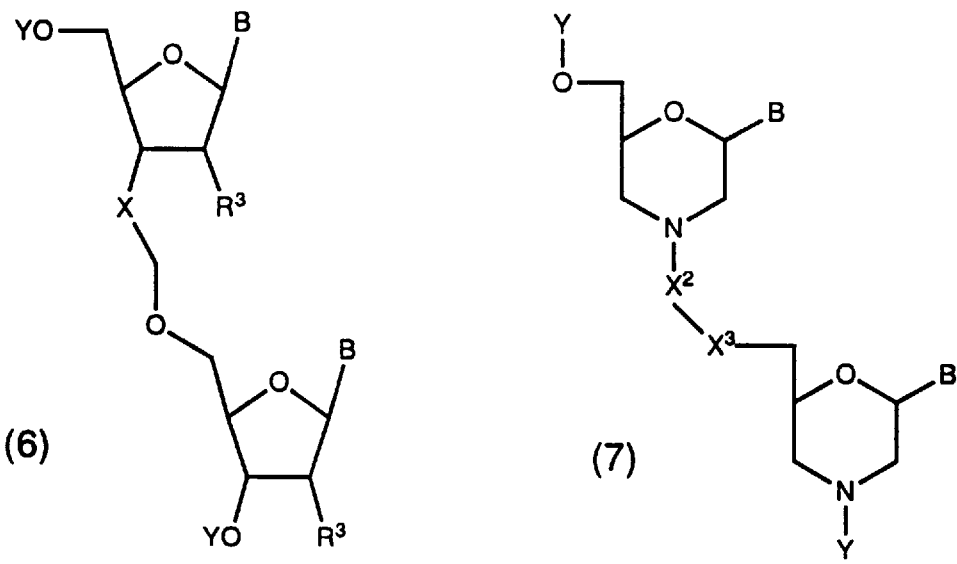
FIG. 1. Dimer synthons containing bases of the invention.

Structural formulas that are described herein are designated as a numeral in parentheses ((1), (2), etc.) and chemical compounds are designated as an underlined numeral (1, 2, etc.).

DISCLOSURE OF THE INVENTION

The invention provides an oligomer comprising at least two and preferably a multiplicity of nucleomonomers wherein at least one nucleomonomer comprises a base of formula (1) or (2)

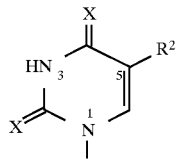

(1)

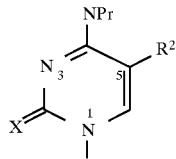

(2)

wherein each X is independently O or S;
R$^2$ is a group comprising at least one pi bond connected to a carbon atom attached to the base; and
Pr is (H)$_2$ or a protecting group,
with the proviso that when at least one of said nucleomonomers of said oligomer comprises deoxyuridine 5-substituted by vinyl, 1-butenyl, 1-pentenyl, 1-hexenyl, 1-heptenyl, 1-octenyl, 1-propynyl, 1-butynyl, 1-hexynyl, 1-heptynyl, or 1-octynyl, then the remainder of the nucleomonomers comprising said oligomer are not solely comprised of phosphodiester linked 2'-deoxyadenosine, 2'-deoxyguanosine, 2'-deoxycytidine, thymidine or a combination thereof.

Definitions

The following definitions are brief synopses of terms that are more fully defined hereinbelow.

Nucleomonomer. As used herein, the term "nucleomonomer" means a moiety comprising (1) a base covalently linked to (2) a second moiety. Nucleomonomers include nucleosides and nucleotides. Nucleomonomers can be linked to form oligomers that bind to target or complementary base sequences in nucleic acids in a sequence specific manner.

A "second moiety" as used herein includes those species which contain modifications of the sugar moiety, for example, wherein one or more of the hydroxyl groups are replaced with a halogen, a heteroatom, an aliphatic groups, or are functionalized as ethers, amines, and the like. The pentose moiety can be replaced by a hexose or an alternate structure such as a cyclopentane ring, a 6-member morpholino ring and the like. Nucleosides as defined herein are also intended to include a base linked to an amino acid and/or an amino acid analog having a free carboxyl group and/or a free amino group and/or protected forms thereof Base. "Base" as used herein includes those moieties which contain not only the known purine and pyrimidine heterocycles and the invention pyrimidines, but also heterocycle analogs and tautomers thereof. Purines include adenine, guanine and xanthine and exemplary purine analogs include 8-oxo-N$^6$-methyladenine and 7-deazaxanthine. Pyrimidines include uracil and cytosine and their analogs such as 5-methylcytosine, 5-methyluracil and 4,4-ethanocytosine. Invention bases are pyrimidines derivatized at the 5- position. The derivatives are 1-alkenyl-, 1-alkynyl-, heteroaromatic- and 1-alkynyl-heteroaromatic modifications. "1-Alkenyl" means an olefinically-unsaturated (double bond containing) acyclic group. "1-Alkynyl" means an acetylenically-unsaturated (triple bond containing) acylic group. "Heteroaromatic" means a compound having at least one heterocyclic ring, 5 or 6 ring atoms, having physical and chemical properties resembling compounds such as an aromatic group. "Heteroaromatic" also means systems having one or more rings, including bicyclic moieties such as benzimidazole, benzotriazole, benzoxazole, and indole. A base also includes heterocycles such as 2-aminopyridine and triazines. 1-Alkynyl-heteroaromatic means 1-ethynyl-heteroaryl wherein heteroaryl is as defined above.

Nucleoside. As used herein, "nucleoside" means a base covalently attached to a sugar or sugar analog and which may contain a phosphite or phosphine. The term nucleoside includes ribonucleosides, deoxyribonucleosides, or any other nucleoside which is an N-glycoside or C-glycoside of a base. The stereochemistry of the sugar carbons can be other than that of D-ribose.

Nucleosides include those species which contain modifications of the sugar moiety, for example, wherein one or more of the hydroxyl groups are replaced with a halogen, a heteroatom, an aliphatic groups, or are functionalized as ethers, amines, thiols, and the like. The pentose moiety can be replaced by a hexose or an alternate structure such as a cyclopentane ring, a 6-member morpholino ring and the like. Nucleosides as defined herein are also intended to include a base linked to an amino acid and/or an amino acid analog having a free carboxyl group and/or a free amino group and/or protected forms thereof.

Nucleotide. As used herein, "nucleotide" means nucleoside having a phosphate group or phosphate analog.

Sugar Modification. As used herein, "sugar modification" means any pentose or hexose moiety other than 2'-deoxyribose. Modified sugars include D-ribose, 2'-O-alkyl, 2'-amino, 2'-halo functionalized pentoses, hexoses and the like. Sugars having a stereochemistry other than that of a D-ribose are also included.

Linkage. As used herein, "linkage" means a phosphodiester moiety (—O—P(O)(O)—O—) that covalently couples adjacent nucleomonomers.

Substitute Linkages. As used herein, "substitute linkage" means any analog of the native phosphodiester group that covalently couples adjacent nucleomonomers. Substitute linkages include phosphodiester analogs, e.g. such as phosphorothioate and methylphosphonate, and nonphosphorus containing linkages, e.g. such as acetals and amides.

Switchback. As used herein, "switchback" means an oligomer having at least one region of inverted polarity. Switchback oligomers are able to bind to opposite strands of a duplex to form a triplex on both strands of the duplex. The linker joining the regions of inverted polarity is a substitute linkage.

Oligomers. Oligomers are defined herein as two or more nucleomonomers covalently coupled to each other by a linkage or substitute linkage moiety. Thus, an oligomer can have as few as two nucleomonomers (a dimer). Oligomers can be binding competent and, thus, can base pair with cognate single-stranded or double-stranded nucleic acid sequences. oligomers (e.g. dimers-hexamers) are also useful as synthons for longer oligomers as described herein. oligomers can also contain abasic sites and pseudonucleosides.

Blocking Groups. As used herein, "blocking group" refers to a substituent other than H that is conventionally attached to oligomers or nucleomonomers, either as a protecting group, a coupling group for synthesis, $PO_3^{-2}$, or other conventional conjugate such as a solid support. As used herein, "blocking group" is not intended to be construed solely as a protecting group, according to slang terminology, but also includes, for example, coupling groups such as a hydrogen phosphonate or a phosphoramidite.

Protecting group. "Protecting group" as used herein means any group capable of preventing the O-atom or N-atom to which it is attached from participating in a reaction or bonding. Such protecting groups for O- and N-atoms in nucleomonomers are described and methods for their introduction are conventionally known in the art. Protecting groups also prevent reactions and bonding at carboxylic acids, thiols and the like.

Coupling group. "Coupling group" as used herein means any group suitable for generating a linkage or substitute linkage between nucleomonomers such as a hydrogen phosphonate and a phosphoramidite.

Conjugate. "Conjugate" as used herein means any group attached to the oligomer at a terminal end or within the oligomer itself. Conjugates include solid supports, such as silica gel, controlled pore glass and polystyrene; labels, such as fluorescent, chemiluminescent, radioactive, enzymatic moieties and reporter groups; oligomer transport agents, such as polycations, serum proteins and glycoproteins and polymers and the like.

Pi bond. "Pi bond" as used herein means an unsaturated covalent bond such as a double or triple bond. Both atoms can be carbon or one can be carbon and the other nitrogen, for example, phenyl, propynyl, cyano and the like.

Synthon. "Synthon" as used herein means a structural unit within a molecule that can be formed and/or assembled by known or conceivable synthetic operations.

Transfection. "Transfection" as used herein refers to any method that is suitable for enhanced delivery of oligomers into cells.

Subject. "Subject" as used herein means an animal, including a mammal, particularly a human.

DESCRIPTION OF THE INVENTION

Oligomers including either or both of the modified bases (1) or (2) show enhanced binding capacities in the formation of duplexes or triplexes with single-stranded RNA or DNA or duplex target sequences, respectively.

When the certain 5-substituted pyrimidines noted above are present, the additional nucleomonomer modifications can vary widely as discussed hereinafter. Preferably, the additional modification is at least one substitute linkage or a sugar modification such as a 2'-substituted deoxyribose.

The substitution of a base (1) or (2) of the invention, such as in 5-(1-alkenyl)-, 5-(1-alkynyl)-, 5-heteroaromatic- or 1-alkynyl-heteroaromatic substituted bases for thymine or cytosine in oligomers which target DNA duplexes provides binding competent oligomers with enhanced binding affinity. Substitution for thymine base residues by the 5-substituted uracil or thiouracil base residues of the invention or substitution for cytosine or 2-thiocytosine base residues by the 5-substituted cytosine base residues of the invention enhance the ability of the resulting oligomer to bind single-stranded DNA or RNA targets. In addition, some of the 5-substituted pyrimidine base residues significantly enhance triple helix formation with double stranded DNA.

For some $R^2$, substitution of 5-$R^2$ substituted U (5-$R^2$-U) for T in oligomers results in enhanced ability to form triplexes and duplexes as compared with the oligomers containing thymine. 5-$R^2$-U in these oligomers, in triplex formation recognizes adenine residues in adenine-thymine base pairs when hybridized in the parallel CT triplex motif. Oligomers having 8-oxo-$N^6$-methyladenine (a cytosine analog for triplex binding) and 5-$R^2$-U also bind in the CT motif. oligomers having 5-$R^2$-U and guanine are suitable for triplex binding to duplex sequences via the GT motif (5-$R^2$-U recognizes adenine). Some oligomers containing substitution of 5-R2 substituted C (5-$R^2$-C) in place of C bind duplex DNA, but not as well as control oligomers containing 5-methylcytosine at corresponding positions. The reduced efficiency of triplex formation is believed to result primarily from the reduced $pK_a$ of the substituted base. In the 5-propynyl-substituted nucleomonomer corresponding to the nucleomonomer containing 5-methylcytosine, the $pK_a$ is only 3.30.

The oligomers of the invention are thus capable of forming triplexes with various target sequences such as those found in oncogenes or viruses by binding in the major groove of a target DNA duplex under physiological pH conditions.

However, alteration of the heterocycle $pK_a$ as described above for the 5-$R^2$-C does not significantly affect binding to single-stranded target nucleic acid. In addition to binding efficiently to double-stranded target sequences, oligomers of the invention containing 5-$R^2$ substituted U in place of T and/or 5-$R^2$ substituted C in place of C were also found to bind single-stranded RNA efficiently. Oligomers containing either 5-$R^2$-C or 5-$R^2$-U formed duplex structures with complementary single-stranded RNA that had increased thermal stability ($T_m$) compared to the duplex formed by a control oligomer as described below.

Accordingly, in one aspect, the invention is directed to an oligomer comprising at least two and preferably, a multiplicity, of nucleomonomers wherein at least one said nucleomonomer comprises a base of formula (1) or (2) above.

Preferably, each X is O, i.e. formula (1) is uracil and formula (2) is cytosine. Other suitable pyrimidines include 4-thiouracil, 2-thiouracil, 2,4-dithiouracil and 2-thiocytosine.

In one embodiment of the invention $R^2$ is cyano, $C_{2-12}$ 1-alkenyl or 1-alkynyl or is a $C_{2-12}$ heteroaromatic group containing 5–6 ring atoms in which one to three of the ring atoms is N, S or O. Preferably, $R^2$ is a $C_{2-8}$ 1-alkenyl or 1-alkynyl or a $C_{2-8}$ heteroaromatic group containing 5–6 ring atoms in which one ring atom is N and optionally a second ring atom is N, S or O.

By "1-alkenyl" is meant an olefinically-unsaturated acyclic group, for example, vinyl, 1-propenyl, 1-butenyl optionally substituted by halogen or an alkynyl group.

By "1-alkynyl" is meant an acetylenically-unsaturated acylic group, such as ethynyl, 1-propynyl, 1-butynyl, 1-pentynyl, 1,3-pentadiynyl, and the like optionally substituted by an aryl or heteroaryl group, such as phenylethynyl, pyridine-ethynyl, pyrimidine-ethynyl, triazine-ethynyl, thiophene-ethynyl, thiazole-ethynyl and imidazole-ethynyl.

By "heteroaromatic" is meant a compound having at least one heterocyclic ring having physical and chemical properties resembling compounds such as an aromatic group of from 5 to 6 ring atoms and 2 to 12 carbon atoms in which one to three ring atoms is N, S or O, for example, 2-pyrimidinyl, 4-pyrimidinyl, 5-pyrimidinyl, 2-thiazoyl, triazinyl, 2-imidazolyl, 2-oxazolyl, 2-pyridinyl (o-pyridinyl), 3-pyridinyl (m-yridinyl), 4-pyridinyl (p-pyridinyl), 2-thienyl, 2-uranyl, 2-pyrrolyl optionally substituted preferably on ring C by oxygen, alkyl of 1–4 carbon atoms or halogen or on a ring N by alkyl of 1–4 carbon atoms. Preferred substituents on the heteroaryl group are methyl, ethyl, trifluoromethyl, and bromo.

Preferred oligomers contain one or more 5-$R^2$-U or 5-$R^2$-C bases.

In another embodiment of the invention, the oligomer comprises at least one base of formula (1) or (2) wherein each X is independently O or S; and $R^2$ is selected from the group consisting of phenylethynyl, 2-, 3-, and 4-pyridine-ethynyl, 2-, 4- and 5-pyrimidine-ethynyl, triazine-ethynyl, 2-, 4- and 5-pyrimidinyl, 2-, 4- and 5-thiazolyl, 1-methyl-2-imidazolyl, 2- and 4-imidazolyl, 2-, 4- and 5-oxazolyl, 3-pyridinyl, 4-pyridinyl, 2-pyridinyl, 2- and 3-furanyl-ethynyl, 2- and 3-thienyl-ethynyl, 2- and 4-imidazolyl-ethynyl, 2-, 4- and 5-thiazoyl-ethynyl, 2-, 4- and 5-oxazolyl-ethynyl, 2- and 3-pyrrolyl-ethynyl, 2- and 3-thienyl, 2- and 3-furanyl, 2- and 3-pyrrolyl, propenyl (—CH═CH—CH$_3$), vinyl and —C≡C—Z where Z is hydrogen (H) or $C_{1-10}$ alkyl, haloalkyl ($C_{1-10}$ with 1 to 6 halogen atoms or heteroalkyl ($C_{1-10}$ with 1 to 3 heteroatoms selected from the group consisting of O, N and S); and Pr is (H)$_2$ or a protecting group.

Examples of —C≡C-Z include 1-propynyl (—C≡C—CH$_3$), 3-buten-1-ynyl (—C≡C—CH═CH$_2$), 3-methyl-1-butynyl (—C≡C—CH(CH$_3$)$_2$), 3,3-dimethyl-1-butynyl (—C≡C—C(CH$_3$)$_3$), 1-butynyl (—C≡C—CH$_2$—CH$_3$), 1,3-pentadiynyl (—C≡C—C≡C—CH$_3$) and ethynyl.

Preferred halogens are selected from the group consisting of fluorine, chlorine and bromine. Substitutions including bromovinyl can be included in the oligomers.

Aspects of the invention include the use of nucleomonomers, two linked nucleomonomers (dimers), three linked nucleomonomers (trimers), four linked nucleomonomers (tetramers), five linked nucleomonomers (pentamers) or six linked nucleomonomers (hexamers) as intermediates in the synthesis of the longer oligomers of the invention. These oligomers are valuable synthons of the invention that are useful in the synthesis of longer oligomers.

In other aspects, the invention is directed to duplexes or triplexes obtained by binding the foregoing oligomers to single-stranded or duplex nucleic acid targets.

Other useful intermediates in the synthesis of the oligomers of the invention include an o-xyloso dimer having the structural formula (5),

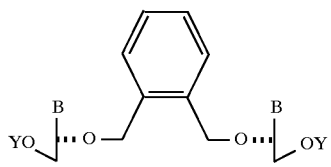

(5)

wherein each Y is independently an oligomer or $R^1$; and each B is independently a base provided that at least one B is a base of formula (1) or (2) wherein $R^2$ is as defined herein.

Also included are intermediates of the formula (6) shown in FIG. 1, wherein X is selected from the group consisting of O and S; and each Y, B, and $R^3$ is independently selected and has the meaning defined herein.

The oligomers of the invention are also suitable for binding to DNA duplex target sequences via either CT or GT triple helix binding motif.

The novel oligomers of the present invention are useful in antisense therapies wherein an oligomer hydridizes with a selected complementary RNA sequence or triple helix therapies wherein an oligomer hydridizes with a selected complementary DNA sequence.

The invention is also directed to an oligomer of the invention comprising a positive modification of least one base of formula (1) or (2) of the invention and a negative modification, each with respect to the binding affinity of the oligomer to a complementary nucleic acid sequence. The positive modification counteracts the effect of the negative modification to a degree that is more than additive with respect to the binding affinity, thus a synergistic effect is observed.

An aspect of the invention is the inclusion of the invention bases in oligomers that are resistant to nuclease degradation relative to an oligodeoxynucleotide having no modifications. Nuclease resistant oligomers of the invention are advantageously used under conditions where nucleases are present. For certain applications, such as modulation of gene expression by via an antisense mechanism, nuclease stability by oligomers of the invention is an important functional aspect of the oligomer.

Other aspects of the invention are directed to pharmaceutical compositions, reagents and kits comprising the oligomers of the invention, to methods of treating conditions, such as cancers and viruses or the like. Such conditions are associated with or characterized by particular nucleic acids such as DNA duplexes or single-stranded RNA or DNA.

An additional aspect of the invention includes methods of detecting the presence, absence or amount of a particular single-stranded DNA or RNA or a particular target duplex in a biological (or other) sample using the oligomers of the invention, to detect selected nucleic acid sequences. Such sequences can be associated with the presence of neoplastic growth, viruses or disease conditions. Reagents and kits containing oligomers of the invention represent an aspect of the invention that permit facile use of the oligomers as reagents useful for (1) modulating gene expression in cells in vitro including cells grown in tissue culture, and (2) detecting and/or quantitating target sequences.

It has been found that some of the oligomers of the invention have enhanced binding properties with respect to complementary single-stranded and double-stranded nucleic acid sequences as compared to unmodified oligomers not having the 5-substitution of the invention. Triple helix structures can be formed at physiological pH levels of 7.0 and higher, where unmodified control oligomers were less efficient. Improved duplex formation is also noted.

A feature of the invention is that the oligomers of the invention can be comprised of a variety of different sequences and thereby used to target a variety of different single-stranded or double-stranded target sequences.

An advantage of the present invention is that he oligomers of the invention are capable of forming riplexes under physiological pH conditions.

Another feature of oligomers containing 5-$R^2$ substituted uracil or cytosine base (1) or (2) of the invention compared to oligomers containing thymine or cytosine is that the lipophilic group ($R^2$) can enhance cell permeation or uptake. The nucleomonomers containing these bases are more lipophilic than uridine, cytidine or thymidine based on retention times on reverse phase HPLC.

Additional Nucleomonomer Modifications.

Oligomers that are comprised of nucleomonomers can also contain modifications in addition to the 5-modified pyrimidines of the invention. A non-limiting exemplary list of such additional modifications includes oligomers where (i) one or more nucleomonomer residues are modified at the 2' position, (ii) one or more covalent crosslinking moieties are incorporated, (iii) inverted polarity linkers are incorporated, (iv) substitute linkages are included, (v) other base analogs, such as 8-oxo-$N^6$-methyladenine, are included and (vi) conjugates such as intercalating agents or polylysine that respectively enhance binding affinity to target nucleic acid sequences or that enhance association of the oligomer with cells are included.

The ability of the 5-substitution of the bases (1) and (2) of the invention to enhance affinity of the oligomer for single-stranded and duplex targets (positive modification) permits further modifications to the oligomer in which they are contained. These further modifications may or may not diminish affinity, but also confer other useful properties such as stability to nuclease cleavage, ability to permeate cell membranes, and the like. Any decrease in binding affinity resulting from the further modifications (negative modification) is acceptable because of the enhanced affinity conferred by the 5-substituted bases (1) and (2). Thus, particularly preferred oligomers of the invention can contain substitute linkages and/or modified sugars, as well as the 5-substituted pyrimidine bases (1) and (2) of the invention.

The oligomers can also contain additional modifications in the nucleomonomers that contain these 5-modified pyrimidines or in other nucleomonomers that comprise the oligomer.

Also included are oligomers containing one or more substitute linkages such as sulfide or sulfone linkages (Benner, S. A., International Publication No. WO 89/12060), sulfamate linkages (International Publication No. WO 91/15500), carbamate linkages in morpholino-linked oligomers (Stirchak, E. P. et al *Nucleic Acids Res* (1989) 17:6129–6141) and related linkages in morpholino oligomers of the formula (7) shown in FIG. 1 wherein $X^2$ is Co, CS or $SO_2$; $X^3$ is O, S, NH, $NCH_3$, $CH_2$, $CF_2$ or CHF; each Y is independently an oligomer or $R^1$ and each B is independently chosen and has the previously defined meaning, provided that at least one B is a base of formula (1) or (2).

Riboacetal and related linkages, amide linkages and 2',5' linkages are described in commonly owned pending U.S. application Ser. Nos. 07/806,710, filed Dec, 12, 1991, 07/899,736, filed Can 28, 1992, 07/894,397 and filed 07/892,902, filed each cited reference is incorporated herein by reference.

Figure 2:
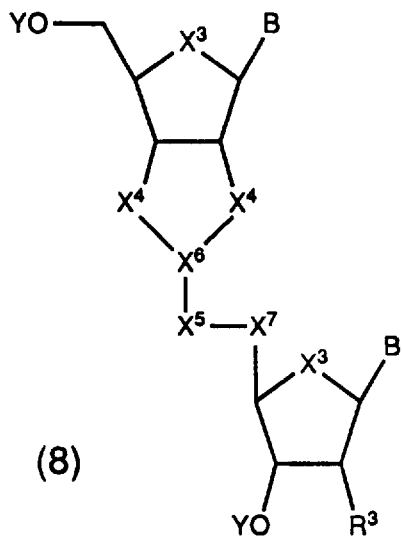
FIG. 2. Dimer synthons containing bases of the invention and containing 5 and 6 membered riboacetal type linkages.
Figure 2:
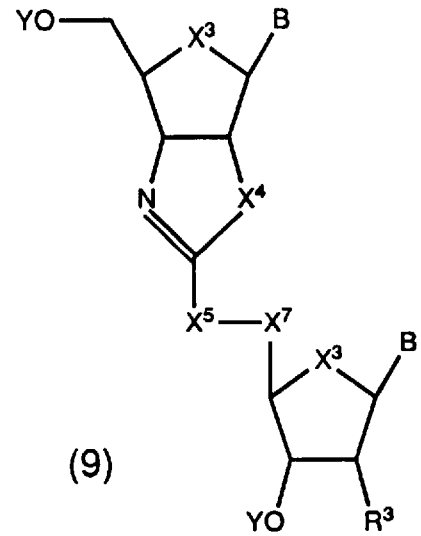
Figure 2:
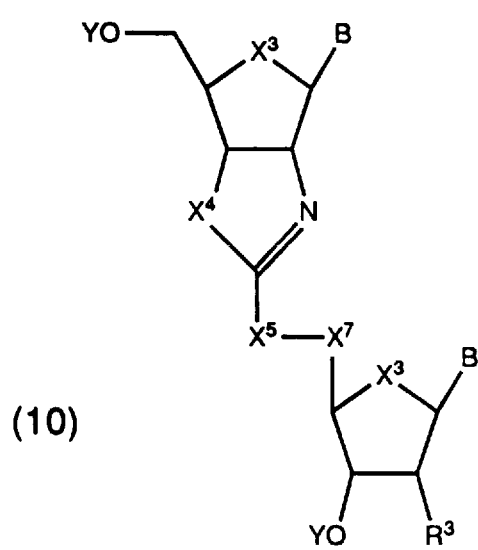
Figure 2:
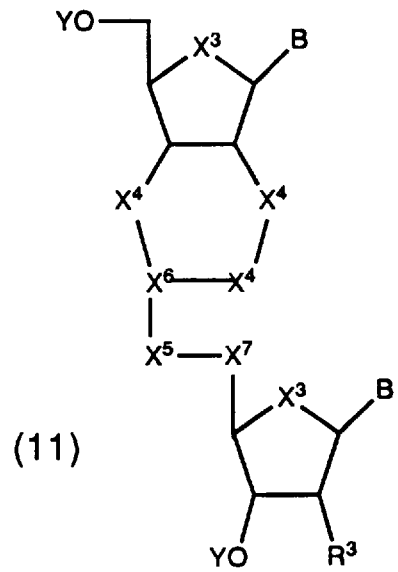
Figure 3:
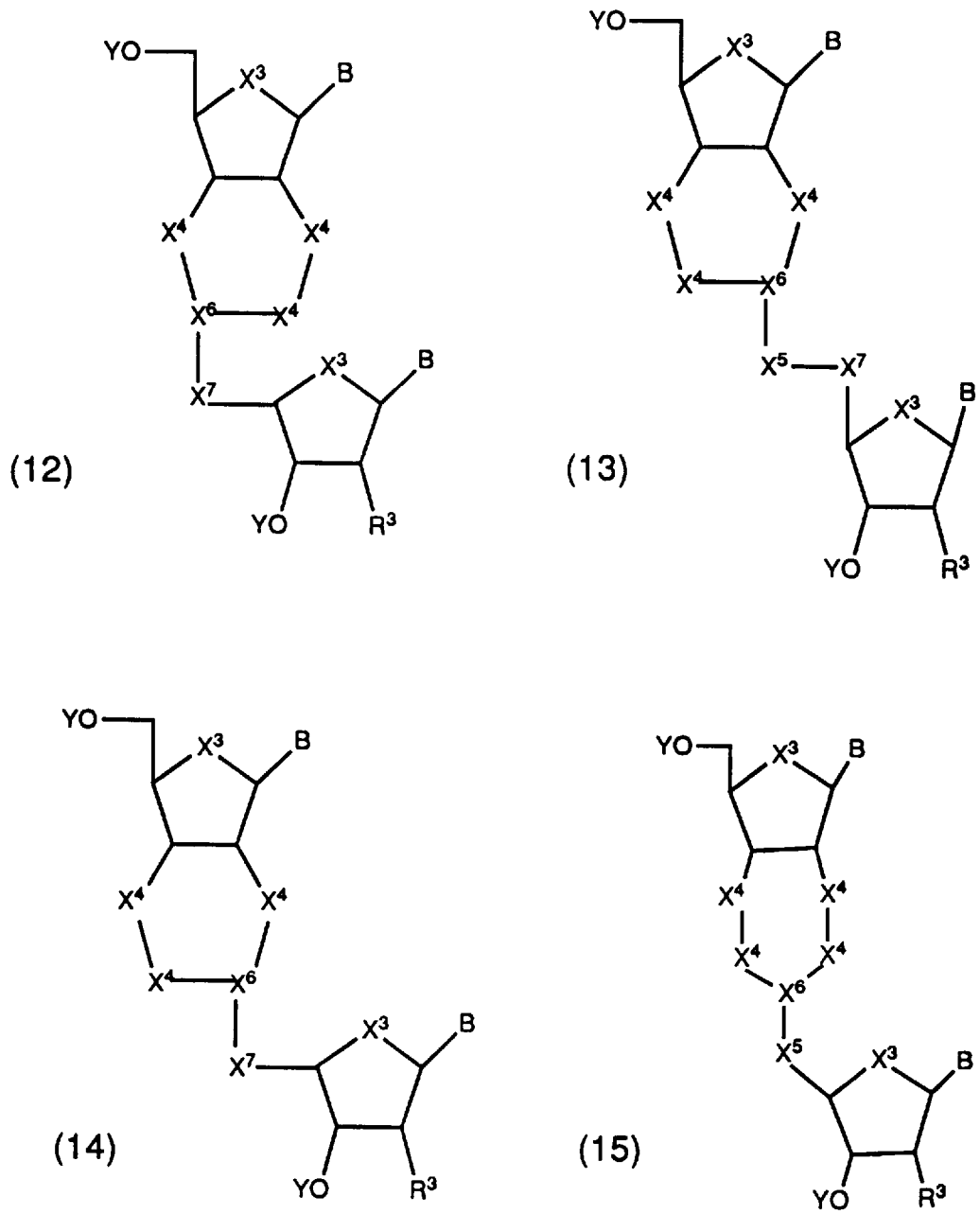
FIG. 3. Dimer synthons containing bases of the invention and containing 6 and 7 membered riboacetal type linkages.

Exemplary dimers containing riboacetal and related linkages of formulae (8–15) are shown in FIGS. 2 and 3 wherein for each structure, $R^1$ and B are independently chosen and have the meanings defined above;

$R^3$ has the meaning as defined above;

$X^3$ is independently selected from the group consisting of O, S, NH, $NCH_3$, $CH_2$, $CF_2$ and CFH;

$X^4$ is independently selected from the group consisting of O, S, SO, $SO_2$, $CH_2$, CO, $CF_2$, CS, NH and $NR^4$ wherein $R^4$ is lower alkyl ($C_{1-4}$; methyl, ethyl, propyl, isopropyl, butyl or isobutyl); $X^5$ is selected from the group consisting of O, CO, S, $CH_2$, CS, NH and $NR^4$;

$X^6$ is selected from the group consisting of CH, N, CF, CCl, and $CR^5$ wherein $R^5$ is methyl or lower alkyl ($C_{2-4}$) fluoromethyl, difluoromethyl, trifluoromethyl or lower fluoroalkyl ($C_{2-4}$, $F_{1-5}$);

$X^7$ is selected from the group consisting of O, S, $CH_2$, CO, $CF_2$ and CS, provided that at least one B is of the formula (1) or (2) as defined above; and further provided that no adjacent $X^4$, $X^5$ or $X^7$ are O (i.e., —O—O—, a peroxide).

Compounds of the 5-member ring series are preferred embodiments for oligomers containing one or more riboacetal linkages (formula (8)), where $X^4$ is O and $X^5$, $X^7$ are $CH_2$ and $X^6$ is CH.

Also included are oligomers containing nucleomonomer residues linked via amide bonds. Exemplary linkages have been described (Nielsen, P. E., et al, *Science* (1991) 254:1497–1500; commonly owned copending U.S. application Ser. Nos. 07/889,736, filed Can 28, 1992, and 07/894, 397, filed Jun. 5, 1992, both incorporated herein by reference).

Oliqomers

As used herein "oligomer" includes oligonucleotides, oligonucleosides, polydeoxyribo-nucleotides (containing 2'-deoxy-D-ribose or modified forms thereof), i.e., DNA, polyribonucleotides (containing D-ribose or modified forms thereof), i.e., RNA, and any other type of polynucleotide which is an N-glycoside or C-glycoside of a purine or pyrimidine base, or modified purine or pyrimidine base. Oligomer as used herein is also intended to include compounds where adjacent nucleomonomers are linked via amide linkages as previously described (Nielsen, P. E., et al, *Science* (1991) 254:1497–1500). The enhanced competence of binding by oligomers containing the bases of the present invention is believed to be primarily a function of the base alone. Because of this, elements ordinarily found in oligomers, such as the furanose ring and/or the phosphodiester linkage can be replaced with any suitable functionally equivalent element. "Oligomer" is thus intended to include any structure that serves as a scaffold or support for the bases wherein the scaffold permits binding to target nucleic acids in a sequence-dependent manner. Oligomers that are currently known can be defined into four groups that can be characterized as having (i) phosphodiester and phosphodiester analog (phosphorothioate, methylphosphonate, etc) linkages, (ii) substitute linkages that contain a non-phosphorous isostere (formacetal, riboacetal, carbamate, etc), (iii) morpholino residues, carbocyclic residues or other furanose sugars, such as arabinose, or a hexose in place of ribose or deoxyribose and (iv) nucleomonomers linked via amide bonds or acyclic nucleomonomers linked via any suitable substitute linkage.

The oligomers of the invention can be formed using invention and conventional nucleomonomers and synthesized using standard solid phase (or solution phase) oligomer synthesis techniques, which are now commercially available. In general, the invention oligomers can be synthesized by a method comprising the steps of: synthesizing a nucleomonomer or oligomer synthon having a protecting group and a base and a coupling group capable of coupling to a nucleomonomer or oligomer; coupling the nucleomonomer or oligomer synthon to an acceptor nucleomonomer or an acceptor oligomer; removing the protecting group; and repeating the cycle as needed until the desired oligomer is synthesized.

The oligomers of the present invention can be of any length including those of greater than 40, 50 or 100 nucleomonomers. In general, preferred oligomers contain 2–30 nucleomonomers. Lengths of greater than or equal to about 8 to 20 nucleomonomers are useful for therapeutic or diagnostic applications. Short oligomers containing 2, 3, 4 or 5 nucleomonomers are specifically included in the present invention and are useful as synthons.

Oligomers having a randomized sequence and containing about 6 or 7 nucleomonomers are useful for primers that are used in cloning or amplification protocols that use random sequence primers, provided that the oligomer contains residues that can serve as a primer for polymerases or reverse transcriptases.

Figures 1, 12:
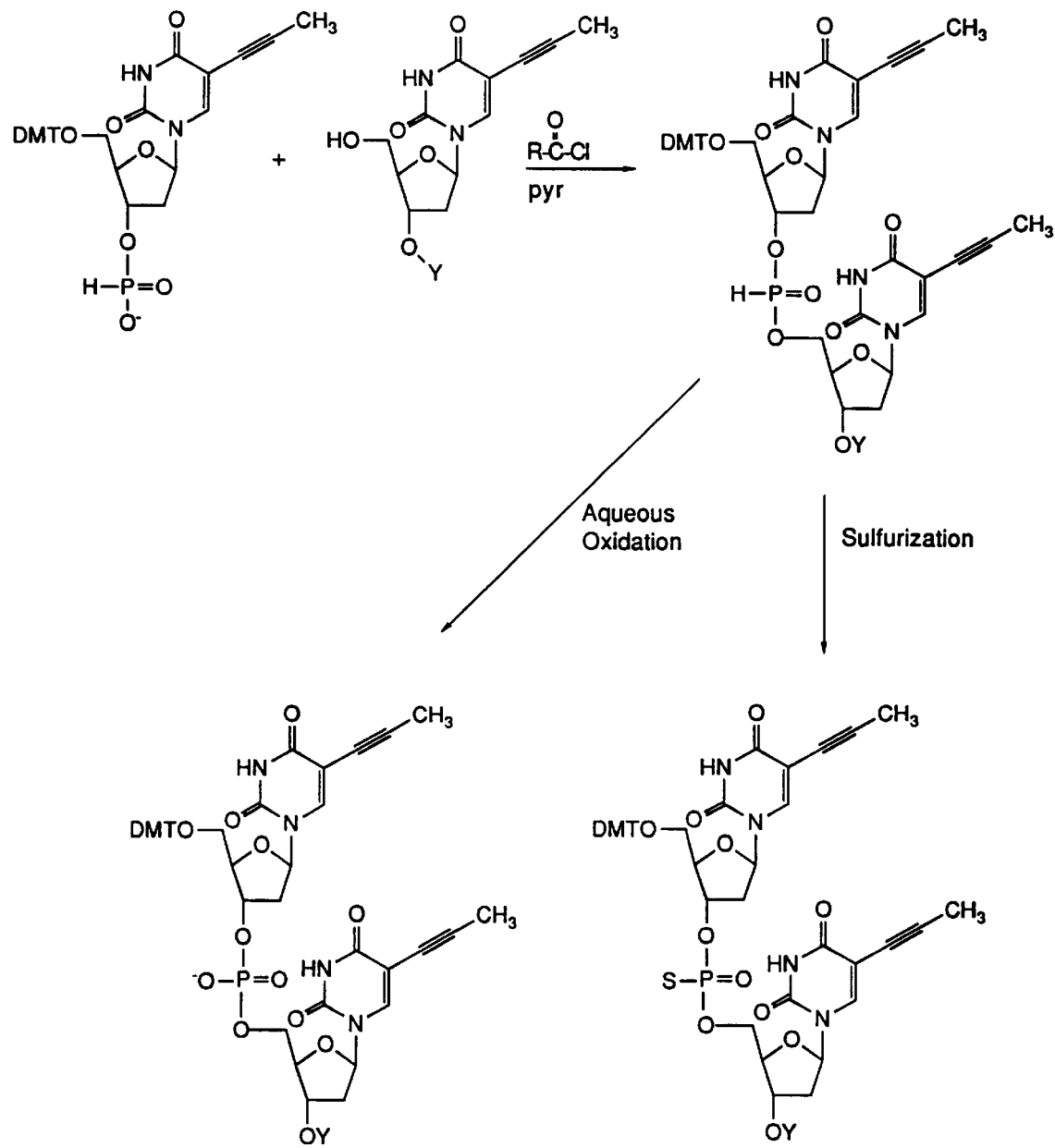
FIG. 12.
Figures 2, 12:
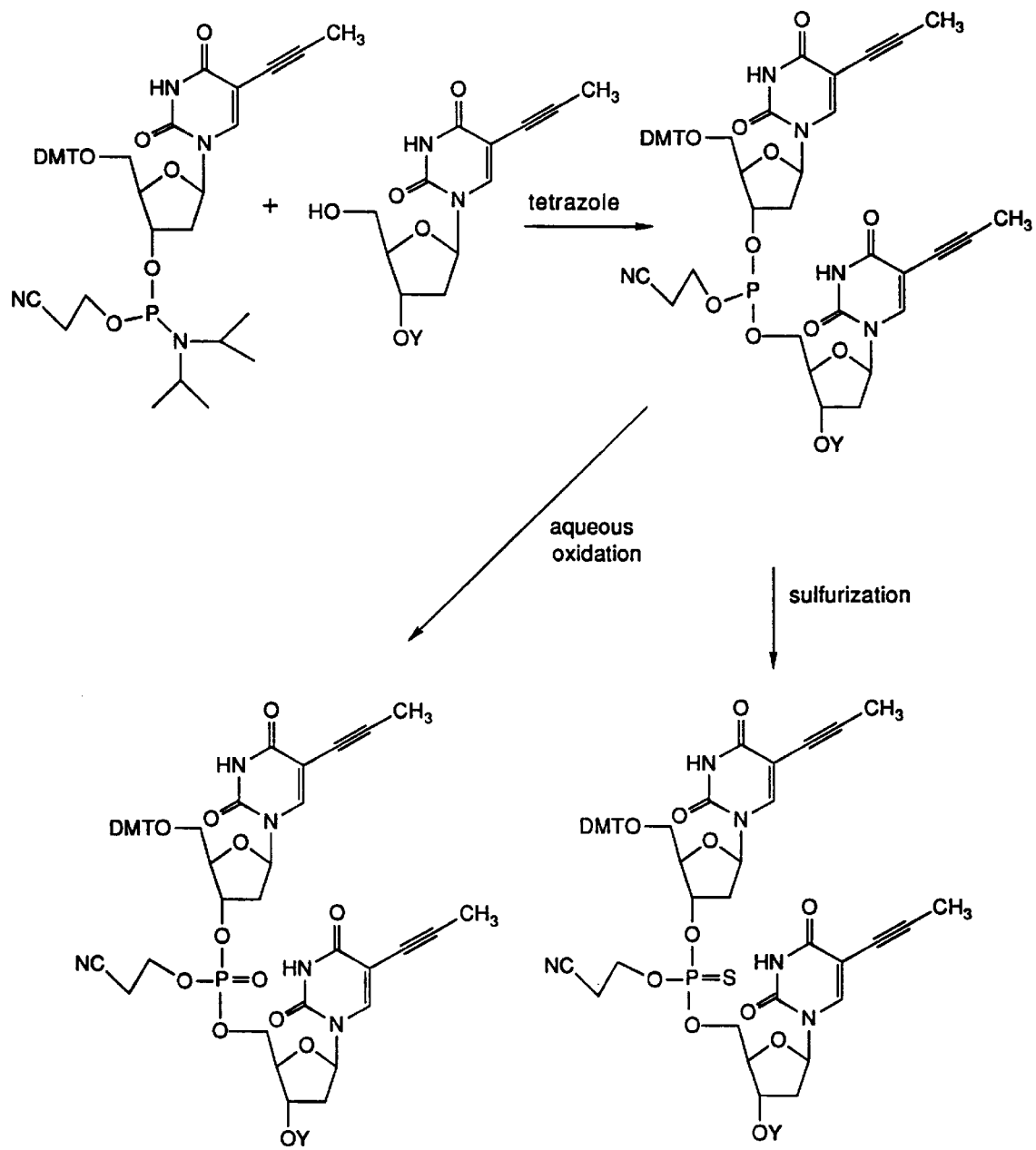
Figures 3, 12:
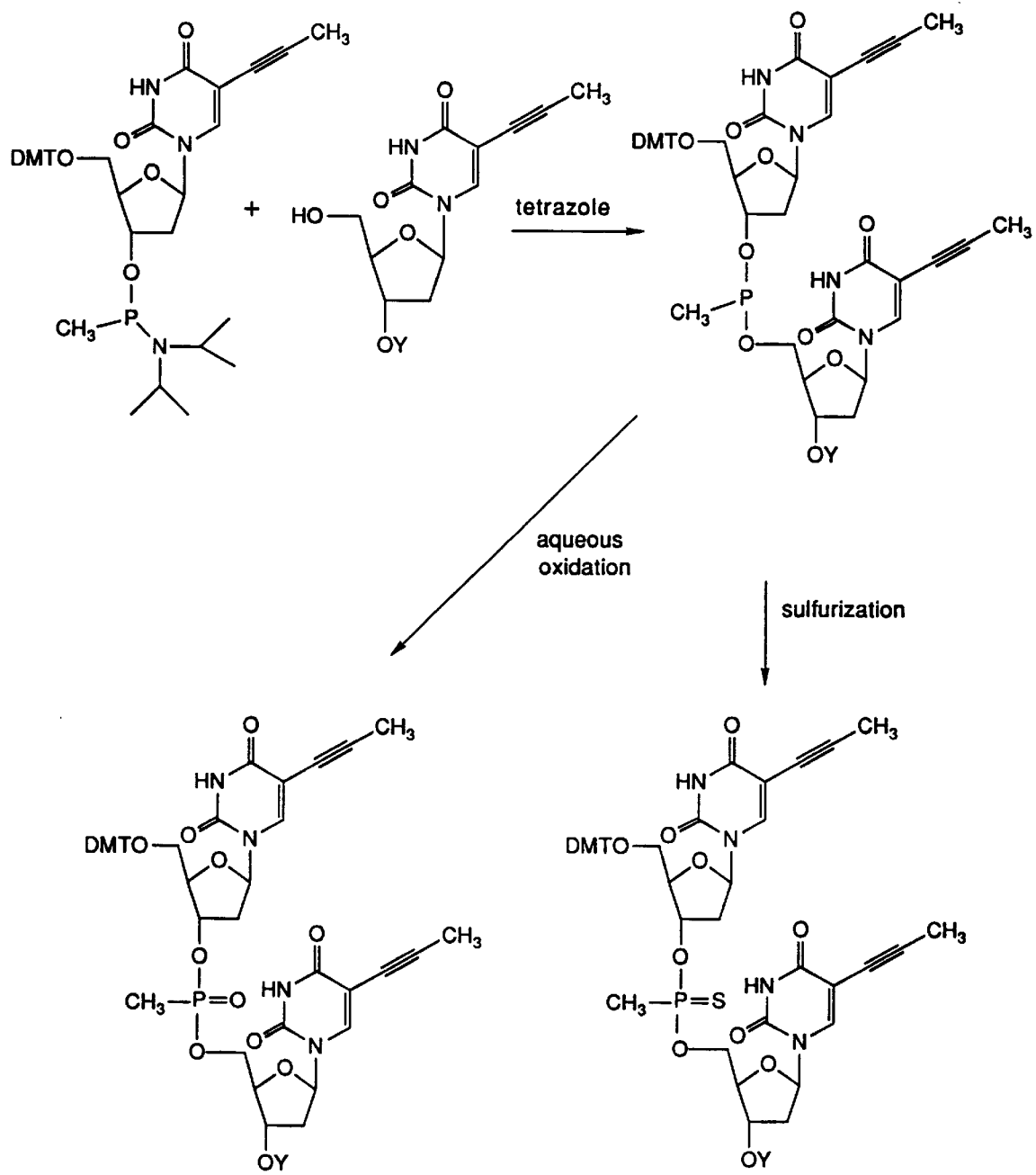
Figure 13:
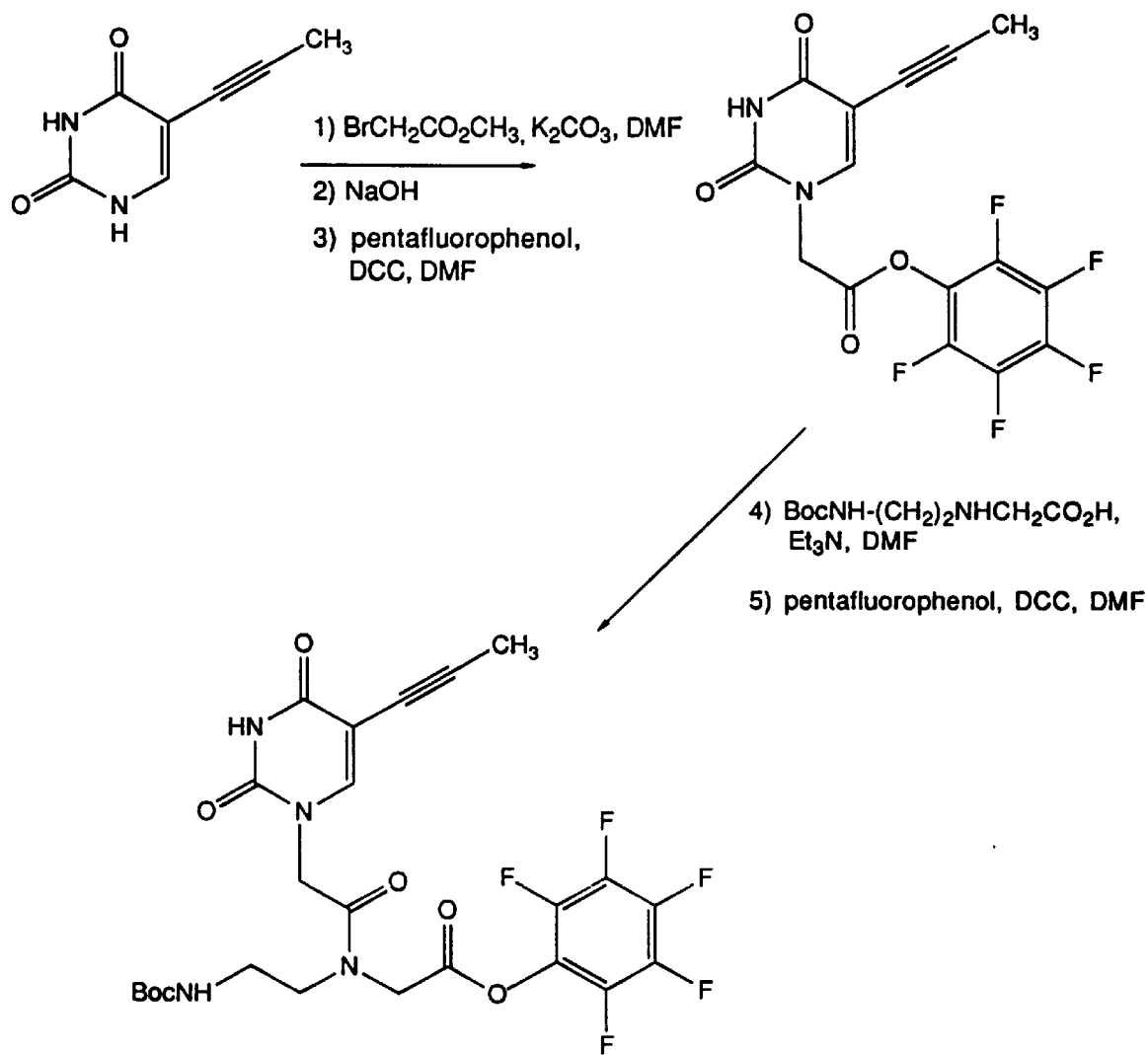
FIG. 13. Synthesis of a monomer for an oligomer containing amide linkages (method #4).

Oligomers can contain conventional phosphodiester linkages or can contain substitute linkages such as phosphoramidate linkages. These substitute linkages include, but are not limited to, embodiments wherein a moiety of the formula —O—P(O)(S)—O— ("phosphorothioate"), —O—P(S)(S)—O— ("phosphorodithioate"), —O—P(O)(NR'$_2$)—X—, —O—P(O)(R')—O—, —O—P(S)(R')—O— ("thionoalkylphosphonate"), —P(O)(OR$^6$)—X—, —O—C(O)—X—, or —O—C(O)(NR'$_2$)—X—, wherein R' is H (or a salt) or alkyl (1–12C) and R$^6$ is alkyl (1–9C) and the linkage is joined to adjacent nucleomonomers through an —O— or —S— bonded to a carbon of the nucleomonomer. Phosphorothioate and phosphodiester linkages are shown in FIG. 12. Particularly, preferred substitute linkages for use in the oligomers of the present invention include phosphodiester, phosphorothioate, methylphosphonate and thionomethylphosphonate linkages. Phosphorothioate and methylphosphonate linkages confer added stability to the oligomer in physiological environments. While not all such linkages in the same oligomer need be identical, particularly preferred oligomers of the invention contain uniformly phosphorothioate linkages or uniformly methylphosphonate linkages.

Pharmaceutically Acceptable Salts

Any pharmaceutically acceptable salt can be used and such salt forming materials are well known in the art.

Pharmaceutically acceptable salts are preferably metal or ammonium salts of said oligomers of the invention and include alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amides, lower alkylenediamines or lower (hydroxyalkyl or arylalkyl)-alkylammonium bases, e.g. ethylamine, diethylamine, triethylamine, dicyclohexylamine, triethanolamine, ethylenediamine, tris-(hydroxymethyl)-aminomethane or benzyl-trimethylammonium hydroxide. The oligomers of the invention form acid addition salts, which are preferably such of therapeutically acceptable inorganic or organic acids, such as strong mineral acids, for example hydrohalic, e.g., hydrochloric or hydrobromic acid; sulfuric, phosphoric; aliphatic or aromatic carboxylic or sulfonic acids, e.g., formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-amino salicylic, methanesulfonic, ethanesulfonic, hydroxy ethanesulfonic, benzenesulfonic, sulfanilic or cyclohexyl-sulfamic acid and the like.

Blocking Groups

As used herein, "blocking group" refers to a substituent other than H that is conventionally coupled to oligomers or nucleomonomers, either as a protecting group, a coupling group for synthesis, pO$_3^{-2}$, or other conventional conjugate such as a solid support, label, antibody, monoclonal antibody or fragment thereof and the like. As used herein, "blocking group" is not intended to be construed solely as a protecting group, according to slang terminology, but is meant also to include, for example, coupling groups such as a H-phosphonate or a phosphoramidite.

By "protecting group" is meant is any group capable of protecting the O-atom or N-atom to which it is attached from participating in a reaction or bonding. Such protecting groups for N-atoms on a base moiety in a nucleomonomer and their introduction are conventionally known in the art. Non-limiting examples of suitable protecting groups include diisobutylformamidine, benzoyl and the like. Suitable "protecting groups" for O-atoms are, for example, DMT, MMT, or FMOC.

Figure 10:
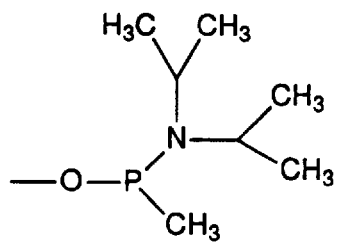
FIG. 10.
Figure 4:
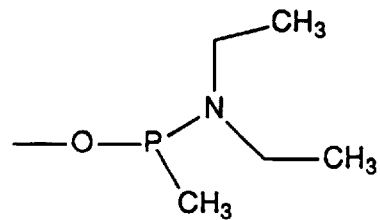

Suitable coupling groups are, for example, H-phosphonate, a methylphosphonamidite, or a phosphoramidite. Phosphoramidites that can be used include β-cyanoethylphosphoramidites (preferred). Methylphosphonamidites, alkylphosphonamidites (including ethylphosphonamidites and propylphosphonamidites) can also be used. Exemplary phosphoramidites are shown in FIGS. 10-1 and 10-2.

Suitable protecting groups are DMT (dimethoxy trityl), MMT (monomethoxytrityl) or FMOC at the 5' terminus and/or hydrogen phosphonate, methyl phosphoramidite, methyl phosphonamidite, β-cyanoethylphosphoramidite at the 3'-terminus.

Protecting Groups

Protecting groups such as diisobutylformamidine, benzoyl, isobutyryl, FMOC, dialkylformamidine, dialkylacetamidine or other groups known in the art can be used to protect the exocyclic nitrogen of the cytosine heterocycle. Alternatively, cytidine precursors can be directly incorporated into oligomers without a protecting group at the exocyclic nitrogen using described methods (Gryaznov, S. M. et al, *J Amer Chem Soc* (1991) 113:5876–5877; Gryaznov, S. M., et al, *Nucl Acids Res* (1992) 20:1879–1882; Kung, P.-P., et al, *Tetrahedron Letters* (1992) 40:5869–5872). Synthesis of oligomers having bases (1) or (2) containing an R$^2$ as ethynyl heteroaryl substituents is preferably accomplished using 9-fluorenylmethoxycarbonyl (FMOC) for protection of the 5'-hydroxyl position as described (Lehman, C., et al, *Nucl Acids Res* (1989) 17:2379–2390).

Preferred protecting groups are DMT (dimethoxy trityl), MMT (monomethoxytrityl) or FMOC at the 5' terminus and/or hydrogen phosphonate, methyl phosphoramidite, methyl phosphonamidite, β-cyanoethylphosphoramidite at the 3'-terminus. However, it is intended that the position of the blocking groups can be reversed as needed (e.g., a phosphoramidite at the 5'-position and DMT at the 3'-position). In general, the nucleomonomers and oligomers of the invention can be derivatized to such "blocking groups" as indicated in the relevant formulas by methods known in the art.

Coupling Groups

Suitable coupling groups are, for example, H-phosphonate, a methylphosphonamidite, or a phosphoramidite. Phosphoramidites that can be used include β-cyanoethylphosphoramidites (preferred). Methylphosphonamidites, alkylphosphonamidites (including ethylphosphonamidites and propylphosphonamidites) can also be used. Exemplary phosphoramidites are shown in FIGS. 10-1 and 10-2. Suitable "coupling groups" at the 3', 2' or 5' position for oligomer synthesis via phosphoramidite triester chemistry, referred to herein as "amidite" chemistry, include N,N-diisopropylamino-β-cyanoethoxyphosphine, N,N-diisopropylamino-methoxyphosphine, N,N-diethylamino-β-cyanoethoxyphosphine, (N-morpholino)-β-cyanoethoxyphosphine, and (N-morpholino)-methoxyphosphine (Moore, M. F. et al, *J Ora Chem* (1985) 50:2019–2025; Uznanski, A. W., et al, *Tet Lett* (1987) 28:3401–3404; Bjergarde, K., et al, *Nucl Acids Res* (1991)

Figures 1, 4:
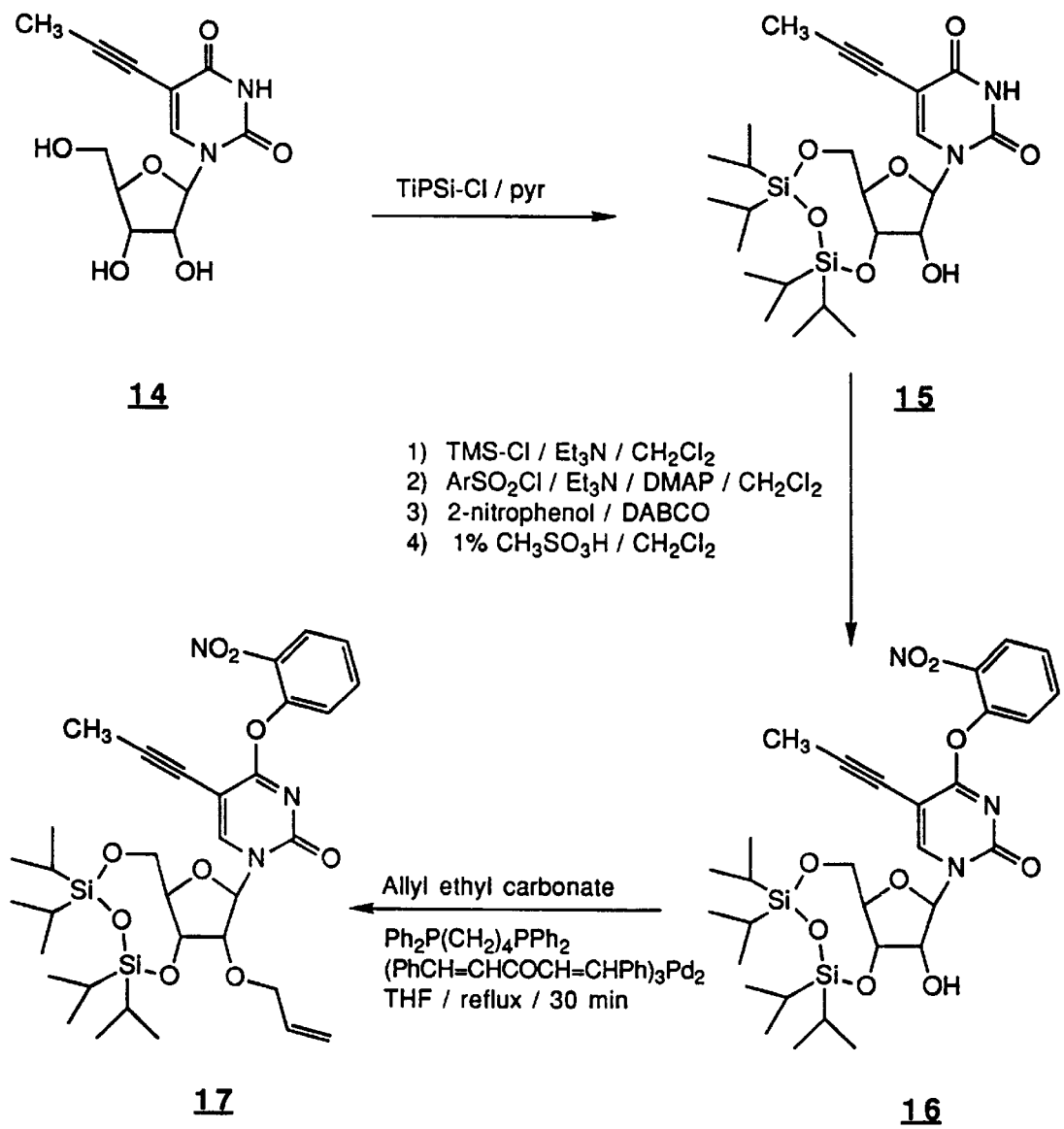
FIG. 4.
Figures 2, 4:
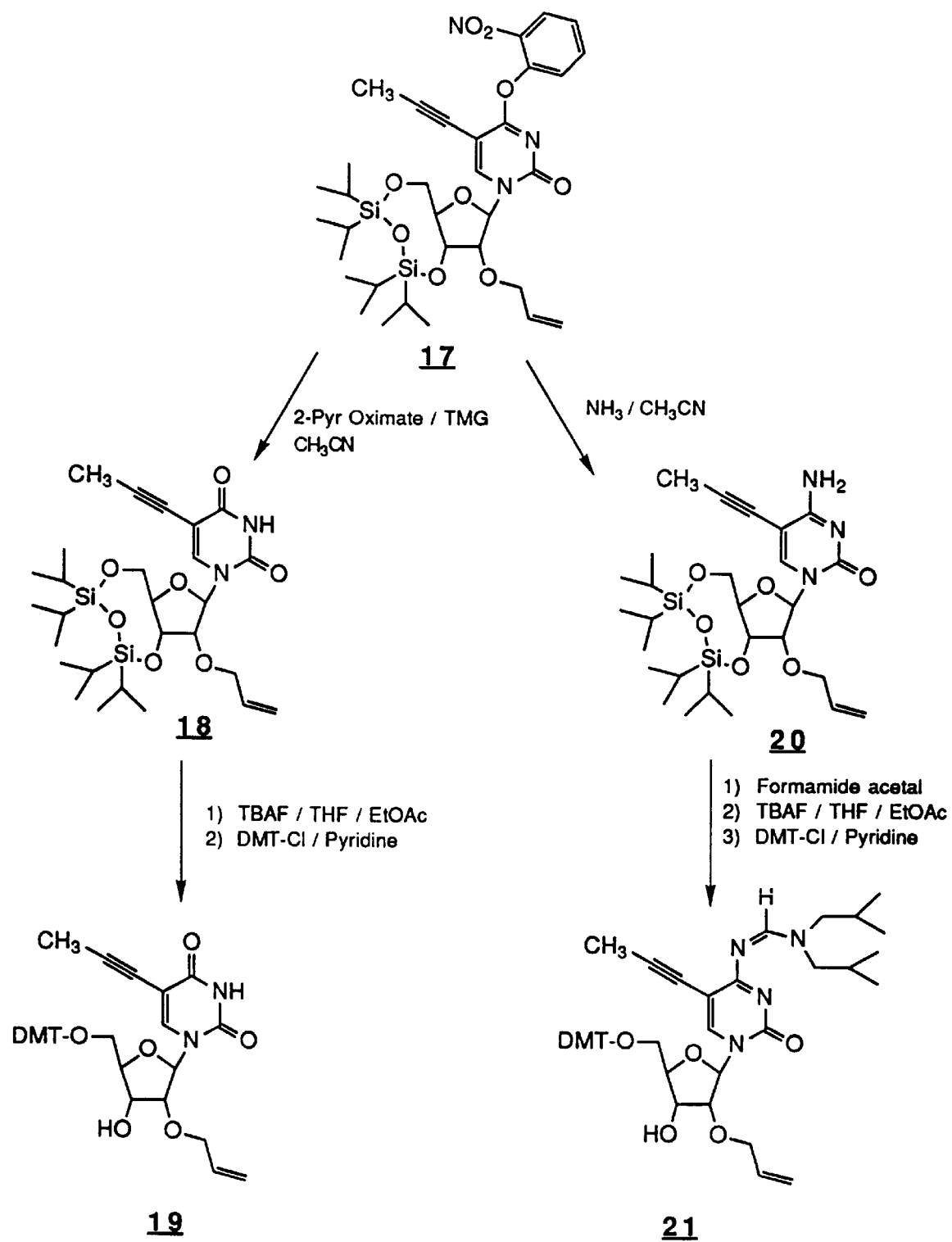

21:5843–5850; Dahl, O. *Sulfur Reports* (1991) 11:167–192). Related coupling groups such as U,N-diisopropylamino-methyl-phosphine or N,N-diethylamino-methyl-phosphine can also be used to prepare methylphosphonates (FIG. 10-4). Methylphosphonate oligomers can be conveniently synthesized using coupling groups such as N,N-diisopropylamino-methylphosphonamidite, and N,N-diethylamino-methylphosponamidite. Synthesis of nucleomonomer amidites of the invention can be accomplished by conventional methods (for example, Gryaznov, S. M., et al, *Nucl Acids Res* (1992) 20:1879–1882; Vinayak, R., et al, *Nucl Acids Res* (1992) 20:1265–1269; Sinha, N. D., et al, *Nucl Acids Res* (1984) 12:4539–4557; and other references cited herein). Suitable coupling groups at the 3', 2' (or 5') position for oligomer synthesis via phosphate triester chemistry, referred to herein as "triester" chemistry, include 2-chlorophenyl phosphate, 4-chlorophenyl phosphate, 2,4-dichlorophenyl phosphate and 2,4, -dibromophenyl phosphate nucleotide diester derivatives or, for synthesis of phosphorothioate linkages, the thiono derivatives thereof (Marugg, J. E., et al, *Nucl Acids Res* (1984) 12:9095–9110; Kemal, O., et al, *J Chem Soc Chem Commun* (1983) 591–593; Kamer, P. C. J., et al, *Tet Lett* (1989) 30:6757–6760). Structures of these coupling groups are shown in FIG. 10 where X is O or S and $Z^1$ is H or a suitable benzotriazole.

Oligomers or the segments thereof are conventionally synthesized. The synthetic methods known in the art and described herein can be used to synthesize oligomers containing bases of the invention, as well as other bases known in the art, using appropriately protected nucleomonomers (see FIG. 12). Methods for the synthesis of oligomers are found, for example, in Froehler, B., et al., *Nucleic Acids Res* (1986) 14:5399–5467; *Nucleic Acids Res* (1988) 16:4831–4839; *Nucleosides and Nucleotides* (1987) 6:287–291; Froehler, B., *Tetrahedron Letters* (1986) 27:5575–5578; Caruthers, M. H. in *Oliaodeoxvnucleotides-Antisense Inhibitions of Gene Expression* (1989), J. S. Cohen, editor, CRC Press, Boca Raton, p7–24; Reese, C. B. et al, *Tetrahedron Letters* (1985) 26:2245–2248. Synthesis of the methylphosphonate linked oligomers via methyl phosphonamidite chemistry has also been described (Agrawal, S. et al., *Tetrahedron Letters* (1987) 28:3539–3542; Klem, R. E., et al, International Publication Number WO 92/07864).

Conjugates

Also included are "conjugates" of oligomers. "Conjugates" of the oligomers include those conventionally recognized in the art. For instance, the oligomers can be covalently linked to various moieties such as, intercalators, and substances which interact specifically with the minor groove of the DNA double helix. Other chosen conjugate moieties, can be labels such as radioactive, fluorescent, enzyme, or moieties which facilitate cell association using cleavage linkers and the like. Suitable radiolabels include $^{32}P$, $^{35}S$, $^3H$ and $^{14}C$; and suitable fluorescent labels include fluorescein, resorufin, rhodamine, BODIPY (Molecular Probes) and texas red; suitable enzymes include alkaline phosphatase and horseradish peroxidase. Other compounds which can be used as covalently linked moieties include biotin, antibodies or antibody fragments, transferrin and the HIV Tat protein can also conveniently be linked to the oligomers of the invention.

These additional moieties can be derivatized through any convenient linkage. For example, intercalators, such as acridine or psoralen can be linked to the oligomers of the invention through any available —OH or —SH, e.g., at the terminal 5'-position of the oligomer, the 2'-positions of RNA, or an OH, $NH_2$, COOH or SH incorporated into the 5-position of pyrimidines. A derivatized form which contains, for example, —$CH_2CH_2NH_2$, —$CH_2CH_2CH_2OH$ or —$CH_2CH_2CH_2SH$ in the 5-position is preferred. Conjugates including polylysine or lysine can be synthesized as described and can further enhance the binding affinity of an oligomer to its target nucleic acid sequence (Lemaitre, M. et al., *Proc Natl Acad Sci* (1987) 84:648–652; Lemaitre, M. et al., *Nucleosides and Nucleotides* (1987) 6:311–315).

A wide variety of substituents can be attached, including those bound through linkages or substitute linkages. The —OH moieties in the oligomers can be replaced by phosphate groups, protected by standard protecting groups, or coupling groups to prepare additional linkages to other nucleomonomers, or can be bound to the conjugated substituent. The 5'-terminal OH can be phosphorylated; the 2'-OH or OH substituents at the 3'-terminus can also be phosphorylated. The hydroxyls can also be derivatized to standard protecting groups.

Oligomers of the invention can be covalently derivatized to moieties that facilitate cell association using cleavable linkers. Linkers used for such conjugates can include disulfide linkages that are educed after the oligomer-transport agent conjugate has entered a cell. Appropriate molecular linkers include for example, —$Y^1$—$X^8CH_2CHR^7$—SS—$CHR^7CH_2X^8$—$Y^1$— wherein each $Y^1$ is independently alkylene ($C_{1-6}$; including methylene, ethylene and propylene), or CO, each $X^8$ is independently O, S(O)(O), S(O), $NR^7$, $CH_2$, $C(R^7)_2$ or CO; $R^7$ wherein each $R^7$ is independently H, alkyl ($C_{1-6}$; including methyl, ethyl and propyl), or aryl and which linkers have been previously described (WO 91/14696). Disulfide-containing linkers of this type have a controllable $t_{1/2}$ in vivo, facilitating its use as a prodrug/transport component. Such linkers are stable under extracellular conditions relative to intracellular conditions due to the redox potential of the disulfide linkage.

Suitable conjugates also include solid supports for oligomer synthesis and to facilitate detection of nucleic acid sequences. Solid supports included, but are not limited to, silica gel, controlled pore glass, polystyrene, and magnetic glass beads.

Sugar Modifications.

Derivatives can be made by substitution on the sugars. Among the most preferred derivatives of the oligomers of the invention are the 2'-O-allyl derivatives. The presence of the 2'-O-allyl group appears to enhance permeation ability and stability to nuclease degradation, but does not appear to diminish the affinity of the oligomer for single chain or duplex targets.

Furthermore, as the α anomer binds to duplex DNA or single-stranded RNA in a manner similar to that for the β anomers but with a reversed polarity, oligomers can contain nucleomonomers having this epimer or a domain thereof (Praseuth, D., et al., *Proc Natl Acad Sci* (USA) (1988) 85:1349–1353; Sun, J. S. et al, *Proc Natl Acad Sci* (1991) 88:6023–6027; Debart, F., et al, *Nucl Acids Res* (1992) 20:1193–1200). α-Anomeric oligomers containing the 5-$R^2$ substituted pyrimidines described herein represent a class of modified oligomers included in the present invention.

Substitute Linkages

The oligomers of the invention can also contain one or more "substitute linkages" as is generally understood in the art. These "substitute linkages" include phosphorothioate, methylphosphonate, thionomethylphosphonate, phosphorodithioate, riboacetal, 2', 5' linkages, alkylphosphonates, morpholino carbamate, morpholino sulfamate, morpholino sulfamide, boranophosphate (—O—P(OCH$_3$)(BH$_3$)—O—), siloxane (—O—Si (X$^4$)(X$^4$)—O—; X$^4$ is alkyl or phenyl) and phosphoramidate (methoxyethylamine and the like), and are synthesized as described in the generally available literature and in references cited herein (Sood, A., et al, *J Am Chem Soc* (1990) 112:9000–9001; WO 91/08213; WO 90/15065; WO 91/15500; Stirchak, E. P. et al *Nucleic Acid Res* (1989) 17:6129–6141; U.S. Pat. No. 5,034,506; U.S. Pat. No. 5,142,047; Hewitt, J. M. et al, *Nucleosides and Nucleotides* (1992) 11:1661–1666). Substitute linkages that can be used in the oligomers disclosed herein also include the sulfonamide (—O—SO$_2$—NH—), sulfide (—CH$_2$—S—CH$_2$—), sulfonate (—O—SO$_2$—CH$_2$—), carbamate (—O—C(O)—NH—, —NH—C(O)—O—), dimethylhydrazino (—CH$_2$—NCH$_3$—NCH$_3$—), sulfamate (—O—S(O)(O)—N—; —N—S(O)(O)—N—), 3'-thioformacetal (—S—CH$_2$—O—), formacetal (—O—CH$_2$—O—), 3'-amine (—NH—CH$_2$—CH$_2$—), N-methylhydroxylamine (—CH$_2$—NCH$_3$—O—) and 2'5' linkages (such as 2',5' carbamate (2' —N(H)—C(O)—O— 5'), 5',2' carbamate (2' —O—C(O)—N(H)— 5'), 5',2' methylcarbamate (2' —O—C(O)—N (CH$_3$)— 5') and 5',2' thioformacetal (2' —O—CH$_2$—S— 5'). 2',5' linkages are disclosed in pending U.S. application Ser. No. 07/892,902, filed Jun. 1, 1992, incorporated herein by reference). Riboacetal linkages are disclosed and claimed in commonly owned pending U.S. patent application Ser. Nos. 690,786, filed Apr. 24, 1991, 763,130, filed Sep. 20, 1991, and 806,710 filed Dec. 12, 1991, incorporated herein by reference. Except where specifically indicated, the substitute linkages, such as a formacetal linkage, —O— CH$_2$— O—, are linked to either the 3' or 2' carbon of a nucleomonomer on the left side and to the 5' carbon of a nucleomonomer on the right side. A formacetal linked (3',5') dimer is shown in FIG. 1, formula (6). Thus a formacetal linkage can be indicated as 3' —O—CH$_2$—O— 5' or 2' —O—CH$_2$O— 5'. The designations of a 3', 2' or 5' carbon can be modified accordingly when a structure other than ribose, deoxyribose or arabinose is linked to an adjacent nucleomonomer. Such structures include a hexose, morpholino ring, carbocyclic ring (e.g. cyclopentane) and the like.

The use of carbamate, carbonate, sulfide, sulfoxide, sulfone, N-methylhydroxylamine and dimethylhydrazino linkages in synthons or oligomers has been described (Vaseur, J-J. et al, *J Amer Chem Soc* (1992) 114:4006–4007; WO 89/12060; Musicki, B. et al, *J ora Chem* (1990) 55:4231–4233; Reynolds, R. C., et al *J org Chem* (1992) 57:2983–2985; Mertes, M. P., et al, *J Med Chem* (1969) 12:154–157; Mungall, W. S., et al, *J Ora Chem* (1977) 42:703–706; Stirchak, E. P., et al, *J Org Chem* (1987) 52:4202–4206; Wang, H., et al, *Tet Lett* (1991) 50:7385–7388; International Application No. PCT US91/03680). Substitute linkage(s) can be utilized in the oligomers for a number of purposes such as to further facilitate binding with complementary target nucleic acid sequences and/or to increase the stability of the oligomers toward nucleases.

By "positive modification" is meant use of any modification of formula (1) or (2) of the invention which results in increased binding affinity.

By "negative modification" is meant an additional nucleomonomer modification of an oligomer comprising a base of formula (1) or (2) which results in a decrease in binding affinity or use of a substitute linkage which may result in a decrease in binding affinity.

For example, a negative substitute linkage modification is at least one selected from phosphorothioate, methylphosphonate, thionomethylphosphonate, phosphoroamidate and triester for a phosphodiester linkage.

Nucleosides

The term "nucleoside" will include ribonucleosides, deoxyribonucleosides, or to any other nucleoside which is an N-glycoside or C-glycoside of a purine or pyrimidine base, or modified purine or pyrimidine base. The stereochemistry of the sugar carbons can be other than that of D-ribose in one or more residues. The pentose moiety can be replaced by a hexose and incorporated into oligomers as described (Augustyns, K., et al *Nucl Acids Res* (1992) 18:4711–4716). Also included are analogs where the ribose or deoxyribose moiety is replaced by an alternate structure such as a hexose or such as the 6-member morpholino ring described in U.S. Pat. No. 5,034,506. Nucleosides as defined herein also includes a purine or pyrimidine base linked to an amino acid or amino acid analog having a free carboxyl group and a free amino group or protected forms thereof. Exemplary nucleosides have been described (Nielsen, P. E. ibid; commonly owned copending U.S. application Ser. Nos. 07/889,736, filed Can 28, 1992, and 07/894,397, filed Jun. 5, 1992, both applications incorporated herein by reference in their entirety).

"Nucleosides" also include those moieties which contain modifications of the sugar, for example, wherein one or more of the hydroxyl groups are replaced with halogen, aliphatic groups, or functionalized as ethers, amines, and the like. Such structures include a hexose, morpholino ring, carbocyclic ring (e.g. cyclopentane) and the like.

Base

"Base" as used herein includes those moieties which contain not only the known purine and pyrimidine bases and the invention bases, but also heterocyclic bases which have been modified and tautomers thereof. Such modifications include alkylated purines or pyrimidines, acylated purines or pyrimidines, or other heterocycles. Such "analogous purines" and "analogous pyrimidines" or purine or pyrimidine analogs are those generally known in the art, some of which are used as chemotherapeutic agents. An exemplary, but not exhaustive, list includes N$^4$,N$^4$-ethanocytosine, 7-deazaxanthosine, 7-deazaguanosine, 8-oxo-N$^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, N$^6$-isopentenyl-adenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N$^6$-methyladenine, 7-methylguanine, 5-methylaminomethyl uracil, 5-methoxy aminomethyl-2-thiouracil, 5-methoxyuracil, 2-methylthio-N$^6$-isopentenyladenine, pseudouracil, 5-methyl-2-thiouracil, 2-thiouracil, 4-thiouracil, 5-methyluracil, 2-thiocytosine, and 2,6-diaminopurine. In addition to these base analogs, pyrimidine analogs including 6-azacytosine, 6-azathymidine and 5-trifluoromethyluracil described in Cook, D. P., et al, International Publication No. WO 92/02258 (incorporated herein by reference) can be conveniently incorporated into the invention oligomers.

Bases of formula (1) or (2) containing sulfur at the 2 and/or 4 position can be incorporated into oligomers and derivatized with alkynyl as R$^2$ essentially as described above. In corporation of 4-thiouridine and 2-thiothymidine into oligomers has been described (Nikiforov, T. T., et al, *Tet Lett* (1992) 33:2379–2382; Clivio, P., et al *Tet Lett* (1992) 33:65–68; Nikiforov, T. T., et al, *Tet Lett* (1991) 32:2505–2508; Xu, Y.-Z., et al *Tet Lett* (1991)

32:2817–2820; Clivio, P., et al *Tet Lett* (1992) 33:69–72; Connolly, B. A., et al., *Nucl. Acids Res.* (1989) 17:4957–4974).

Preferred bases are of the formula (1) and (2) but also include adenine, guanine, thymine, uracil, cytosine, 5-methylcytosine, 8-oxo-$N^6$-methyladenine, pseudoisocytosine, and 7-deazaxanthosine. Synthesis and use of oligomers that bind to duplex DNA sequences via GT binding motif containing 7-deazaxanthosine is described in commonly owned pending U.S. application Ser. No. 07/787,920, filed Nov. 7, 1991, incorporated herein by reference.

Synthesis

Oligomers or the segments thereof are conventionally synthesized. The synthetic methods known in the art and described herein can be used to synthesize oligomers containing bases of the invention, as well as other bases known in the art, using appropriately protected nucleomonomers (see FIG. 12). Methods for the synthesis of oligomers are found, for example, in Froehler, B., et al., *Nucleic Acids Res* (1986) 14:5399–5467; *Nucleic Acids Res* (1988) 16:4831–4839; *Nucleosides and Nucleotides* (1987) 6:287–291; Froehler, B., *Tetrahedron Letters* (1986) 27:5575–5578; Caruthers, M. H. in *Oligodeoxynucleotides-Antisense Inhibitions of Gene Expression* (1989), J. S. Cohen, editor, CRC Press, Boca Raton, p7–24; Reese, C. B. et al, *Tetrahedron Letters* (1985) 26:2245–2248. Synthesis of the methylphosphonate linked oligomers via methyl phosphonamidite chemistry has also been described (Agrawal, S. et al., *Tetrahedron Letters* (1987) 28:3539–3542; Klem, R. E., et al, International Publication Number WO 92/07864).

Figure 5:
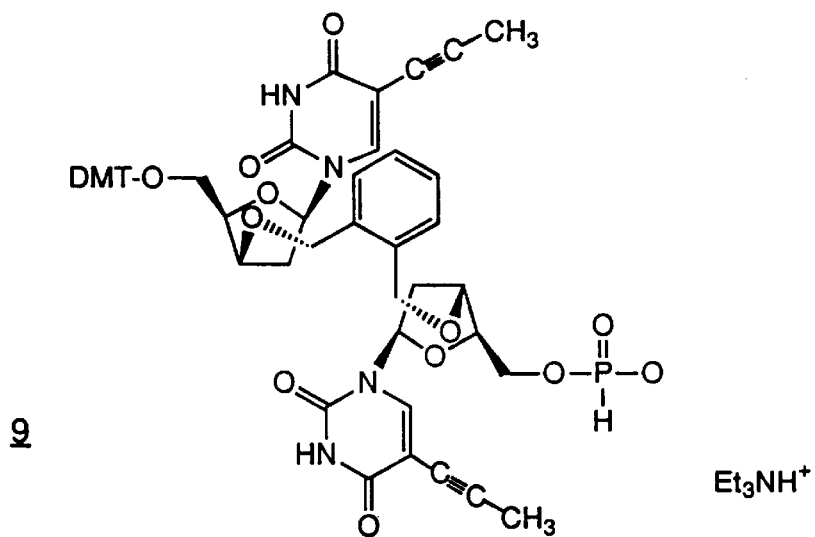
FIG. 5.
Figure 1:
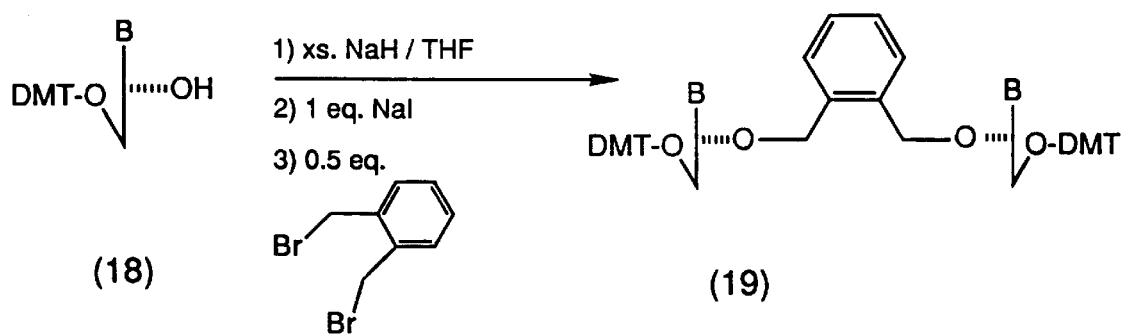
Figures 2, 5:
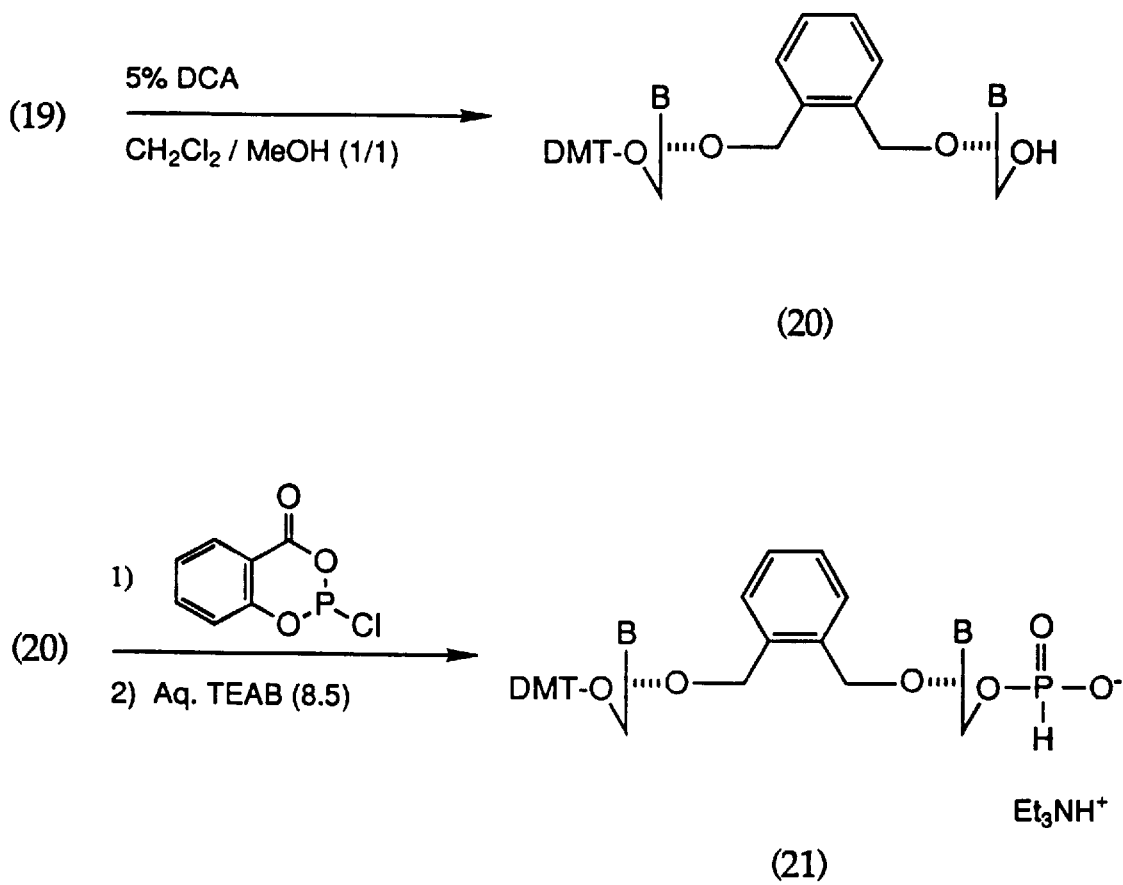

Oligomers of the invention containing bases of formula (1) or (2) and one or more substitute linkages can be synthesized by one or more of four general methods according to the reaction conditions required for synthesis of a given substitute linkage. In the first method (#1), nucleomonomers containing bases of formula (1) or (2) are directly incorporated into oligomers or a convenient fragment thereof using standard synthesis conditions and reagents. Exemplary schemes are shown in FIGS. 5 and 12 and exemplary linkages that can be made by method #1 include phosphodiester, phosphorothioate, phosphoroamidate, methylphosphonate, phosphorodithioate, carbonate, morpholino carbamate and sulfonate.

Method #2 involves synthesis of short synthons (dimers, trimers, etc) starting with an appropriate precursor such as a 5-bromo or 5-iodo precursor (as described below) which is subsequently converted to the C-5 substituent of formula (1) or (2) and a synthon suitable for incorporation into oligomers. This approach is exemplified in FIGS. 7, 8 and 11 and is suitable for synthesis of linkages including N-methylhydroxylamine, dimethylhydrazo, sulfamate, carbamate, sulfonate, sulfonamide, formacetal thioformacetal and carbonate.

Synthesis method #3 starts with uridine or cytidine (unprotected or N-protected) nucleomonomers which is subsequently iodinated. Introduction of the $R^2$ group at the 5-position is accomplished within the synthetic route to the desired dimer or trimer synthon. Method #3 is exemplified in FIG. 9 and is suitable for synthesis of linkages including N-methylhydroxylamine, dimethylhydrazino, sulfamate, formacetal, thioformacetal, riboacetal, sulfonate, sulfonamide, carbamate, carbonate and boranophosphate linkages.

Method #4 starts with either (1) uracil or cytosine base containing $R^2$, followed by conversion to a nucleomonomer suitable for incorporation into oligomers (e.g. amide linkages) as exemplified in FIG. 12 or (2) a suitable precursor such as 5-iodocytosine, 5-iodouracil, cytosine or uracil which is glycosylated or alkylated followed by conversion of the nucleomonomer to a derivative containing $R^2$ and converted to the desired synthon (e.g. linkages such as sulfide, sulfoxide or sulfonate).

In general, reaction conditions that are needed to synthesize a particular dimer, trimer or larger synthon and may not be compatible with an $R^2$ alkynyl 2'-deoxyuridine or 2'-deoxycytidine are (1) electrophilic addition reactions, or conditions that could promote electrophilic addition to C—C multiple bonds (e.g. HCl, HF, $BF_3$, $Cl_2$ or $Br_2$); (2) conditions that could promote reduction of C—C multiple bonds (e.g., hydrogenation via $H_2$/Pd/C or hydrides such as $B_2H_6$, $BH_3$·complex or as a class, tin hydrides or aluminum hydrides); (3) conditions that promote free radical reactions (e.g., $Cl_2$hv, peroxides or AIBN); and (4) reaction conditions that promote oxidation of C—C multiple bonds (e.g. $KMnO_4$, $OsO_4$, alkyl carboxylic peracids). Synthetic schemes involving these reaction conditions may prevent the use of Method #1.

In general, reaction conditions that are required to synthesize certain oligomers that may not compatible with 5-iodo-2'-deoxyuridine or 5-iodo-2'-deoxycytidine, or the like, are (1) conditions that promote reduction of aryl iodides (e.g., $H_2$ or hydrides), (2) alkylation and arylation reactions mediated by organometallic reagents or (3) reactions that promote free radical reactions (e.g., $Cl_2$hv, peroxides or AIBN). Synthetic schemes involving these reactions may prevent use of Method #2.

Method #3 starts with 2'-deoxyuridine or 2'-deoxycytidine and the nucleomonomer is subsequently converted to the 5-iodo (or 5-bromo or 5-triflate) derivative (Robins, M. J. et al, *Can. J. Chem* (1982) 60:554–557; Chang, P. K. et al, *J Med Chem* (1963) 6:428–430; Crisp, G. T., et al., *Tet Lett* (1990) 31:1347–1350; and Torrence, P. F., et al., *J. Med. Chem* (1979) 22:316–319) at the desired step, followed by conversion to a $R^2$ substituent at desired step. In some schemes it is advantageous to convert 2'-deoxyuridine to 5-$R^2$-2'-deoxycytidine as needed by previously desired methods (Divakar, K. J., et al, *J Chem. Soc. Perkin Trans I* (1982) p 1171–1176). Where one of these reactions or conditions are used for synthesis of a given oligomer or fragment thereof, a nucleomonomer such as 2'-deoxyuridine can be utilized followed by conversion to the $R^2$ derivative and the cytidine derivatives thereof.

Additional exemplary linkages that can be synthesized by these general methods are summarized in Table A below.

TABLE A

| Linkage Structure* | Method | Reference** |
|---|---|---|
| 2' —S—$CH_2$— 5' | 1–4 | 1 |
| 3' —S—$CH_2$— 5' | 1–4 | 2 |
| 2' —S(O)—$CH_2$— 5' | 1–4 | 1 |
| 3' —S(O)—$CH_2$— 5' | 1–4 | 1 |
| 2' —S(O)(O)—$CH_2$— 5' | 1–4 | 1 |
| 3' —S(O)(O)—$CH_2$— 5' | 1–4 | 1 |
| 2' —$CH_2$—S— 5' | 3,4 | 1 |
| 3' —$CH_2$—S— 5' | 3,4 | 2 |
| 2' —$CH_2$—S(O)— 5' | 3,4 | 1 |
| 3' —$CH_2$—S(O)— 5' | 3,4 | 2 |
| 2' —$CH_2$—S(O)(O)— 5' | 3,4 | 1 |
| 3' —$CH_2$—S(O)(O)— 5' | 3,4 | 2 |
| 2' —$CH_2$—$CH_2$—O— 5' | 3,4 | 1 |
| 3' —$CH_2$—$CH_2$—O— 5' | 3,4 | 2 |
| 2' —N(C(O)($OR^A$))—$CH_2$—$CH_2$— 5' | 3,4 | 1 |

TABLE A-continued

| Linkage Structure* | Method | Reference** |
|---|---|---|
| 3' —N(C(O)(OR$^A$))—CH$_2$—CH$_2$— 5' | 3,4 | 2 |
| 2' —S—CH$_2$—CH$_2$— 5' | 3,4 | 1 |
| 3' —S—CH$_2$—CH$_2$— 5' | 3,4 | 2 |
| 2' —NH—C(O)—O— 5' | 3,4 | 1 |
| 2' —O—CH$_2$—S— 5' | 2–4 | 1 |
| 2' —O—C(O)—N(R$^B$)— 5' | 2–4 | 1 |
| 5' morpholino N—CH$_2$— 5' | 1–4 | 2 |
| —X—C((CH$_2$)$_2$NR$^c$(CH$_2$)$_2$)—X-5' | 2–4 | 3 |
| —X—C((CH$_2$)$_2$O(CH$_2$)$_2$)—X-5' | 2–4 | 3 |
| —X—C((CH$_2$)$_2$S(O)(O)(CH$_2$)$_2$))—X-5' | 2–4 | 3 |
| —X—C((CH$_2$)$_2$S(O)(CH$_2$)$_2$))—X-5' | 2–4 | 3 |
| —X—C((CH$_2$N(R$^c$)(CH$_2$)$_2$)—X-5' | 2–4 | 3 |
| —X—C((CH$_2$N(R$^c$)(CH$_2$N(R$^c$))—X-5' | 2–4 | 3 |

*R$^A$ = C$_{1-6}$ alkyl, e.g. CH$_2$CH$_3$ or (CH$_2$)$_5$CH$_3$; R$^B$ = H or C$_{1-6}$ alkyl, e.g. CH$_3$; X = O or S;
R$^C$ = C$_{1-6}$ alkyl, CN or C$_{1-6}$ haloalkyl, e.g. CF$_3$; the linkages indicate covalent attachment of the indicated atom with either a 2', 3' or 5' carbon of ribose or deoxyribose.
**1 - Synthesis is accomplished essentially as described in PCT/US91/06855 for equivalent 3', 5' linkages.
2 - International Application Number PCT/US91/06855.
3 - International Application Number PCT/US90/06110; linkages having a structure such as C((CH$_2$)$_2$(CH$_2$)$_2$O) are cyclic ketals.

Figures 1, 17:
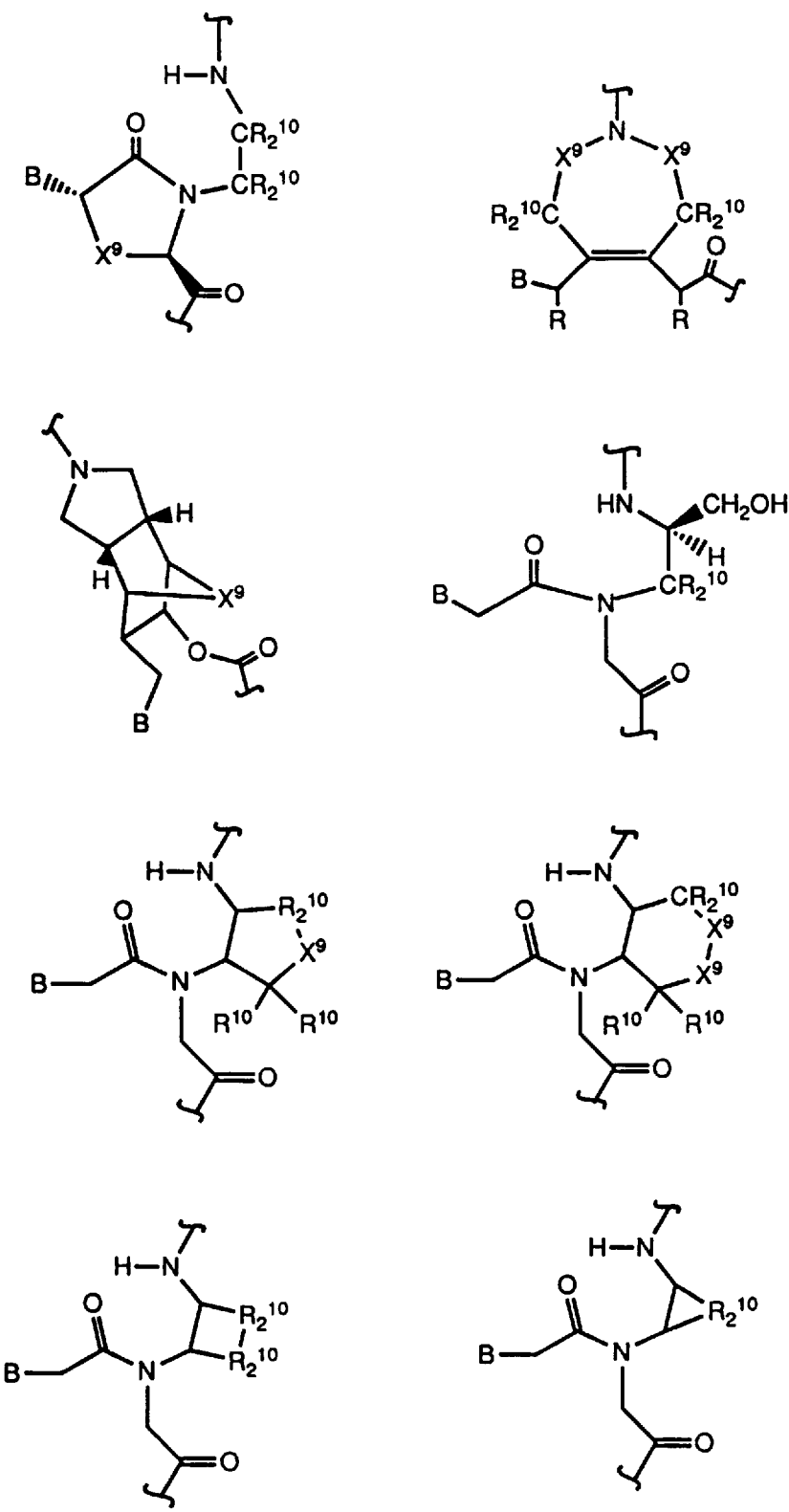
FIG. 17.
Figures 2, 17:
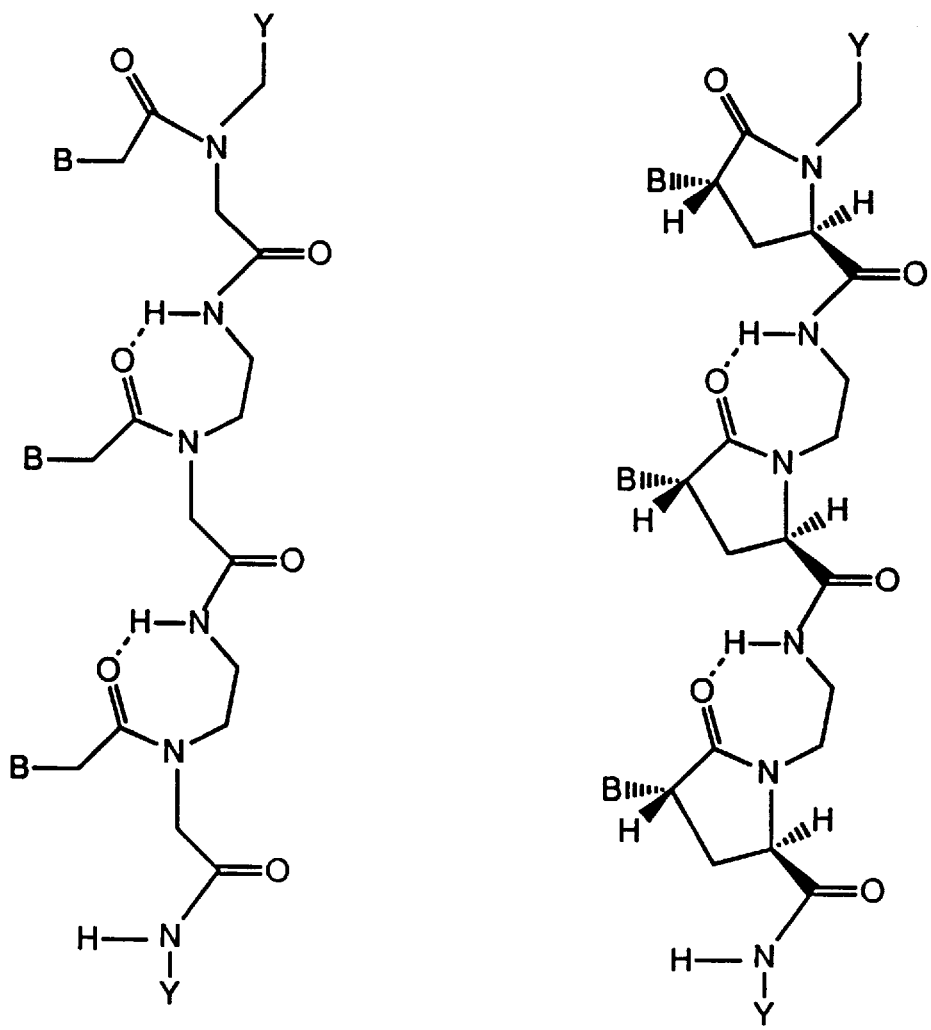
Figures 3, 17:
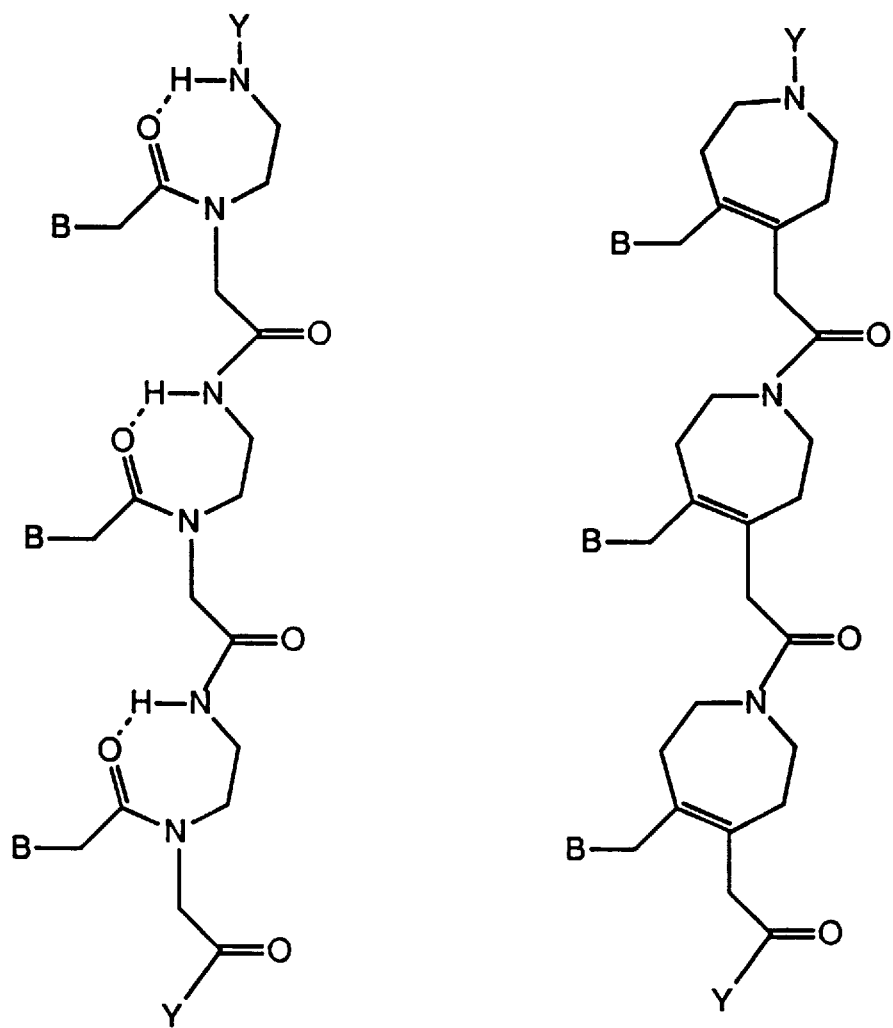
Figure 18:
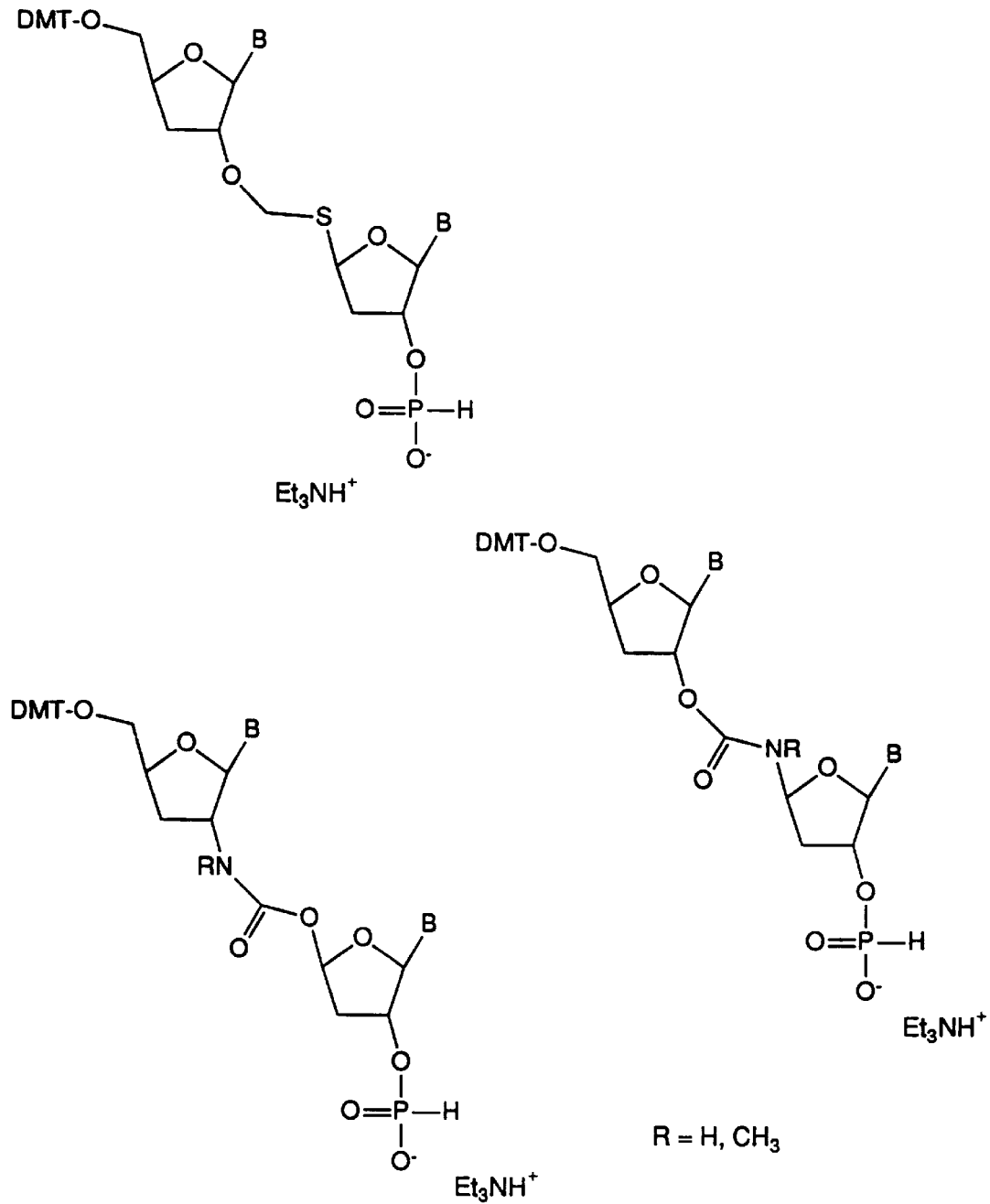
FIG. 18. Dimers synthons containing bases of the invention and having exemplary 2',5' linkages; thioformacetal and carbamate linkages.

In addition to the substitute linkages given in Table A, FIG. 17 shows a series of repeating nucleomonomer units (17-1) and exemplary amide linked oligomers (17-2, 17-3) containing selected repeating units that can contain the base analogs of the invention. In FIG. 17-1, X$^9$ is S, O, SO, SO$^2$, CH$_2$, CHF, CF$_2$ or NR$^{10}$ and R$^{10}$ is (independently) H, F, OH, OCH$_3$, CH$_3$, or CH-lower alkyl provided that adjacent X$^9$ are not both O. In FIGS. 17-2 and 17-3, each Y is independently selected and has the meaning described above (e.g. Y is H, an oligomer, a blocking group such as FMOC, tBOC, OH, DMT, MMT or an coupling group suitable for oligomer synthesis). Nucleomonomers required to synthesize oligomers containing such linkages are synthesized by method #4.

Oligomers of the invention can be synthesized by any suitable chemistry including amidite, triester or hydrogen phosphonate coupling methods and conditions. The oligomers are preferably synthesized from appropriate starting synthons such as nucleomonomers of formula (3) or (4) wherein R$^1$ at the 5'-position is DMT, MMT, FMOC (9-fluorenylmethoxycarbonyl), PACO (phenoxyacetyl), a silyl ether such as TBDMS (t-butyldiphenylsilyl) or TMS (trimethylsilyl) and R$^1$ at the 3'-position is an ester, H-phosphonate, an amidite such as β-cyanoethylphosphoramidite, a silyl ether such as TBDMS or TMS or t-butyldiphenyl. Alternatively, appropriate uridine or cytidine precursors such as blocked 5-iodo-2'-deoxyuridine, 5-iodo-2'-O-alkyluridine, 5-bromo-2'-deoxyuridine, 5-trifluoromethanesulfonate-2'-deoxyuridine, 5-bromo-2'-O-alkyluridine or blocked and protected 5-iodo-2'-deoxycytidine, 5-bromo-2'-deoxycytidine, 5-trifluoromethanesulfonate-2'-deoxycytidine, 5-iodo-2'-O-alkylcytidine, 5-bromo-2'-O-alkylcytidine can be conveniently incorporated into short oligomers such as dimer, trimer, tetramer, pentamer or longer synthons that are subsequently derivatized to yield R$^2$ at the 5-position and then incorporated into suitable synthons and longer oligomers.

Synthesis of oligomers containing about 4 or more nucleomonomer residues-is preferably accomplished using synthons such as monomers, dimers or trimers that carry a coupling group suitable for use with amidite, H-phosphonate or triester chemistries. The synthon can be used to link the oligomer via a phosphodiester or phosphorous-containing substitute linkage (phosphorothioate, methylphosphonate, thionomethylphosphonate, phosphoramidate and the like).

Synthesis of other nonphosphorous-containing substituted linkages can be accomplished using appropriate precursors as described herein (FIGS. 7-10) and are known in the art.

In addition to employing these very convenient and now most commonly used, solid phase synthesis techniques, oligomers can also be synthesized using solution phase methods such as triester synthesis. These methods are workable, but in general, less efficient for oligomers of any substantial length.

Intermediates or starting materials

In other aspects, the invention is directed to intermediates in the synthesis of the oligomers of the invention, including nucleomonomer analogs of formula (3) or (4):

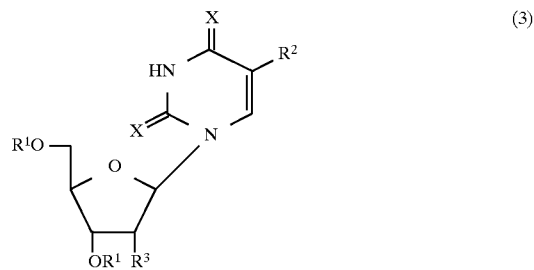

(3)

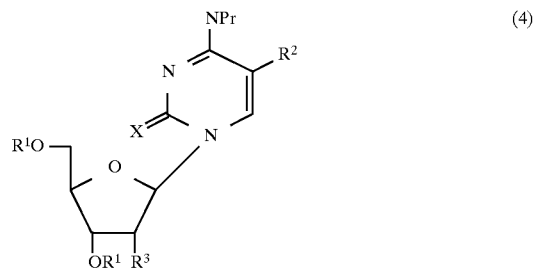

(4)

wherein each R$^1$ is independently H or a blocking group;
R$^2$ and X are as defined above;
R$^3$ is selected from the group consisting of H, OH, F, NH$_2$, OR or SR, wherein OR is O-allyl or SR is S-allyl or O or S alkyl (C$_{1-3}$), wherein alkyl including methyl, ethyl and propyl); and
Pr is (H)$_2$ or a protecting group;
provided that if X is O, R$^3$ is H or OH, and both R$^1$ are H, then R$^2$ is 1,3-pentadiynyl, 2-, 3- and 4-pyridine-ethynyl, 2-, 4- and 5-pyrimidine-ethynyl, triazine-ethynyl, arylethynyl, 2-, 4- and 5-pyrimidinyl, 2- and 4-imidazolyl, 2- and 3-pyrrolyl-ethynyl, 2- and 3-furanyl-ethynyl, 2- and 3-thienyl-ethynyl, 2- and 4-imidazolyl-ethynyl, 2-, 4- and 5-thiazoyl-ethynyl or 2-, 4- and 5-oxazolyl-ethynyl, 4-oxazolyl, 4-thiazoyl, 3-pyrroyl, 3-furanyl, 3-thienyl and
further provided that for formula 3, when X is O, and R$^1$ and R$^3$ are H, then R$^2$ is not vinyl, 1-butenyl, 1-pentenyl, 1-hexenyl, 1-heptenyl, 1-octenyl, 1-propynyl, 1-butynyl, 1-hexynyl, 1-heptynyl or 1-octynyl.

Suitable protecting groups (Pr) include diisopropylformanidine, di-n-butylformanidine, diisobutylformamidine and benzoyl and suitable $R^1$ groups including DMT, MMT, FMOC, a phosphoramidite such as β-cyanoethylphosphoramidite, hydrogen-phosphonate and methylphosphonamidite.

Preferred protected nucleomonomers are nucleomonomers of formula (3) and (4) where X is O, $R^1$ at the 5' position is DMT, MMT or FMOC; $R^1$ at the 3' position is N,N-diisopropylamino-β-cyanoethoxyphosphine, N,N-diisopropylaminomethoxyphosphine or hydrogen phosphonate; $R^2$ is 1-propynyl, 3-methyl-1-butynyl, 2-pyrrolyl, 2-thienyl, 2-imidazolyl or 2-thiazolyl; and Pr is $(H)_2$ or diisobutylformamidine.

Preferred Embodiments:

One group of preferred oligomers of the present invention can be represented by the formula (16):

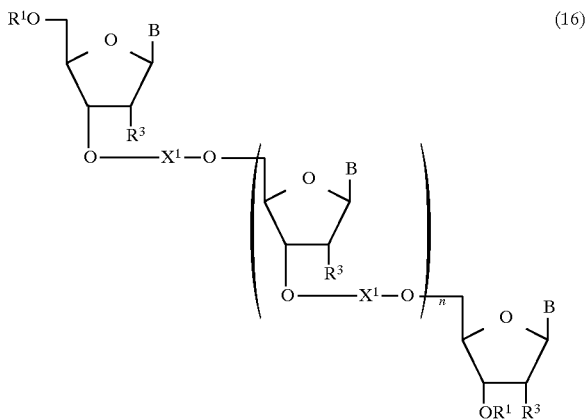

wherein each B, $R^1$ and $R^3$ are independently selected and have the meanings defined above;
  n is an integer from 0 to 98 (values of 0 to 28 are preferred); and
    each $X^1$ is independently —P(S)(O)—, —P(O)(O)— or —P($CH_3$)(O)—, —P($CH_3$)(S)—,
    provided that at least one B is of the formula (1) or (2) as defined above; and
    further provided that when at least one of said nucleomonomers of said oligomer comprises deoxyuridine 5-substituted by vinyl, 1-butenyl, 1-pentenyl, 1-hexenyl, 1-heptenyl 1-octenyl, 1-propynyl, 1-butynyl, 1-hexynyl, 1-heptynyl, or 1-octynyl, then the remainder of the nucleomonomers comprising said oligomer are not solely comprised of phosphodiester linked 2'-deoxyadenosine, 2'-deoxyguanosine, 2'-deoxycytidine, thymidine or a combination thereof. Methylphosphonate, thionomethylphosphonate or phosphorothioate substitute linkages enhance the nuclease stability of the oligomers while their negative impact on oligomer affinity for target nucleic acids is compensated by the inclusion of the 5-substituted pyrimidines of the invention.

The most preferred $R^2$ group is 1-propynyl. Preferred $R^3$ groups are H, OH, F and O-allyl.

Other preferred oligomers of the invention contain substitute linkages other than phosphodiester, phosphorothioate, thionomethylphosphonate or methylphosphonate. Particularly useful forms of these substitute linkages include riboacetal, formacetal and 3'-thioformacetal linkages, with 3'-thioformacetal being most preferred.

For synthesis of oligomers containing formacetal-type substitute linkages, in lieu of at least some phosphodiester linkages, dimeric synthons of the formula (6) shown in FIG. 1, wherein the substituents B, X, $R^1$ and $R^3$ are as defined above are particularly useful.

The foregoing synthon is obtained by first preparing the 5-iodo pyrimidine forms of B and then converting these to 5-propyne derivatives, for example, by treating the dimer synthon with propyne in the presence of palladium, CuI, triethylamine, and DMF. These synthons can be incorporated into an oligomer using standard synthesis techniques as shown in FIGS. 7, 8, 9 and 11. Synthesis of formacetal and 3'-thioformacetal substitute linkages is described in commonly owned pending U.S. application Ser. Nos. 07/874,334, filed Apr. 24, 1992, and 07/690,786, filed Apr. 24, 1991, which applications are incorporated herein by reference. Trimer synthons containing formacetal, 3'-thioformacetal, riboacetal or other substitute linkages are also preferred compounds. Trimers and tetramers are preferred for synthesis of oligomers having enhanced permeation across cell membranes.

The synthesis of oligomers containing methylphosphonate and phosphodiester linkages is effected using art-known solid-phase oligomer synthesis techniques. A description of modifications useful in the synthesis of phosphorothioate linked oligomers are found, for example, in EP publication 288,163; wherein the oxidation step in solid phase automated synthesis using amidite chemistry can be independently adjusted at any step to obtain the phosphorothioate. An alternate method for synthesis of oligomers with phosphorothioate linkages, via hydrogen phosphonate chemistry, has also been described (Froehler, B., et al., *Nucleic Acid Res* (1986) 14:5399–5467; Froehler, B., *Tetrahedron Letters* (1986) 27:5575–5578). Sulfurization can be accomplished using reagents such as tetraethylthiuram disulfide, dibenzoyl tetrasulfide, thiophosphoric acid disulfide and the like, 3H-1, 2-benzodithiol-3-one 1,1-dioxide and the like as described (Vu, H. et al, *Tet Lett* (1991) 26:3005–3008; Rao, M. V., et al, *Tet Lett* (1992) 33:4839–4842; U.S. Pat. No. 5,151,510 issued Sep. 29, 1992; Iyer, R., et al, *J Org Chem* (1990) 55:4693–4699; Dahl, O. *Sulfur Reports* (1991) 11:167–192). These sulfurization reagents can be used with either phosphoramidite or hydrogen-phosphonate chemistries. Synthesis of phosphorothioate oligomers having controlled stereochemistry can be used to generate stereoregular invention oligomers as described (International Publication No. EP 0 506 242). The thionomethyl phosphonate is prepared with methylphosphonamidite followed by sulfurization as described (Roelen, H. P. C. F., et al, *Tet Lett* (1992) 33:2357–2360) or with the sulfurization reagents described above.

Covalent Bonding Moiety

Included in some of the oligomers of the invention is a moiety which is capable of effecting at least one covalent bond between the oligomer and the target sequence. Multiple covalent bonds can also be formed by providing a multiplicity of such moieties. The covalent bond is preferably to a base residue in the target strand, but can also be made with other portions of the target, including the sugar or phosphodiester. The reaction nature of the moiety which effects crosslinking determines the nature of the target in the duplex. Preferred crosslinking moieties include acylating and alkylating agents, and, in particular, those positioned relative to the sequence specificity-conferring portion so as to permit reaction with the target location in the strand.

The crosslinking moiety can conveniently be placed as an analogous pyrimidine or purine residue in the sequence of the oligomer. The placement can be at the 5'- and/or 3'-ends, the internal portions of the sequence, or combinations of the above. Placement at the termini to permit enhanced flexibility is preferred. Analogous moieties can also be attached to peptide backbones.

In one preferred embodiment of the invention, a switchback oligomer containing crosslinking moieties at either end can be used to bridge the strands of the duplex with at least two covalent bonds. In addition, oligomer sequences of inverted polarity can be arranged in tandem with a multiplicity of crosslinking moieties to strengthen the complex.

Exemplary of alkylating moieties that are useful in the invention include $N^4,N^4$-ethanocytosine and $N^6,N^6$-ethanoadenine.

It is clear that the base need not be a purine or pyrimidine; indeed the moiety to which the reactive function is attached need not be a base at all. Any means of attaching the reactive group is satisfactory so long as the positioning is correct.

Inverted Polarity

In their most general form, inverted polarity oligomers, that can incorporate one or more nucleomonomers described above, contain at least one segment along their length of the formula:

 (1)

 (2)

where —C— symbolizes any method of coupling the nucleomonomer sequences of opposite polarity (Froehler, B. C., et al *Biochemistry* (1992) 31:1603–1609; Horne, D. A., et al *J Am Chem Soc* (1990) 112:2435–2437; Beal, P. A., et al *J Am Chem Soc* (1992) 114:4976–4978).

In these formulas, the symbol 3'----5' indicates a stretch of oligomer in which the linkages are consistently formed between the 5'-hydroxyl of the ribosyl residue of the nucleomonomer to the left with the 3'- (or 2'- for oligomers having 2', 5' linkages) hydroxyl of the ribosyl residue of the nucleomonomer to the right (i.e., a region of uniform polarity), thus leaving the 5'-hydroxyl of the rightmost nucleomonomer ribosyl residue free for additional conjugation. Analogously, 5'----3' indicates a stretch of oligomer in the opposite orientation wherein the linkages are formed between the 3'-hydroxyl of the ribosyl residue of the left nucleomonomer and the 5'-hydroxyl of the ribosyl residue of the nucleomonomer on the right, thus leaving the 3'-hydroxyl of the rightmost nucleomonomer ribosyl residue free for additional conjugation.

The linkage, symbolized by —C—, can be formed so as to link the 5'-hydroxyls of the adjacent ribosyl residues in formula (1) or the 3' hydroxyls of the adjacent ribosyl residues in formula (2), or the "1—C—" linkage can conjugate other portions of the adjacent nucleomonomers so as to link the inverted polarity strands. "—C—" can represent a linker moiety, or simply a covalent bond.

It should be noted that if the linkage between strands of inverted polarity involves a sugar residue, either the 3'- or 2'-position can be involved in the linkage, and either of these positions can be in either R or S configuration. The choice of configuration will in part determine the geometry of the oligomer in the vicinity of the linkage. Thus, for example, if adjacent 3'-positions are used to effect a covalent linkage, less severe deformation of the oligomer chain will generally occur if both 3'-hydroxyls involved in the linkage are in the conventional R configuration. If they are both in the S configuration, this will result in a favorable "kink" in the chain.

In addition to the use of standard oligonucleotide synthesis techniques or other couplings to effect the 5'—5' or 3'—3' linkage between ribosyl moieties, alternative approaches to joining the two strands of inverted polarity can be employed.

For example, the two appended bases of the opposing termini of the inverted polarity oligomer sequences can be linked directly or through a linker, or the base of one can be linked to the sugar moiety of the other. Any suitable method of effecting the linkage can be employed. The characterizing aspect of the switchback oligomers of the invention is that they comprise tandem regions of inverted polarity, so that a region of 3'→5' polarity is followed by one of 5'→3' polarity, or vice versa, or both.

Depending on the manner of coupling the segments with inverted polarity, this coupling can be effected by insertion of a dimer wherein the appropriate 3'-positions of each member of the dimer or the 5'-positions of each member of the dimer are activated for inclusion of the dimer in the growing chain, or the conventional synthesis can be continued using the condensing nucleomonomer which is blocked in the inverse manner to that which would be employed if the polarity of the chain were to remain the same. This additional nucleomonomer can also contain a linker moiety which can be included before or after condensation to extend the chain.

The synthesis of oligomers having modified residues and/or inverted polarity can be accomplished utilizing standard solid phase synthesis methods.

In general, there are two commonly used solid phase-based approaches to the synthesis of oligomers containing conventional 3'→5' or 5'→3' linkages, one involving intermediate phosphoramidites and the other involving intermediate phosphonate linkages. In the phosphoramidite based synthesis, a suitably protected nucleomonomer having a cyanoethylphosphoramidite at the position to be coupled is reacted with the free hydroxyl of a growing nucleomonomer chain derivatized to a solid support. The reaction yields a cyanoethylphosphite, which linkage must be oxidized to the cyanoethylphosphate at each intermediate step, since the reduced form is unstable to acid. The H-phosphonate-based synthesis is conducted by the reaction of a suitably protected nucleomonomer containing an H-phosphonate moiety at a position to be coupled with a solid phase-derivatized nucleomonomer chain having a free hydroxyl group, in the presence of a suitable activator to obtain an H-phosphonate diester linkage, which is stable to acid. Thus, the oxidation to the phosphate or thiophosphate can be conducted at any point during the synthesis of the oligomer or after synthesis of the oligomer is complete. The H-phosphonates can also be converted to phosphoramidate derivatives by reaction with a primary or secondary amine in the presence of carbon tetrachloride. To indicate the two approaches generically, the incoming nucleomonomer is regarded as having a "coupling phosphite/phosphate" group.

Variations in the type of substitute linkage are achieved by, for example, using the methyl phosphonate precursors rather than the H-phosphonates per se, using thiol derivatives of the nucleomonomer moieties and generally by methods known in the art. Nonphosphorous based linkages can also be used, such as the formacetal 3'-thioformacetal, 3'-amino and 5'-ether type linkages described above.

Thus, to obtain an oligomer segment which has a 3'→5' polarity, a nucleomonomer protected at the 5'-position and containing a coupling phosphite/phosphate group at the 3'-position is reacted with the hydroxyl at the 5'-position of a nucleomonomer coupled to a solid support through its 3'-hydroxyl. The resulting condensed oligomer is deprotected and the reaction repeated with an additional 5'-protected, 3'-phosphite/phosphate coupling nucleomonomer. Conversely, to obtain an oligomeric segment of 5'→3' polarity, a nucleomonomer protected in the 3'-position and containing a coupling phosphite/phosphate in the 5'-position is reacted with a oligomer or nucleomonomer attached to a solid support through the 5'-position, leaving the 3'-hydroxyl available to react. Similarly, after condensation of the incoming nucleomonomer, the 3'-group is deprotected and reacted with an additional 3'-protected, 5'-coupling nucleomonomer. The sequence is continued until the desired number of nucleomonomers have been added.

This oligomer chain elongation will proceed in conformance with a predetermined sequence in a series of condensations, each one of which results in the addition of another nucleomonomer. Prior to the addition of a nucleomonomer having a coupling phosphite/phosphate, the protecting group on the solid support-bound nucleomonomer is removed. Typically, for example, removal of the commonly-employed dimethoxytrityl (DMT) group is done by treatment with 2.5% v/v dichloroacetic acid/dichloromethane, although 1% w/v trichloroacetic acid/dichloromethane or $ZnBr_2$-saturated nitromethane, are also useful. Other deprotection procedures suitable for other protecting groups will be apparent to those of ordinary skill in the art. The deprotected nucleomonomer or oligomer bound to solid support is then reacted with the suitably protected nucleomonomer containing a coupling phosphite/phosphate. After each cycle the carrier bound nucleomonomer is preferably washed with anhydrous pyridine/acetonitrile (1:1, v/v), again deprotected, and the condensation reaction is completed in as many cycles as are required to form the desired number of congruent polarity internucleoside bonds which will be converted to phosphoramidates, phosphorodithioates, phosphorothioates or phosphodiesters as desired.

In one embodiment, to provide the switchback linker, the incoming coupling, protected nucleomonomer is provided in the opposite polarity to the support-bound oligomers. Thus, for example, where the support-bound oligomer is 3'→5', the deprotected 5'-hydroxyl is reacted with a 3'-protected, 5'-coupling monomer, and the synthesis continued with monomers coupled at the 5'-position and protected at the 3'-position.

In another embodiment, to provide the switchback linker, a dimer synthon containing the linker element having one end which is coupled for condensation (such as a hydrogen phosphonate) to the support-bound oligomer and another end which is a protected hydroxyl group (or protected thio group) is condensed onto the support-bound oligomer. The linked dimer is condensed and deprotected using the same conditions as those used to condense and deprotect the protected nucleomonomer hydrogen phosphonate. Subsequent extension of the oligomer chain then uses nucleomonomer residues which are coupled and protected in the opposite manner from those used to synthesize the previous portion of the chain.

One approach to this synthesis, using a linker already derivatized to two nucleomonomer residues which will be included in each portion of the strand is illustrated in FIG. 5. The 5'→3' nucleomonomer portion of the strand is coupled using the 3'-DMT-5'-coupling phosphate nucleomonomers, as conventionally, to solid support. The switchback linker is derivatized to two nucleomonomer residues through their 3'-positions; the remaining 5'-positions are derivatized by the protecting group DMT in one nucleomonomer residue and a phosphonate residue in the other. The derivatized linker is coupled to the solid supported strand under standard reagent conditions and then deprotected conventionally. Further standard nucleomonomer coupling results in extension of the chain in the 3'→5' orientation.

A particularly preferred dimer synthon used to mediate the switchback in an oligomer is the O-xyloso linker (compound 9 and Formula (21) in FIG. 5. The O-xyloso linker consists of two xylose-nucleomonomers (18) linked to each other by o-xylene at the 3'-position of each xylose sugar. The switchback linker synthon was synthesized using α,α'-orthodibromoxylene and 5'-DMT nucleomonomer (18) to give the dimer (19) as shown in FIG. 5. The dimer was converted to the H-phosphonate (21) and was used in solid phase synthesis to generate oligomers. Linkers containing the bases (at position "B" in FIG. 5) thymine, 5-methylcytosine, 8-hydroxy-$N^6$-methyladenine, pseudoisocytosine, 5-propynyluracil or cytosine are synthesized as homodimers. However, the switchback linker dimers can also be synthesized as mixed heterodimers that are separated chromatographically.

A particularly useful synthon in the preparation of oligomers containing inverted polarity is of formula (5) shown in FIG. 1, wherein each Y and each B is independently chosen and have the meanings previously defined, and wherein one or both of the bases, B, can optionally be the modified base residues of formula (1) or (2) of the invention.

2' Modified Oligomers

Included in some of the oligomers containing C-5 modified pyrimidines of the invention are modifications of the ribose or deoxyribose sugar. 2'-O-methyl-, 2'-O-ethyl- and 2'-O-allyl oligomers have been synthesized and shown to bind to single-stranded complementary nucleic acid sequences (Cotten, M., et al., Nucleic Acids Res (1990) 19:2629–2635; Blencowe, B. J., et al., Cell (1989) 59:531–539; Sproat, B. S., et al., Nucleic Acids Res (1989) 17:3373–3386; Inoue, H., et al., Nucleic Acids Res (1987) 15:6131–6148; Morisawa, H., et al., European Patent Serial No. 0339842; Chavis, C., et al., J Organic Chem (1982) 47:202–206; Sproat, B. S., et al, Nucleic Acids Res (1991) 19:733–738). The 2'-modified oligomers were reported to be relatively nuclease stable compared to unmodified controls. Synthesis of 2' fluoro nucleomonomers and their incorporation into oligomers has also been described (Codington, J. F., et al, J Org Chem (1964) 29:558–564; Fazakerley, G. V., et al, FEBS Lett (1985) 182:365–369). Synthesis of oligomer analogs containing the modified bases described herein would be based on methods described. Synthesis of oligomers containing 2'-amino nucleomonomers has been described (Pieken, W. A., et al, Science (1991) 253:314–317).

In an additional use of bases (1) and (2) in oligomers of the invention, 2'-O-allyl modified sugar forms of the nucleomonomers containing the 5-substituted bases (1) and (2) of the invention are included in the oligomer. Other 2'-O-allyl-substituted nucleomonomers can also be used at other positions in the oligomer. The 2'-O-allyl nucleomonomers can be prepared using standard methods; set forth below is a method for synthesis of the 2'-O-allyl derivatized nucleomonomers containing the invention pyrimidines through a common intermediate. Thus, for example, 5-(1-propynyl) uridine is first protected at the 5'- and 3'-positions using a tetraisopropyldisiloxane reagent, and then at the 4-oxy position using ortho-nitrophenol. The protected nucleoside is then converted to the 2'-O-allyl derivative with allyl ethyl carbonate; this useful intermediate is alternatively converted to the 2'-O-allyl-derivatized 5-(1-propynyl)uridine or the corresponding 5-(1-propynyl)cytidine. The sequence of reactions for this conversion are outlined in FIG. 4.

The nucleomonomers derivatized at the 2'-position can be incorporated into oligomers in the same manner as underivatized forms.

Figure 6:
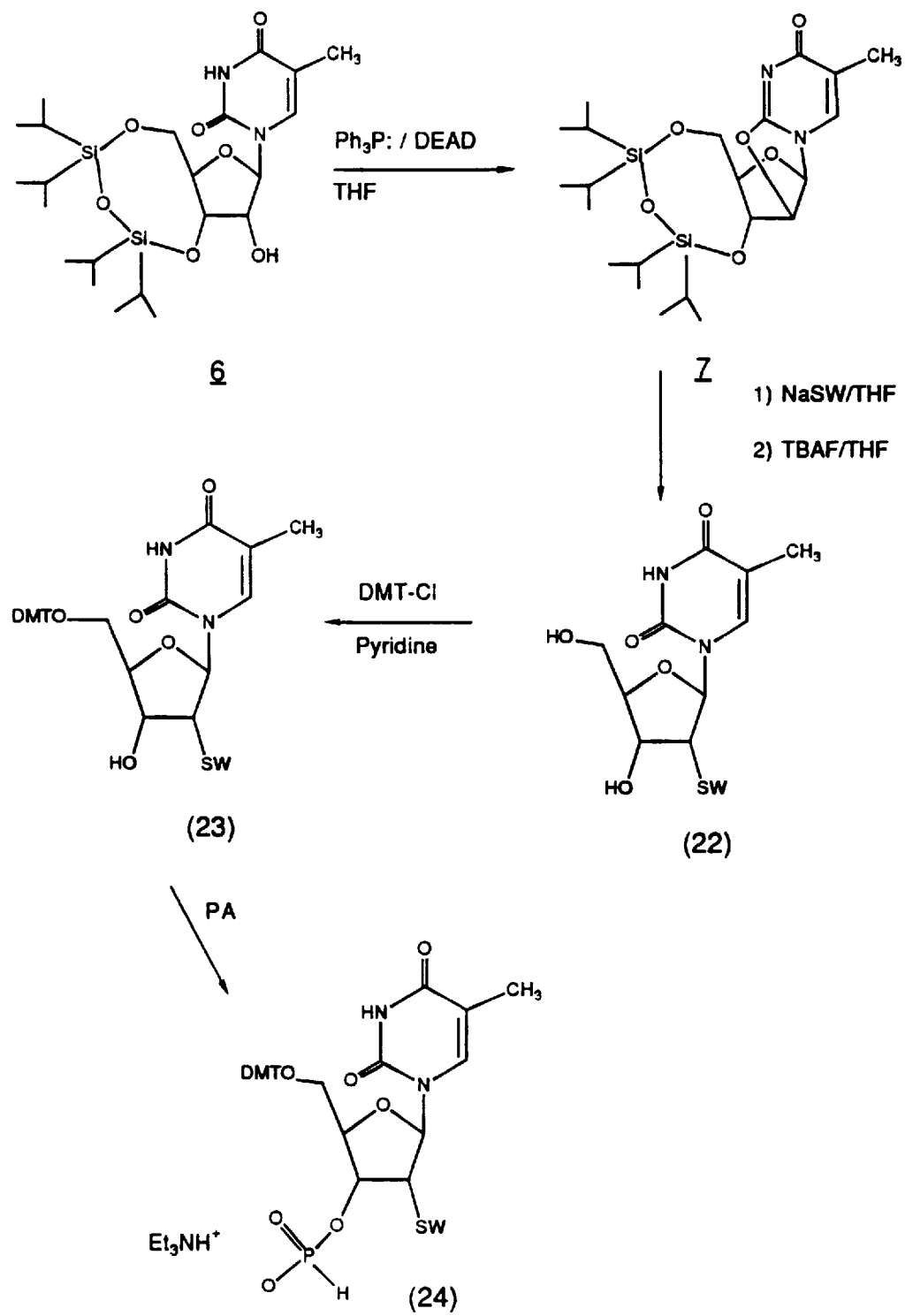
FIG. 6. Synthesis of monomers containing 2'-S-alkyl modifications.

Synthesis of 2'-thioalkyl nucleomonomers is accomplished as described in FIG. 6. The protocol is useful for synthesis of 2'-thioalkyl pyrimidines via formation of an anhydro intermediate 7 that is subsequently converted to thioalkyl nucleomonomer (22). The group designated W is defined as lower alkane (methyl, ethyl, propyl, isopropyl, butyl or isobutyl) or lower alkene including allyl. The protocol was used to synthesize 5'-DMT blocked 5-methyluridine 3'-H-phosphonate. The starting material 6 was obtained from 5-methyluridine (Markiewicz, W. T., *J. Chem. Res* (M) (1979) 0181–0197. Alternate blocking groups at the 5'- and 3'-positions, such as tetrahydropyran can also be utilized to obtain an equivalent starting material. The method shown in FIG. 6 can thus be used to synthesize 2'-thioalkyl derivatives of the nucleomonomers containing the modified bases of the present invention in addition to synthesis of other modified pyrimidine nucleomonomers such as 2'-thioalkylcytidine, 2'-thioalkylthymidine, 2'-thioalkyl-$N^4$—$N^4$-ethanocytidine or 2'-thioalkyluridine. Conversion of the nucleomonomer (22) to other 5'- and 3'-derivatized compounds such as MMT, β-cyanoethylphosphoramidite, or methylphosphoramidite-blocked nucleomonomers can easily be accomplished using appropriate reagents.

Dimer and Trimer Synthons for Oligomers Containing Substitute Linkages

Oligomers containing substitute linkages that link adjacent nucleomonomer analog residues are preferably synthesized using suitably blocked dimer synthons as a starting material. For dimers wherein one or both base residues are 5-$R^2$-U or 5-$R^2$-C or related analogs, synthesis of a formacetal or 3'-thioformacetal-linked dimer is accomplished as described herein. An exemplary dimer containing a formacetal linkage of formula (6) shown in FIG. 1, Y, X, B and $R^3$ are as defined herein.

Figure 7:
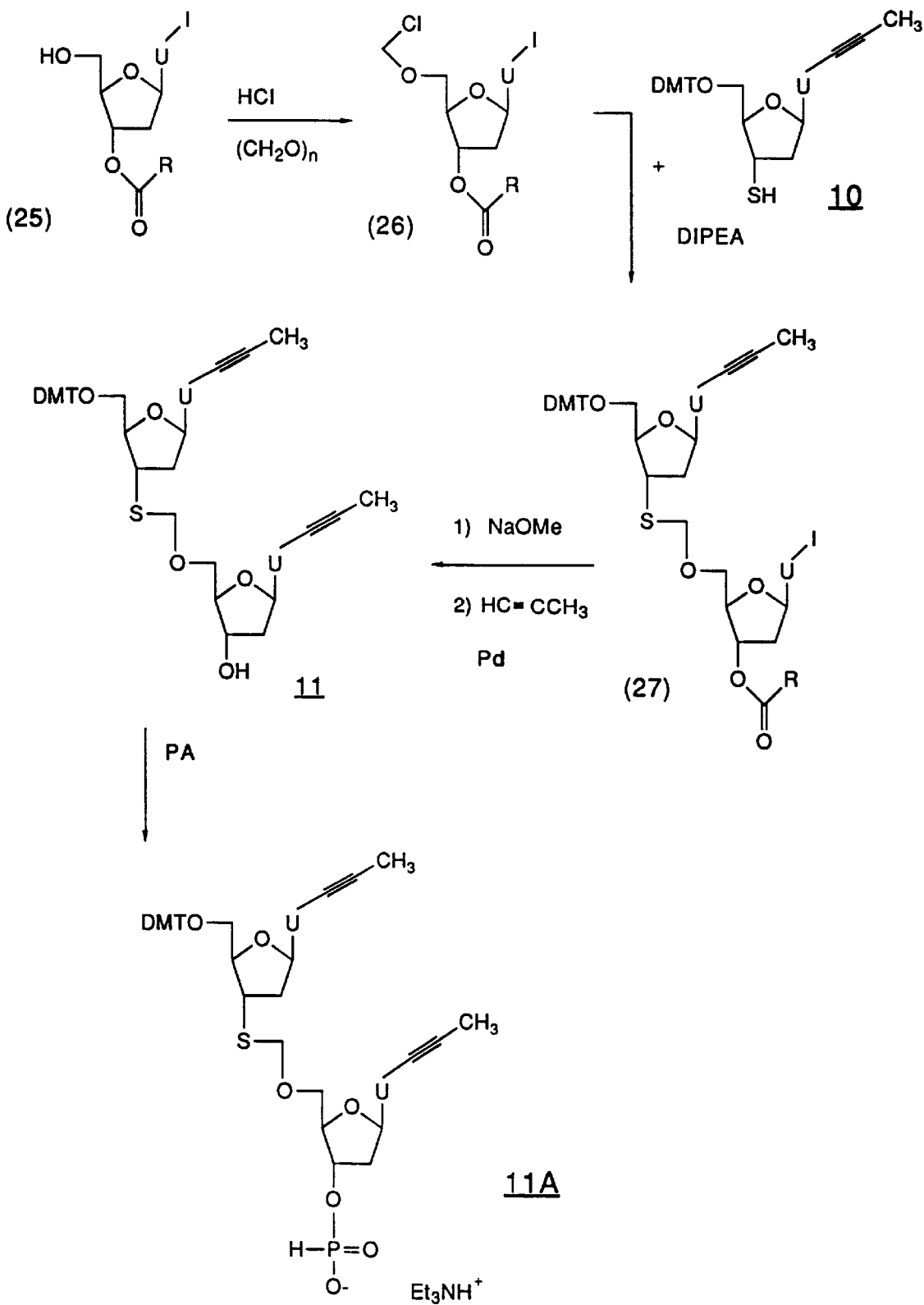
FIG. 7. Synthesis of dimer linked by a 3'-thioformacetal linkage (method #2).
Figures 1, 8:
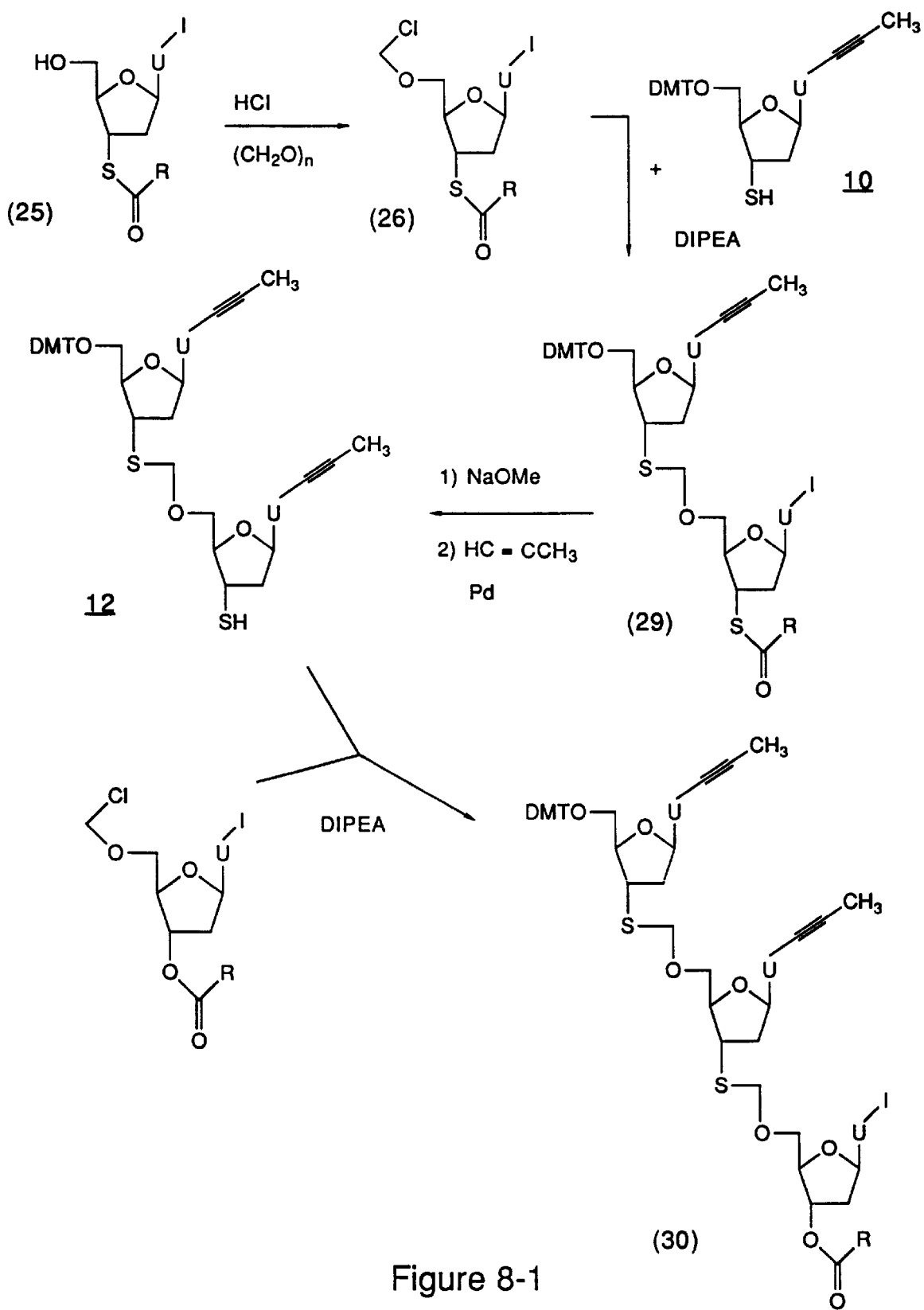
FIG. 8.
Figures 2, 8:
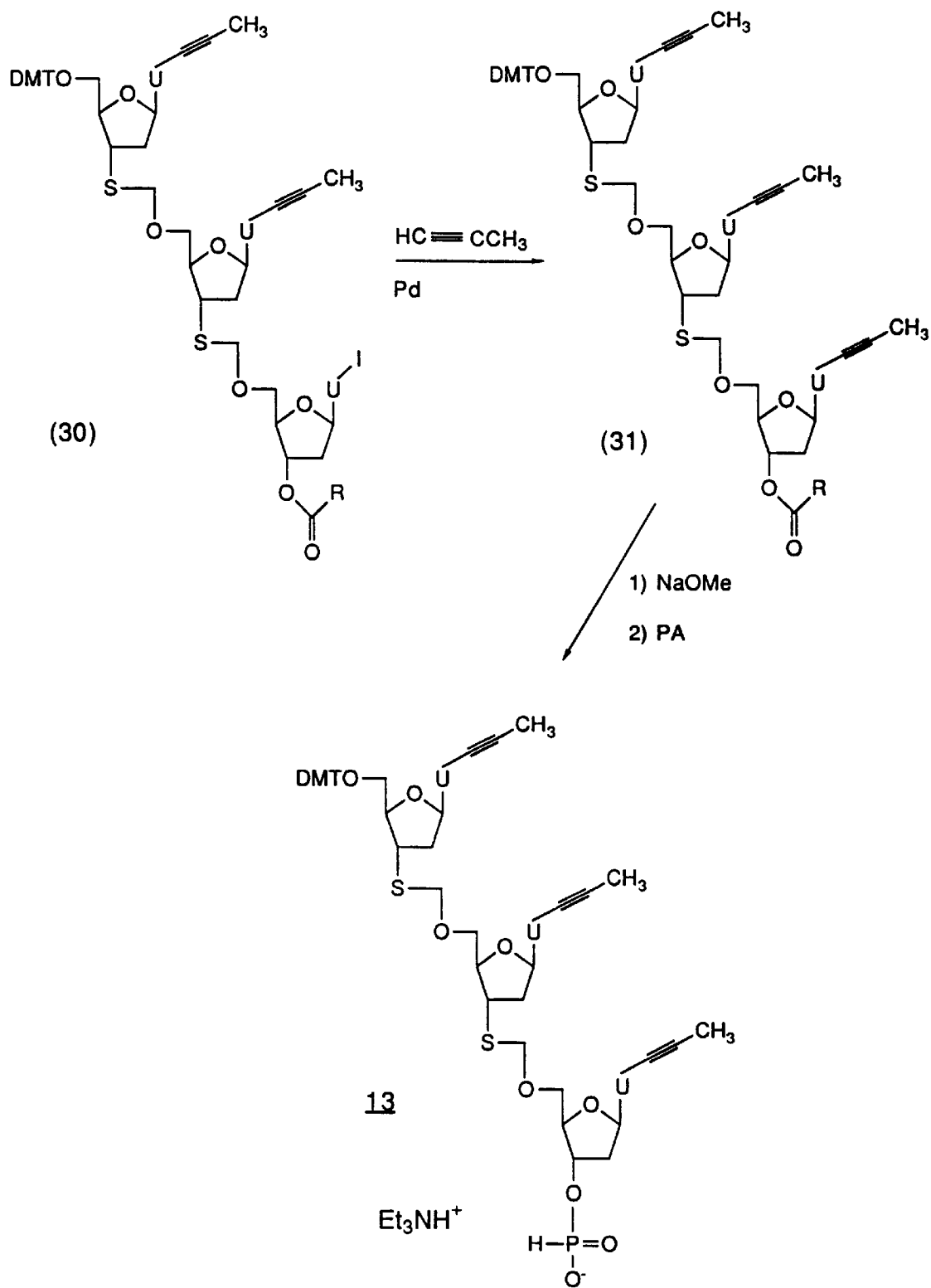

FIGS. 7 and 8 show synthesis schemes for intermediates in oligomer synthesis. In both Figures, the structure U-I represents 5-iodouracil and U—≡—CH$_3$ represents 5-(1-propynyl)uracil. Synthesis of a 3'-thioformacetal dimer or a trimer can conveniently be accomplished. As shown in FIG. 7, a 5-iodouridine nucleomonomer, (25), protected at the 3'-position by esterification is first reacted with paraformaldehyde in the presence of HCl to obtain the derivatized nucleomonomer, (26), containing the substituent ClCH$_2$-at the 5'-position. The nucleomonomer can be esterified using, for example, a long-chain alkyl or aromatic acid, such a decyl, hexyl, benzoyl, or phenoxyacetyl. In this first step, the 3'-esterified nucleomonomer is treated with an excess of paraformaldehyde in an inert solvent at low temperature and anhydrous HCl is bubbled through the reaction mixture. The solution is conveniently dried and the solvent removed to obtain the intermediate.

The intermediate, (26), shown as the chloro-methylether (ClCH$_2$O—) at the 5'-position of the nucleo-side, is then dissolved in an inert solvent. A solution of a second nucleomonomer (5-(1-propynyl)uridine derivative), 10, protected at the 5'-position, for example by DMT, and bearing an -SH substituent at the 3'-position along with a base, preferably diisopropylethylamine (DIPEA), in an inert solvent, is also prepared. The chloromethyl ether intermediate is added dropwise to this solution and the reaction mixture is stirred for several hours.

The reaction is washed with water, and the organic layer is separated and dried to obtain the dimerized product having the 3'—SCH$_2$O— 5' linkage and rotected at the 5'- and 3'-positions, as above. The resulting dimer is deprotected at the 3'-position and then converted to the propyne derivative as shown and described in Example 1. Where the dimer is to be used in standard oligomer synthesis, it is converted to the hydrogen phosphonate using 2-chloro-4H-1,2,3-benzodioxaphosphorin-4-one (van Boom's reagent for phosphytylation (PA)). FIG. 8 shows the synthesis of a 3'-thioformacetal trimer.

Figures 1, 9:
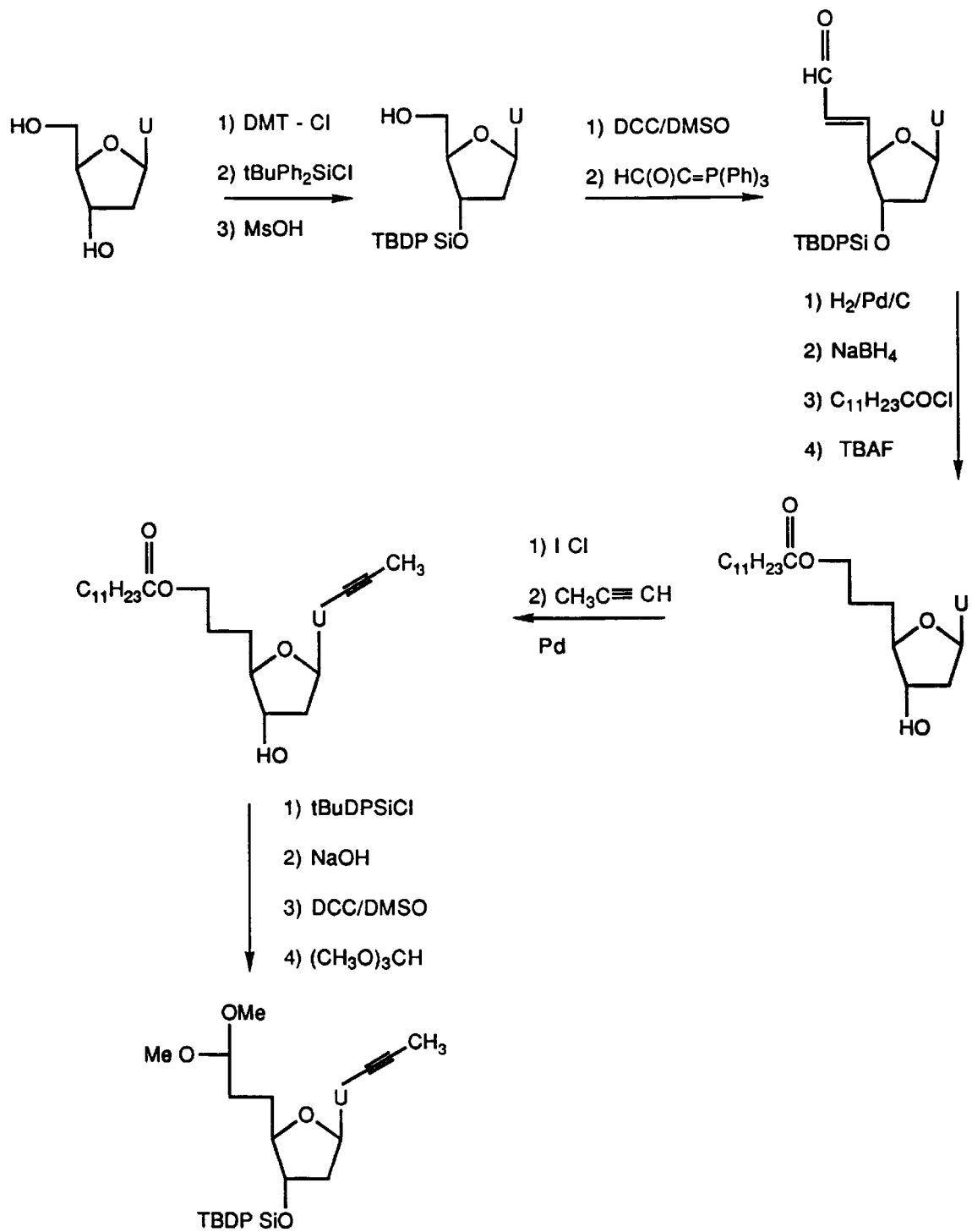
FIG. 9.
Figures 2, 9:
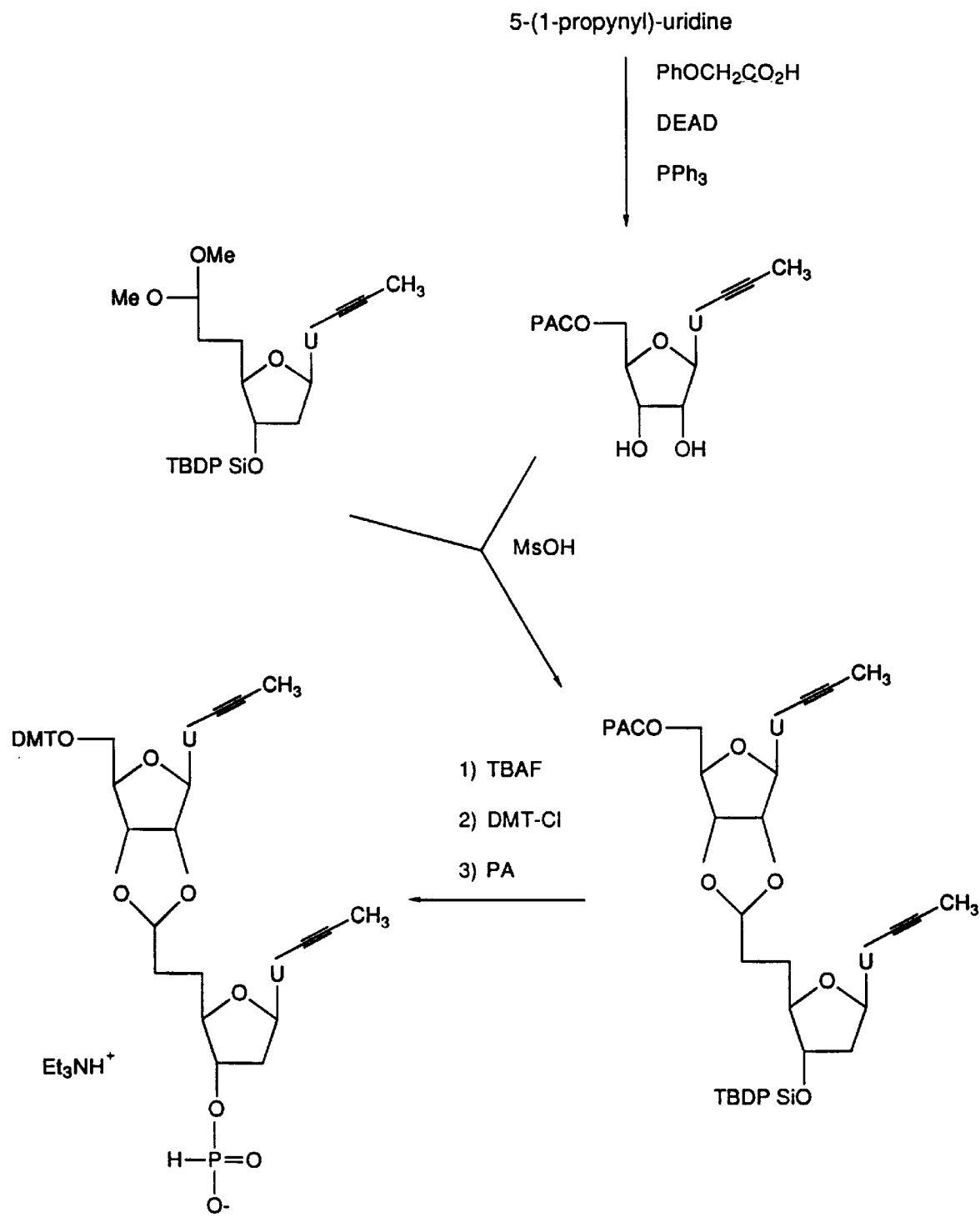

Synthesis of riboacetal linked dimers is shown in FIG. 9. 5'-DMT, 3'-H-phosphonate dimers can be directly utilized for incorporation into oligomers by conventional methods or an appropriate precursor can be utilized as needed for conversion to trimer, tetramer or longer length oligomers.

Synthesis of Ethynyl Heteroaryl and Heteroaryl Derivatized Bases

Figure 14:
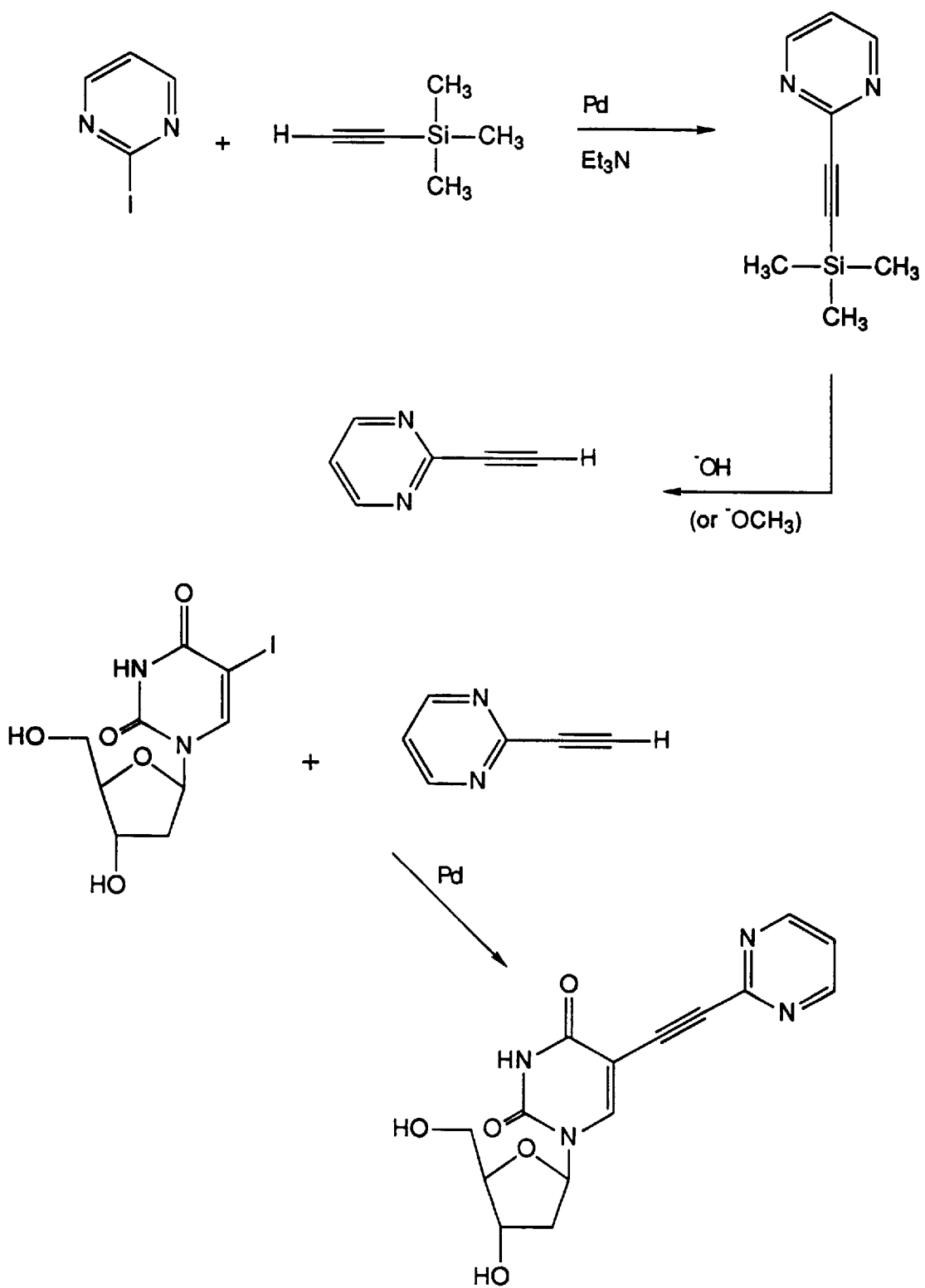
FIG. 14. Synthesis of the 5-((1-ethynyl)-2pyrimidinyl)-2'-deoxyuridine nucleomonomer.
Figure 15:
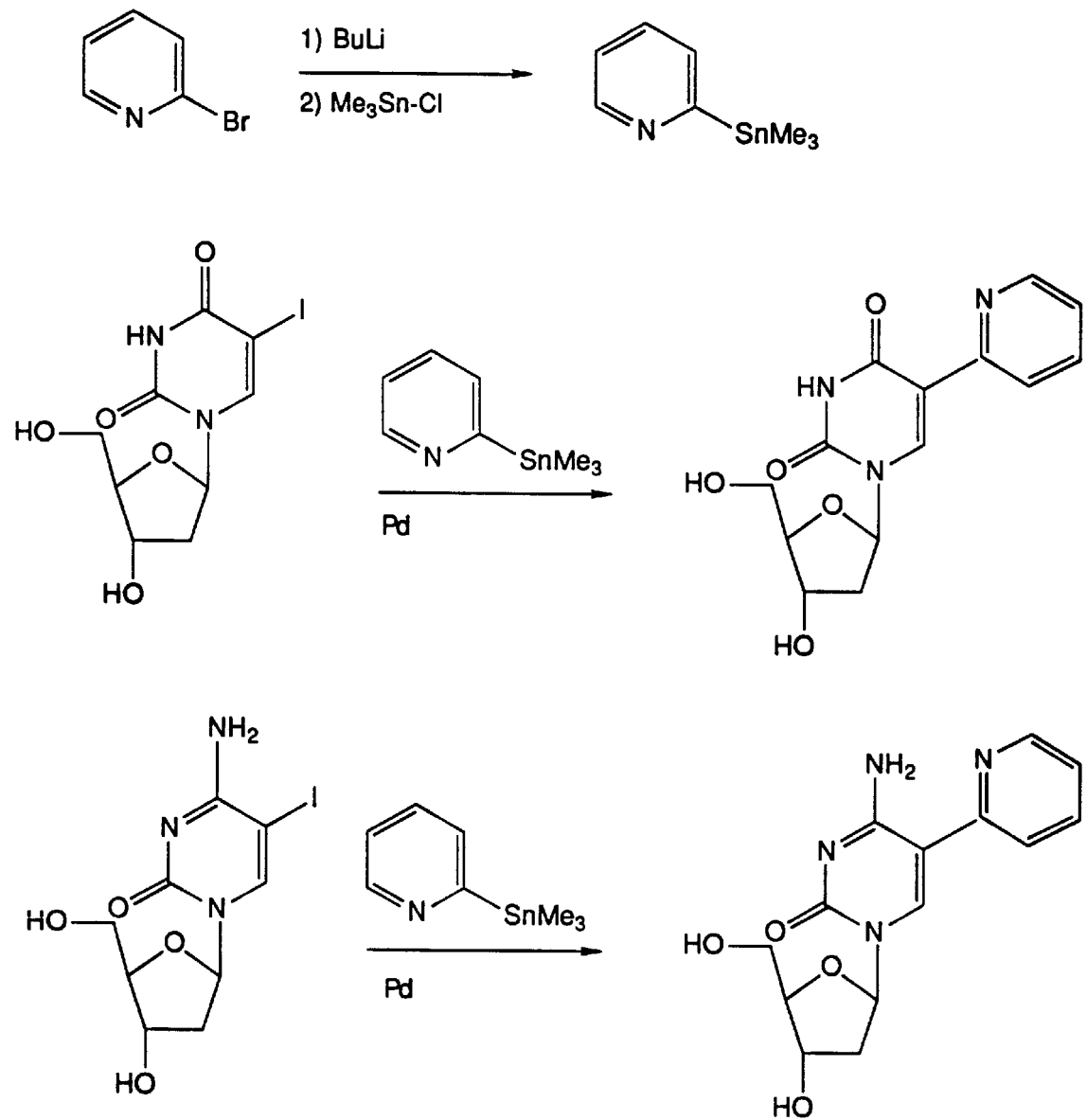
FIG. 15. Synthesis of 5-(2-pyridinyl)-2'-deoxyuridine and 5-(2-pyridinyl)-2'-deoxycytidine nucleomonomers.
Figure 16:
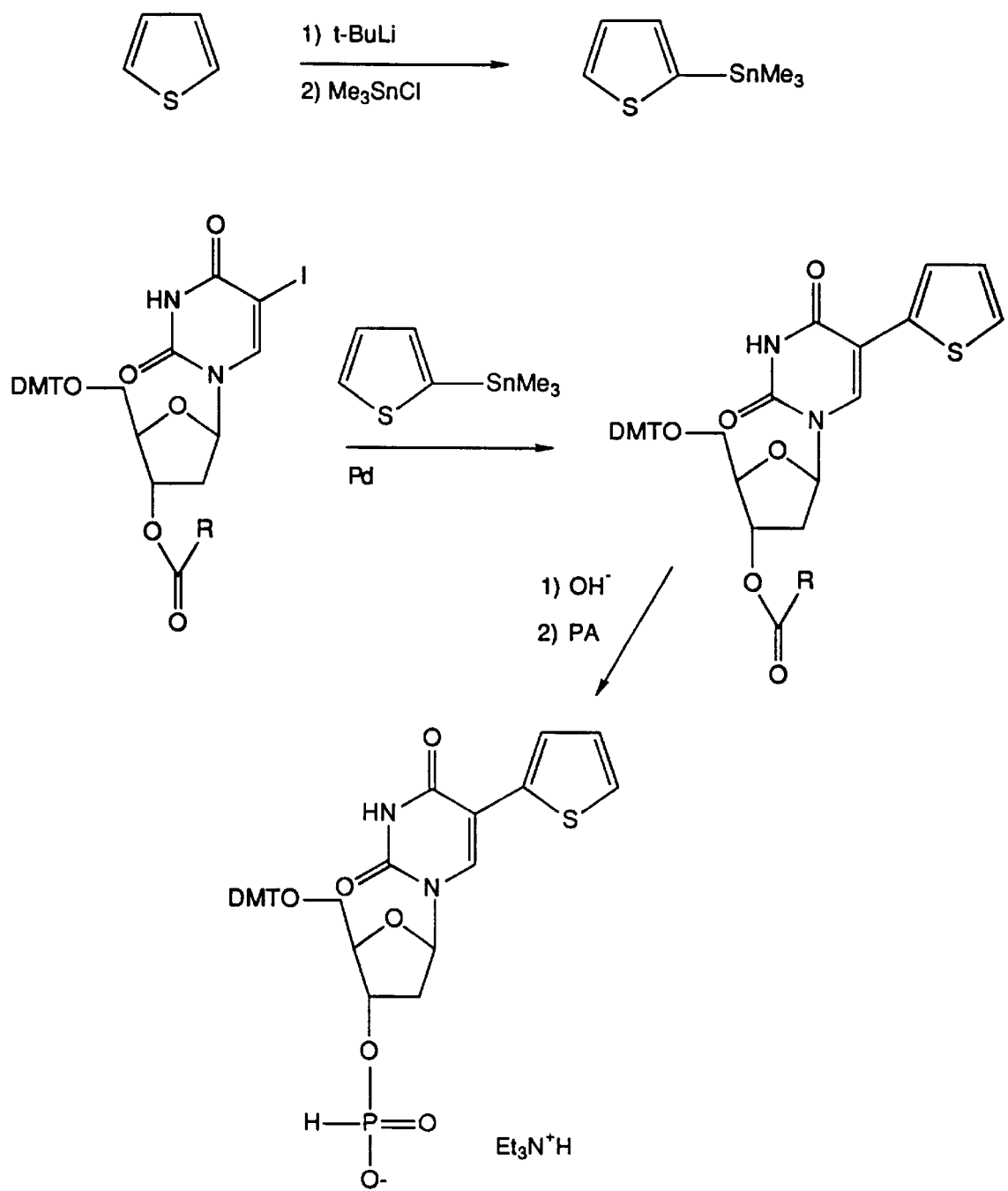
FIG. 16. Synthesis of 5-(2-thienyl)-2'-deoxyuridine derivative.

FIGS. 14, 15 and 16 show synthetic schemes for synthesis of nucleomonomers having invention bases with ethynyl heteroaryl or heteroaryl groups at the 5 position. The nucleomonomers can be converted to blocked monomers suitable for incorporation into oligomers by conventional methods.

Synthesis of 5-phenyl-2'-deoxyuridine was accomplished as previously described using phenyltrimethylstannane (crisp, G., et al., *Tetrahedron Letters* (1990) 31:1347–1350). An analogous protocol using pyridinyltrimethylstannane or pyridinyltributylstannane or the like as a starting material which is obtained from bromopyridine is used to synthesize 5-(2-pyridinyl)-2'-deoxyuridine (Example 15). Synthesis of heteroarylstannanes is conveniently accomplished as described (Bailey, T. R. *Tet Lett* (1986) 27:4407–4410; Jutzi, P. et al, *J. Organometal Chem.* (1983) 246:163–168; Molloy, K. C. et al, *J. Organometal Chem.* (1989) 365:61–73).

Synthesis of 5-substituted pyrimidine nucleomonomers with heteroaryl groups such as 2-thiazoyl, 1-methyl-2-imidazolyl, 2-oxazoyl, 2-furanyl and the like can be accomplished using a published protocol (Wigerinck, P. et al., *J Med Chem* (1991) 34:2383–2389; Peters, D., et al, *Nucleosides and Nucleotides* (1992) 11:1151–1173) followed by conversion to the corresponding nucleomonomer by standard methods (see Example 16). The 5-cyano substituent is prepared as described (Inoue, T., et al, *Chem Pharm Bull* (1978) 9:2657–2663) and also can be used as a starting electrophile to build heteroaryl substituted nucleomonomers as described (Wigerinck, P., et al, *J Med Chem* (1991) 34:1767–1772).

Ethynyl heteroaryl derivatives are prepared from ethynyltrimethylsilane and an appropriate heteroaryl as described (Austin, W. B., et al, *J Org Chem* (1981) 46:2280–2286)(see Example 14). The deprotected ethynyl is then introduced into the nucleomonomer by standard procedures (Examples 1 and 14).

Utility and Administration

As the oligomers of the invention are capable of significant single-stranded or double-stranded target nucleic acid binding activity to form duplexes, triplexes or other forms of stable association, these oligomers are useful in diagnosis and therapy of diseases that are associated with expression of one or more genes such as those associated with many different pathological conditions. Therapeutic applications can employ the oligomers to specifically inhibit the expression of genes (or inhibit translation of RNA sequences encoded by those genes) that are associated with either the establishment or the maintenance of a pathological condition. Exemplary genes or RNAs encoded by those genes that can be targeted include those that encode enzymes, hormones, serum proteins, adhesion molecules, receptor molecules, cytokines, oncogenes, growth factors, and interleukins. Target genes or RNAs can be associated with any pathological condition such as those associated with inflammatory conditions, cardiovascular disorders, immune reactions, cancer, viral infections, bacterial infections and the like.

Oligomers of the present invention are suitable for both in vivo and ex vivo therapeutic applications. Indications for ex vivo uses include treatment of cells such as bone marrow or peripheral blood in conditions such as leukemia or viral infection. Target genes or RNAs encoded by those genes that can serve as targets for cancer treatments include oncogenes, such as ras, k-ras, bcl-2, c-myb, bcr, c-myc, c-abl or overexpressed sequences such as mdm2, oncostatin M, IL-6 (Kaposi's sarcoma), HER-2 and translocations such as bcr/abl. Viral gene sequences or RNAs encoded by those genes such as polymerase or reverse transcriptase genes of CMV, HSV-1, HSV-2, HTLV-1, HIV-1, HIV-2, HBV, HPV, VZV, influenza virus, rhinovirus and the like are also suitable targets. Application of specifically binding oligomers can be used in conjunction with other therapeutic treatments. Other therapeutic indications for oligomers of the invention include (1) modulation of inflammatory responses by modulating expression of genes such as IL-1 receptor, IL-1, ICAM-1 or E-Selectin that play a role in mediating inflammation and (2) modulation of cellular proliferation in conditions such as arterial occlusion (restenosis) after angioplasty by modulating the expression of (a) growth or mitogenic factors such as non-muscle myosin, myc, fos, PCNA, PDGF or FGF or their receptors, or (b) cell proliferation factors such as c-myb. Other suitable extracellular proliferation factors such as TGFα, IL-6, γINF, protein kinase C may be targeted for treatment of psoriasis or other conditions. In addition, EGF receptor, TGFα or MHC alleles may be targeted in autoimmune diseases.

Delivery of oligomers of the invention into cells can be enhanced by any suitable method including calcium phosphate, DMSO, glycerol or dextran transfection, electroporation or by the use of cationic anionic and/or neutral lipid compositions or liposomes by methods described (International Publication Nos. WO 90/14074, WO 91/16024, WO 91/17424, U.S. Pat. No. 4,897,355). The oligomers can be introduced into cells by complexation with cationic lipids such as DOTMA (which can or can not form liposomes) which complex is then contacted with the cells. Suitable cationic lipids include but are not limited to N-(2, 3-di(9-(Z)-octadecenyloxyl))-prop-1-yl-N,N,N-trimethylammonium (DOTMA) and its salts, 1-O-oleyl-2-O-oleyl-3-dimethylaminopropyl-β-hydroxyethylammonium and its salts and 1,2-bis(oleyloxy)-3-(trimethylammonio)propane and its salts.

Enhanced delivery of the invention oligomers can also be mediated by the use of (i) viruses such as Sendai virus (Bartzatt, R., *Biotechnol Appl Biochem* (1989) 11:133–135) or adenovirus (Wagner, E., et al, *Proc Natl Acad Sci* (1992) 89:6099–6013; (ii) polyamine or polycation conjugates using compounds such as polylysine, protamine or N1, N12-bis(ethyl)spermine (Wagner, E., et al, *Proc Natl Acad Sci* (1991) 88:4255–4259; Zenke, M., et al, *Proc Natl Acad Sci* (1990) 87:3655–3659; Chank, B. K., et al, *Biochem Biophys Res Commun* (1988) 157:264–270; U.S. Pat. No. 5,138,045); (iii) lipopolyamine complexes using compounds such as lipospermine (Behr, J.-P., et al, *Proc Natl Acad Sci* (1989) 86:6982–6986; Loeffler, J. P., et al *J Neurochem* (1990) 54:1812–1815); (iv) anionic, neutral or pH sensitive lipids using compounds including anionic phospholipids such as phosphatidyl glycerol, cardiolipin, phosphatidic acid or phosphatidylethanolamine (Lee, K.-D., et al, *Biochim Biophys ACTA* (1992) 1103:185–197; Cheddar, G., et al, *Arch Biochem Biophys* (1992) 294:188–192; Yoshimura, T., et al, *Biochem Int* (1990) 20:697–706); (v) conjugates with compounds such as transferrin or biotin or (vi) conjugates with compounds such as serum proteins (including albumin or antibodies), glycoproteins or polymers (including polyethylene glycol) that enhance pharmacokinetic properties of oligomers in a subject. As used herein, transfection refers to any method that is suitable for delivery of oligomers into cells. Any reagent such as a lipid or any agent such as a virus that can be used in transfection protocols is collectively referred to herein as a "permeation enhancing agent". Delivery of the oligomers into cells can be via cotransfection with other nucleic acids such as (i) expressable DNA fragments encoding a protein(s) or a protein fragment or (ii) translatable RNAs that encode a protein(s) or a protein fragment.

The oligomers can thus be incorporated into any suitable formulation that enhances delivery of the oligomers into cells. Suitable pharmaceutical formulations also include those commonly used in applications where compounds are delivered into cells or tissues by topical administration. Compounds such as polyethylene glycol, propylene glycol, azone, nonoxonyl-9, oleic acid, DMSO, polyamines or lipopolyamines can be used in topical preparations that contain the oligomers.

The invention oligomers can be conveniently used as reagents for research or production purposes where inhibition of gene expression is desired. There are currently very few reagents available that efficiently and specifically inhibit the expression of a target gene by any mechanism. oligomers that have been previously reported to inhibit target gene expression frequently have nonspecific effects and/or do not reduce target gene expression to very low levels (less than about 40% of uninhibited levels). The invention oligomers are, by comparison, extremely potent with $IC_{50}$ values as low as 0.05 μM in microinjection assays (Example 6, Table 4 below). These levels of potency permit application of the oligomers to cells with efficient inhibition of target gene expression while avoiding significant nonspecific effects on the cell. In view of this, it is clear that the invention oligomers represent a unique class of reagents that can be used to probe gene function and to probe the role of single stranded or double stranded nucleic acids.

Thus, the results as described herein provide a method of inhibiting expression of a selected protein or proteins in a subject or in cells wherein the proteins are encoded by DNA sequences and the proteins are translated from RNA sequences, comprising the steps of: introducing an oligomer of the invention into the cells; and permitting the oligomer to form a triplex with the DNA or RNA or a duplex with the DNA or RNA whereby expression of the protein or proteins is inhibited. The methods and oligomers of the present invention are suitable for modulating gene expression in both procaryotic and eucaryotic cells such as bacterial, parasite, yeast and mammalian cells.

The results described below (Example 6 and 7) demonstrate that the oligomers, when used to inhibit gene expression by an antisense mechanism, can be RNase H "competent" or RNase H "incompetent" species. Oligomers having modifications such as 2'-substitutions (2'-O-allyl and the like) or certain uncharged linkages (methylphosphonate, phosphoramidate and the like) are usually incompetent as a substrate that is recognized by and/or acted on by RNase H. RNase H competence can facilitate antisense oligomer function by degrading the target RNA in an RNA-oligomer duplex (Dagle, J. M., et al, *Nucl Acids Res* (1990) 18:4751–4757; Walder, J. A. et al, International Publication Number WO 89/05358). The enzyme cleaves RNA in RNA-DNA duplexes.

In order to retain RNase H competence, an oligomer requires a RNase H competent domain of three or more competent contiguous linkages located within it (Quartin, R.

S., et al, *Nucl Acids Res* (1989) 17:7253–7262). Design of oligomers resistant to nuclease digestion will have terminal linkage, sugar and/or base modifications to effect nuclease resistance. Thus, the oligomers can be designed to have modified nucleomonomer residues at either or both the 5'- and/or 3'-ends, while having an internal RNase H competent domain.

Exemplary oligomers that retain RNase H competence would generally have uniform polarity and would comprise about 2 to about 12 nucleomonomers at the 5'-end and at the 3'-end which stabilize the oligomer to nuclease degradation and about three to about 26 nucleomonomers that function as a RNase H competent domain between the RNase H incompetent 3'- and 5'-ends. Variations on such an oligomer would include (1) a shorter RNase H competent domain comprising 1 or 2 RNase H competent linkages, (2) a longer RNase H incompetent domain comprising up to 15, 20 or more substitute linkages or nucleomonomers, (3) a longer RNase H competent domain comprising up to 30, 40 or more linkages, (4) oligomers with only a single RNase H incompetent domain at the 3' end or at the 5' end, or (5) oligomers having more than one RNase H competent domain. RNase H competence also applies as a consideration to oligomers having one or more regions of inverted polarity, to circular oligomers and to other types of oligomers. oligomers containing as few as about 8 nucleomonomers can be used to effect inhibition of target protein(s) expression by formation of duplex or triplex structures with target nucleic acid sequences. However, linear oligomers used to inhibit target protein expression via duplex or triplex formation will preferably have from about 12 to about 20 nucleomonomer residues.

Oligomers containing bases of the invention can be conveniently circularized as described (International Publication No. WO 92/19732; Kool, E. T. *J Am Chem Soc* (1991) 113:6265–6266; Prakash, G., et al. *J Am Chem Soc* (1992) 114:3523–3527). Such oligomers are suitable for binding to single-stranded or double-stranded nucleic acid targets. Circular oligomers can be of various sizes. Such oligomers in a size range of about 22–50 nucleomonomers can be conveniently prepared. The circular oligomers can have from about three to about six nucleomonomer residues in the loop region that separate binding domains of the oligomer as described (Prakash, G. ibid). Oligomers can be enzymatically circularized through a terminal phosphate by ligase or by chemical means via linkage through the 5'- and 3'-terminal sugars and/or bases.

The oligomers can be utilized to modulate target gene expression by inhibiting the interaction of nucleic acid binding proteins responsible for modulating transcription (Maher, L. J., et al, *Science* (1989) 245:725–730) or translation (Example 7 below). The oligomers are thus suitable as sequence-specific agents that compete with nucleic acid binding proteins (including ribosomes, RNA polymerases, DNA polymerases, translational initiation factors, transcription factors that either increase or decrease transcription, protein-hormone transcription factors and the like). Appropriately designed oligomers can thus be used to increase target protein synthesis through mechanisms such as binding to or near a regulatory site that transcription factors use to repress expression or by inhibiting the expression of a selected repressor protein itself.

The invention oligomers can be designed to contain secondary or tertiary structures, such as pseudoknots or pseudo-half-knots (Ecker, D. J., et al, *Science* (1992) 257:958–961). Such structures can have a more stable secondary or tertiary structure than corresponding unmodified oligomers. The enhanced stability of such structures would rely on the increased binding affinity between regions of self complementarity in a single oligomer or regions of complementarity between two or more oligomers that form a given structure. Such structures can be used to mimic structures such as the HIV TAR structure in order to interfere with binding by the HIV Tat protein (a protein that binds to TAR). A similar approach can be utilized with other transcription or translation factors that recognize higher nucleic acid structures such as stems, loops, hairpins, knots and the like. Alternatively, the invention oligomers can be used to (1) disrupt or (2) bind to such structures as a method to (1) interfere with or (2) enhance the binding of proteins to nucleic acid structures.

In addition to their use in antisense or triple helix therapies, the oligomers of the invention can also be applied as therapeutic or diagnostic agents that function by direct displacement of one strand in a duplex nucleic acid. Displacement of a strand in a natural duplex such as chromosomal DNA or duplex viral DNA, RNA or hybrid DNA/RNA is possible for oligomers with a high binding affinity for their complementary target sequences. Therapeutic applications of oligomers by this method of use, referred to herein as D-looping or "D-loop therapy" has not previously been possible because the affinity of natural DNA or RNA for its complementary sequence is not great enough to efficiently displace a DNA or RNA strand in a duplex. Therapeutic efficacy of oligomers that function by D-looping would result from high affinity binding to a complementary sequence that results in modulation of the normal biological function associated with the nucleic acid target. Types of target nucleic acids include but are not limited to (i) gene sequences including exons, introns, exon/intron junctions, promoter/enhancer regions and 5' or 3' untranslated regions, (ii) regions of nucleic acids that utilize secondary structure in order to function (e.g. the HIV TAR stem-loop element or tRNAs), (iii) nucleic acids that serve structural functions such as telomeres or centromeres and (iv) any other duplex region. It is clear that oligomers can be synthesized with discrete functional domains wherein one region of an oligomer binds to a target by D-looping while an adjacent region binds a target molecule by say, forming a triple helix or binding as an aptamer to a protein. Alternatively, a D-looping oligomer can bind to each strand in a duplex by switching the strand to which the oligomer binds (i.e. by having one region of the oligomer that binds to one strand and another region that binds to the complementary strand). The controlling elements that dictate the mode of binding (i.e. triple helix or D-loop) are the sequence of the oligomer and the inherent affinity built into the oligomer. Base recognition rules in Watson-Crick duplex binding differ from those in Hoogsteen controlled triplex binding. Because of this, the oligomer base sequence can be used to dictate the type of binding rules an oligomer will utilize.

D-loop structures are formed in nature by enzyme-mediated processes (Harris, L. D. et al., *J Biol Chem* (1987) 262: 9285–9292) or are associated with regions where DNA replication occurs (Jacobs, H. T. et al., *Nucl Acids Res* (1989) 17:8949–8966). D-loops that arise from the binding of oligomers can result from a one or two step process. Direct displacement of a target strand will give rise to a D-loop by a single binding event. However, D-looping can also occur by forming a triple helix which facilitates a strand displacement event leading to the D-loop.

Ribozymes containing bases of the invention can be designed in order to design species with altered characteristics. Ribozymes that cleave single stranded RNA or DNA (Robertson, D. L., et al *Nature* (1990) 344:467–468) have been described. Therapeutic applications for ribozymes have been postulated (Sarver, N. et al, *Science* (1990) 247:1222–1225; International Publication Number WO 91/04319). Secondary or tertiary structure necessary for ribozyme function can be affected by design of appropriate oligomer sequences. For example, ribozymes having targeting domains containing bases of the invention will have higher affinity, while maintaining base pairing specificity, for target sequences. Because of the higher affinity of the invention bases for their complementary sequences, shorter recognition domains in a ribozyme (an advantage in manufacturing) can be designed which lead to more favorable substrate turnover (an advantage in ribozyme function).

In therapeutic applications, the oligomers are utilized in a manner appropriate for treatment of a variety of conditions by inhibiting expression of appropriate target genes. For such therapy, the oligomers can be formulated for a variety of modes of administration, including systemic, topical or localized administration. Techniques and formulations generally can be found in *Remington's Pharmaceutical Sciences*, Mack Publishing Co., Easton, Pa., latest edition. The oligomer active ingredient is generally combined with a carrier such as a diluent or excipient which can include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers can be formulated in solid form and redissolved or suspended immediately prior to use. Lyophilized forms are also included. Dosages that can be used for systemic administration preferably range from about 0.01 mg/Kg to 50 mg/Kg administered once or twice per day. However, different dosing schedules can be utilized depending on (i) the potency of an individual oligomer at inhibiting the activity of its target DNA or RNA, (ii) the severity or extent of a pathological disease state associated with a given target gene, or (iii) the pharmacokinetic behavior of a given oligomer.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents can be used to facilitate permeation. Transmucosal administration can be through use of nasal sprays, for example, or suppositories. For oral administration, the oligomers are formulated into conventional oral administration forms such as capsules, tablets, and tonics.

For topical administration, the oligomers of the invention are formulated into ointments, salves, gels, or creams, as is generally known in the art. Formulation of the invention oligomers for ocular indications such as viral infections would be based on standard compositions known in the art.

In addition to use in therapy, the oligomers of the invention can be used as diagnostic reagents to detect the presence or absence of the target nucleic acid sequences to which they specifically bind. The enhanced binding affinity of the invention oligomers is an advantage for their use as primers and probes. Diagnostic tests cab be conducted by hybridization through either double or triple helix formation which is then detected by conventional means. For example, the oligomers can be labeled using radioactive, fluorescent, or chromogenic labels and the presence of label bound to solid support detected. Alternatively, the presence of a double or triple helix can be detected by antibodies which specifically recognize these forms. Means for conducting assays using such oligomers as probes are generally known.

The use of oligomers containing the modified bases as diagnostic agents by triple helix formation is advantageous since triple helices form under mild conditions and the assays can thus be carried out without subjecting test specimens to harsh conditions. Diagnostic assays based on detection of RNA for identification of bacteria, fungi or protozoa sequences often require isolation of RNA from samples or organisms grown in the laboratory, which is laborious and time consuming, as RNA is extremely sensitive to ubiquitous nucleases.

The oligomer probes can also incorporate additional modifications such as modified sugars and/or substitute linkages that render the oligomer especially nuclease stable, and would thus be useful for assays conducted in the presence of cell or tissue extracts which normally contain nuclease activity. Oligomers containing terminal modifications often retain their capacity to bind to complementary sequences without loss of specificity (Uhlmann et al., *Chemical Reviews* (1990) 90:543–584). As set forth above, the invention probes can also contain linkers that permit specific binding to alternate DNA strands by incorporating a linker that permits such binding (Froehler, B. C., et al, *Biochemistry* (1992) 31:1603–1609); Horne et al., *J Am Chem Soc* (1990) 112:2435–2437).

Incorporation of base analogs of the present invention into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al., *Nucleic Acids Res* (1986) 14:9943).

Oligomers of the invention are suitable for use in diagnostic assays that employ methods wherein either the oligomer or nucleic acid to be detected are covalently attached to a solid support as described (U.S. Pat. No. 4,775,619). The oligomers are also suitable for use in diagnostic assays that rely on polymerase chain reaction techniques to amplify target sequences according to described methods (European Patent Publication No. 0 393 744). oligomers of the invention containing 5-modified pyrimidines are compatible with polymerases used in polymerase chain reaction methods such as the Taq or Vent™ polymerase. Oligomers of the invention can thus be utilized as primers in PCR protocols or triphosphate pyrimidine monomers having $R^2$ at the 5-position can be utilized as a substrate by DNA or RNA polymerases derived from thermophiles (Taq or Vent™) or other sources (*E. coli*, human, retrovirus, etc) to generate the oligomers of the invention in various diagnostic protocols. Synthesis of monomer triphosphates is accomplished by known methods (Otvos, L., et al, *Nucl Acids Res* (1987) 15:1763–1777).

The oligomers are useful as primers that are discrete sequences or as primers with a random sequence. Random sequence primers are generally about 6 or 7 nucleomonomers in length. Such primers can be used in various nucleic acid amplification protocols (PCR, ligase chain reaction, etc) or in cloning protocols. The 5-substitutions of the invention generally do not interfere with the capacity of the oligomer to function as a primer. Oligomers of the invention having 2'-modifications at sites other than the 3' terminal residue, other modifications that render the oligomer RNase H incompetent or otherwise nuclease stable can be advantageously used as probes or primers for RNA or DNA sequences in cellular extracts or other solutions that contain nucleases. Thus, the oligomers can be used in protocols for amplifying nucleic acid in a sample by mixing the oligomer with a sample containing target nucleic acid, followed by hybridization of the oligomer with the target nucleic acid and amplifying the target nucleic acid by PCR, LCR or other suitable methods.

The oligomers derivatized to chelating agents such as EDTA, DTPA or analogs of 1,2-diaminocyclohexane acetic acid can be utilized in various in vitro diagnostic assays as described (U.S. Pat. Nos. 4,772,548, 4,707,440 and 4,707,352). Alternatively, oligomers of the invention can be derivatized with crosslinking agents such as 5-(3-iodoacetamidoprop-1-yl)-2'-deoxyuridine or 5-(3-(4-bromobutyramido)prop-1-yl)-2'-deoxyuridine and used in various assay methods or kits as described (International Publication No. WO 90/14353).

In addition to the foregoing uses, the ability of the oligomers to inhibit gene expression can be verified in in vitro systems by measuring the levels of expression in subject cells or in recombinant systems, by any-suitable method (Graessmann, M., et al., *Nucleic Acids Res* (1991) 19:53–59).

All references cited herein are incorporated herein by reference in their entirety.

The following examples are intended to illustrate, but not to limit, the invention. Efforts have been made to insure accuracy with respect to numbers used (e.g., amounts, temperatures, etc.), but some experimental errors and deviations should be taken into account. Unless indicated otherwise, parts are parts by weight, temperature is in degrees Centigrade, and pressure is at or near atmospheric.

EXAMPLE 1

Synthesis of 5-(1-Propynyl)-2'-Deoxyuridine H-Phosphonate Monomer and Oligomers Containing the Analog In a 50 mL round bottom flask is placed:
a) 708 mg (2 mmole) 5-iodo dU
b) 10 mL anhydrous DMF
c) 76 mg (0.4 mmole) CuI
d) 555 $\mu$L (4 mmole) Et$_3$N
e) 231 mg (0.2 mmole)(Ph$_3$P)$_4$Pd
f) saturate with propyne gas with stirring at room temperature (approx. 10 min.).

After 2 hours, more propyne gas is bubbled in and the reaction mixture is stirred overnight at room temperature. The following morning more propyne is bubbled in and stirred for an additional 2 hrs. To the reaction mixture is added Dowex ion-exchange resin (HCO$_3$-form), 10 mL of MeOH and 10 mL of CH$_2$Cl$_2$ and stirring continued for 1 hr. The resin is filtered off, washed with MeOH and the supernatant evaporated. Silica Gel chromatography yielded 517 mg (1.94 mmole, 97% yield) of product. See: Hobbs, *J Org Chem* (1989) 54:3420–3422.

The purified material was protected with a 5' DMT and phosphitylated as described (Marugg, J. E., et al, *Tetrahedron Letters* (1986) 27:2661–2664) and used in solid phase synthesis as described (Froehler, B. C., et al, U.S. Pat. No. 4,959,463; Froehler, B. C., et al, *Tetrahedron Letters* (1986) 27:5575–5578).

The following notation is used to represent the bases in the designated numbered oligomers in the Examples below: A, T, G, C, and U have their conventional meanings. C'=5-methyl-2'-deoxycytidine, C*=5-(1-propynyl)-2'-deoxycytidine; U*=5-(1-propynyl)-2'-deoxyuridine.

EXAMPLE 2

Formation of Triple Helix Structures Using Oligomers (ON) Containing 5-Propynyl Uracil Residues that Bind to Duplex DNA Three oligomers were synthesized as follows:
ON-1 5'TC'TC'TC'TC'TC'TTTTT 3' (SEQ ID NO:1)
ON-2 5'TC'TC'TC'TC'TC'U*U*U*U*U* 3' (SEQ ID NO:2)
ON-3 5'TC'TC'TC'U*C'U*C'U*TU*TU* 3' (SEQ ID NO:3)

Each oligomer (ON) was hybridized with duplex DNA containing the target sequence 5'AGAGAGAGAGAAAAA 3' (SEQ ID NO:4). Hybridization was carried out in 140 mM KCl, 5 mM MgCl$_2$, 5 mM Na$_2$HPO$_4$, pH 6.6. Thermal stability, $T_m$, of the resulting triple helix formed between each oligomer and the target sequence was determined. The following $T_m$ values were obtained, ON-1 (control oligomer) was 42.1° C., ON-2 was 48.1° C. and ON-3 was 55° C. The increased $T_m$ values of ON-2 and ON-3 were not expected and demonstrated that the triple helix formed was more stable than the corresponding control triple helix structure.

EXAMPLE 3

Binding of Oligomers Containing 5-Propynyl Uracil or 5-Propynyl Cytosine to Single-Stranded RNA Oligomers were synthesized as follows:
ON-1 5' TC'TC'TC'TC'TC'TTTTT 3' (SEQ ID NO:1)
ON-3 5' TC'TC'TC'U*C'U*C'U*TU*TU* 3' (SEQ ID NO:3)
ON-4 5' TC*TC*TC*TC*TC*TTTTT 3' (SEQ ID NO:5)

The oligomers were hybridized with a single-stranded target RNA sequence, 5' AAAAAGAGAGAGAGA 3'(SEQ ID NO:6), in 140 mM KCl, 5 mM MgCl$_2$, 5 mM Na$_2$HPO$_4$, pH 6.6. The following $T_m$ values for the duplexes were obtained; ON-1 (control) was 65.5° C., ON-3 was 74.0° C. and ON-4 was 73.0° C. Duplexes formed with ON-3 and ON-4 were more stable than the control oligomer. Surprisingly, ON-3 and ON-4 gave increased $T_m$ values which demonstrated that the duplex formed was more stable than the corresponding control duplex structure.

EXAMPLE 4

Formation of Triple Helix Structures at Elevated pH

Triple helix formation at elevated pH was demonstrated using ON-1 as a control and ON-5, 5'U*C'U*C'U*C'U*C'U*C'U*U*U*U*U* 3' (SEQ ID NO:7). Oligomers were hybridized with duplex target DNA, as described in Example 2 except that the buffer was at pH 7.4. $T_m$ values of the triple helix were then determined. ON-1 had a $T_m$ of 27.1 while ON-5 had a $T_m$ of 51.5. Thus, oligomers containing 5-propynyl uracil were capable of triplex formation at high pH levels, while the control oligomer formed triplex structure only at temperatures that are below physiological.

In an additional set of determinations, modified forms of ON-5 wherein the 5-substituent of the deoxyuridine was, instead of propynyl, 3-methylbutynyl (ON-5A) or 3,3-dimethyl butynyl (ON-5B), similar affects on the melting temperature of duplex and triple helices were observed. The results are shown in Table 1 below:

TABLE 1

|  | Duplex[a] | | Triple-helix[a] | |
| --- | --- | --- | --- | --- |
|  | RNA | DNA | @ pH = 6.60 | |
|  | $T_m$ (°C.) | $T_m$ (°C) | $T_m$ (°C.) | $\Delta T_m$ (°C.) |
| ON-1 | 63.0 | 54.5 | 39.6 | — |
| ON-5 | 79.0 | 65.5 | 64.8 | +25.2 |
| ON-5A | 73.5 | 65.5 | 55.9 | +16.3 |
| ON-5B | 68.5 | 66.0 | 42.5 | +2.9 |

[a]$T_m$ in 140 mM KCl/5 mM Na$_2$PO$_4$/1 mM MgCl$_2$, pH 6.60.

EXAMPLE 5

Synthesis of 5-(3-Methyl-1-Butynyl)-2'-Deoxyuridine H-Phosphonate, Oligomers Containing the Analog and Formation of Triple Helix Structures Using the Oligomers 5-(3-Methyl-1-butynyl)-2'-deoxyuridine H-phosphonate was synthesized from 5-iododeoxyuridine essentially as described for 5-(1-propynyl)-2'-deoxyuridine H-phosphonate in Example 1, except that 5 equivalents of 3-methyl-1-butyne liquid was used in place of propyne. Silica gel purified material was then converted to the 5'-DMT, 3'-H-phosphonate monomer and used in solid phase synthesis to generate oligomers as follows (ON-1 was used as a control containing thymine and 5-methylcytosine as described in Example 2):

ON-1 5' TC'TC'TC'TC'TC'TTTTT 3' (SEQ ID NO:1)
ON-6 5' TC'TC'TC'U'C'U'CU'TU'TU'3' (SEQ ID NO:8)
ON-7 5' TC'TC'TC'TC'TC'U'U'U'U'U' 3(SEQ ID NO:9)

Base residues designated U' correspond to 5-(3-methyl-1-butynyl)uracil. The oligomers were hybridized with duplex DNA containing the target sequence, 5' AGAGAGAGAGAAAAA 3' (SEQ ID NO:4). Hybridization was carried out in the buffer described in Example 2 at pH 6.2. ON-1 had a $T_m$ of 51.0° C. while the $T_m$ of ON-6 was 55.2° C. and that of ON-7 was 55.0° C.

EXAMPLE 6

Stability of Duplex and Triplex Structures and Inhibition of Target Gene Expression Thermal stability. Additional oligomers were tested with respect to thermal denaturation or stability ($T_m$) after hybridization with DNA or RNA targets to form triplex or duplex structures respectively. The DNA target used was an oligomer containing a self-complementary region and having a 4 nucleotide loop at the end of the hairpin. The targets were as follows:

DNA Duplex Target: 5' AGAGAGAGAGAAAAAGGA$^T$ T (SEQ ID NO:10) 3' TCTCTCTCTCTTTTTCCT $_T$ T (SEQ ID NO:11)

RNA Target: 5' AAAAAGAGAGAGAGA 3' (SEQ ID NO:12)

The assays for triple-helix binding were conducted in 140 mM KCL/5 mM Na$_2$HPO$_4$/5 mM MgCL$_2$ at pH=6.60 and the final concentration of all oligomers was ~2 $\mu$M.

ON-1, set forth above, was used as a control.

Test oligomers 8–10 contain substitutions of 5-propynyluracil for thymine and 5-propynylcytosine for methylcytosine.

ON-8 5'-TC'TC'TC'U*C'U*C'U*TU*TU* 3' (SEQ ID NO:3)
ON-9 5'-TC*TC*TC*TC*TC*TTTTT 3' (SEQ ID NO:1)
ON-10 5'-U*C*U*C*U*C*U*C*U*C*U*U*U*U*U* 3(SEQ ID NO:13)

The results obtained showed that, with respect to triple-helix formation, the control ON-1 gave a $T_m$ of 43.4° C.; ON-8 gave an elevated $T_m$ of 55.5° C.; and ON-9 gave a $T_m$ of 26.3° C. ON-8 containing U*, showed an increase in $T_m$ of 2.4° C./substitution ($\Delta T_m$@6.6=+12.1° C.) relative to ON-1 and ON-9, containing C*, showed a decrease in $T_m$ of 3.4° C./substitution ($\Delta T_m$@6.6=−17.1° C.) relative to ON-1. The $T_m$ of a triple-helix, in which the third strand contains 2'-deoxycytidines, is pH dependent, and the $T_m$ at different pH values (from 5.8 to 7.4) was used to examine the pH dependence of the complex. With all ON's the slope of the plot remained relatively constant (−18° to −20° C./pH unit).

The low $T_m$ of ON-9, relative to ON's 1 and 8, can be explained in terms of basicity of the heterocycle. Titration of the hydrocholoride salt of C* and C' showed that the pKa of the 5-propyne analog C* (3.30,±0.05) is 1.05 units less than the 5-methyl derivative C' (4.35,±0.05). The importance of protonation in triple-helix formation has been demonstrated and the results above indicate that a decrease in basicity of the cytosine nucleobase has a dramatic effect on the stability of the complex. Surprisingly, the large difference in pKa's of the cytosines (C* and C') has no significant effect on the slope of the $T_m$ vs pH plot.

With respect to oligomer/RNA duplex formation, the control, ON-1 had a $T_m$ of 65.5° C., ON-8 had a $T_m$ of 74.0° C., ON-9 had a $T_m$ of 73.0° C. and ON-10 had a $T_m$ of more than 90° C.; ON-8 containing U', results in an increase in $T_m$ of 1.7° C./substitution and ON-9, containing C*, results in an increase in $T_m$ of 1.5° C./substitution. Under these conditions ON-10, containing complete substitution with U* and C*, has a $T_m$ greater than 90° C. (approx. 1.7° C./substitution) indicating that the increases in binding affinity of these substitutions are additive. These results show that the double-helix complex is greatly stabilized by substitution with both C* and U* and, therefore, these analogs represent a new class of useful antisense ON's.

Binding assays were conducted using a combination of C* and U* in oligomers containing phosphorothioate internucleotide linkages as an additional modification. Phosphorothioate linkages render oligomers nuclease stable, but reduce binding affinity for complementary target sequences relative to unmodified phosphodiester linkages. Other phosphodiester linkage analogs known in the art such as alkylphosphonate, methylphosphonate, phosphoroamidate and triester linkages suffer from similar limitations. Unexpectedly, oligomers containing a heterocycle modification that enhances binding affinity (defined herein as a positive modification), such as U* or C*, and a modification that reduces affinity (defined herein as a negative modification), were found to have improved binding (i.e. a greater binding affinity than predicted by the additive effects—positive and negative—of both modifications), relative to oligomers containing only the negative modification. Surprisingly, the propyne modification counteracts the negative binding effect of the phosphorothioate linkages to an unexpected degree. That is, for oligomers containing T and C' the $\Delta T_m$ between phosphodiester and phosphorothioate is 14° C. (0.7° C. per substitution) while the $\Delta T_m$ with U* and C* is 6.0° C. (0.3° C. per substitution). These results clearly demonstrate a synergistic effect between the negative modification (substitute linkage such as phosphorothioate) and the positive modification (base analog such as a 5-substituted pyrimidine) wherein the ositive modification compensated to a degree that is ore than additive with respect to binding affinity.

Binding results ($\Delta T_m$ relative to phosphodiester linkages) that were obtained are shown in Table 2 below:

sion vector for SV40 T antigen. Oligomers (ON-11 through ON-17) designed to target a sequence in the coding region were employed. The oligomers used in this assay were as follows:

ON 11: 5' ATTTTC'TTC'ATTTTTTC'TTC' 3' (SEQ ID NO:14)

ON 12: phosphorothioate form of ON-11

ON 13: 5' AU*U*U*U*C*U*U*C*AU*U*U*U*U*U* C*U*U*C* 3' (SEQ ID NO:7)

ON 14: phosphorothioate form of ON-13

ON 15: phosphorothioate 5' C*U*U*C*AU* U*U*U*U*U*C*U*U*C 3' (SEQ ID NO:18)

ON 16: phosphorothioate 5' C*U*U*C* AU*U*U*U*U*U*C*U* 3'(SEQ ID NO:19)

TABLE 2

| ON | ON Linkage | | |
|---|---|---|---|
| | Diester | Thioate | $\Delta T_m$ |
| ATTTTC'TTC'ATTTTTTC'TTC' (SEQ ID NO: 14) | 54.0 | 40.0 | −14.0 |
| AU*U*U*C'U*U*C'AU*U*U*U*U*C'U*U*C' (SEQ ID NO: 15) | 76.5 | 68.6 | −8.0 |
| AU*U*U*C*U*U*C*AU*U*U*U*U*C*U*U*C* (SEQ ID NO: 16) | 82.5 | 76.5 | −6.0 |

Additional data obtained in vitro with respect to duplex formation with target RNA corresponding to T antigen (TAg) show that the binding of the oligomer to the target is sequence-specific for the 5-substituted oligomers of the invention. The additional oligomers, 21 and 22, were prepared; ON-22 is a scrambled form of ON-21 which is designed to target the T antigen coding region as described above.

ON-21: AU*U*U*U*C'U*U*C'AU*U*U*U*U* C'U*U*C' (SEQ ID NO:15)

ON-22: U*U*AU*U*AU*C'U*U*C'U*U*C'U* U*U*U*C' (SEQ ID NO:25)

The oligomers were tested in phosphodiester (ON-21, ON-22) and phosphorothioate (ON-21A, ON-22A) form; and ON-21B and ON-22B the 2'-O-allyl T and C' oligomers. The results are shown in Table 3:

TABLE 3

| | $T_m$ | $\Delta T_m$ |
|---|---|---|
| ON-21 | 76.5 | |
| ON-22 | 53.0 | 23.5 |
| ON-21A | 68.0 | |
| ON-22A | 42.0 | 26.0 |
| ON-21B | 70.0 | |
| ON-22B | 45.0 | 25.0 |

The differences in $T_m$ between the scrambled and unscrambled form are roughly the same regardless of the pyrimidine or linkage substitution used.

Inhibition of Target Gene Expression.

Additional oligomers designed to target T antigen (TAg) in a modification of the in vivo antisense assay described by Graessmann, M. et al. *Nucleic Acids Res* (1991) 19:53–59 were also modified to contain U* and/or C* as well as modified internucleoside linkages. The assay uses an expres- ON 17: phosphorothioate 5' C*U*U*C*AU*U*U*U*U* 3' (SEQ ID NO:20)

ON 18: phosphorothioate 5' C*U*U*C* AU*U*AU*U*U*C*U*U*C* 3' (SEQ ID NO:21)

ON 19: phosphorothioate 5' C*U*U*U*C* U*U*C*U*U*AC*U*U*C* 3' (SEQ ID NO:22)

ON 18 and 19 were mismatch controls and have the same base composition found in ON 15 with sequence mismatches as shown in bold. The $T_m$ of the oligomers with the complementary RNA were determined as described above. The nuclease stability of the oligomer in the cells and the ability of the oligomer to inhibit T antigen synthesis was also determined. The ability of ON 11 to ON 17 to confer RNase H sensitivity on the bound RNA was also determined and each oligomer was found to confer RNase H sensitivity. Details of the antisense assay protocol are described in Example 7. The results are shown in Table 4.

TABLE 4

| Oligomer | RNA $T_m$* | S.N.** | TAg $IC_{50}$*** |
|---|---|---|---|
| ON-11 | 54.0° C. | − | − |
| ON-12 | 40.0° | + | n.s. |
| ON-13 | 82.5° | − | 2.5 |
| ON-14 | 76.5° | + | 0.05 |
| ON-15 | 71.0° | + | 0.10 |
| ON-16 | 63.5° | + | 0.25 |
| ON-17 | 53.5° | + | 1.0 |
| ON-18 | 59.5° | + | 0.50 |
| ON-19 | 43.0° | + | − |

*$T_m$, thermal stability of duplex determined under the same conditions as previously described at pH 6.6 in 1 mM $MgCl_2$.
**S.N., stability to nuclease digestion in live cells at 37° C.; (−) nuclease sensitive, (+) nuclease resistant.

TABLE 4-continued

| Oligomer | RNA $T_m$* | S.N.** | TAg $IC_{50}$*** |
|---|---|---|---|

***$IC_{50}$, oligomer concentration ($\mu$M) showing 50% inhibition of TAg expression; (−), no inhibition of TAg expression detected; (n.s.), nonspecific inhibition at 25 $\mu$M.

As seen, substituting the phosphorothioate linkage for phosphodiester decreases the affinity of the oligomer for target RNA but enhances the nuclease stability of the oligomers in the cell. Replacement of the thymine and cytosine bases by the 5-substituted bases of the invention enhanced affinity of the oligomers. At an increased concentration of oligomer (diester, ON-13), the enhanced affinity of the oligomer led to detectable T antigen synthesis inhibition. The phosphorothioate analog containing the modified bases is sufficiently stable and has sufficient affinity for the target RNA to effect inhibition of the synthesis of T antigen. The increasing $IC_{50}$ value coupled with the decreasing $T_m$ of ON 18 and ON 19 relative to ON-15 indicated that these oligomers were binding to target sequences less effectively as the number of mismatches increased. These results demonstrate sequence-specific inhibition of target gene expression by invention antisense oligomers.

In addition to inhibition of TAg synthesis, a phosphorothioate oligomer, ON 20, 5' U*U*GC'C'GU*U*U*U*C'AU*C'AU'AU*U*U*AAU* 3' (SEQ ID NO:23), that is complementary to the β-galactosidase RNA, was able to inhibit β-galactosidase in a sequence specific manner with an $IC_{50}$ of 0.25 $\mu$M. ON 20A, ON 20 with T and C', did not inhibit β-galactosidase expression in a sequence specific manner.

EXAMPLE 7

Assay Method and Inhibition of Target Gene Expression

Assay Method. Antisense oligomers were evaluated for biological efficacy in vivo using a microinjection procedure. The protocol differs from previously described procedures by utilizing an additional coinjected gene which serves as an internal control for transfected gene expression (Graessman, M., et al., Nucleic Acids Res (1991) 19:53–59). Microinjections were performed using 5–10 copies per cell of pSV40 plasmid expressing the TAg gene along with (varying amounts of) antisense oligomers targeted to different regions to the TAg RNA. Coinjection markers such as 40 copies of plasmid per cell containing the β-galactosidase gene under the control of the RSV promoter or the chloramphenicol acetyl transferase gene under the control of the SV40 promoter were used. Marker genes are those which generate proteins that can readily be measured so that specificity of gene expression inhibition can be shown. The antisense oligomer does not affect the ability of the cells to continue to produce protein products of the marker gene. Suitable marker genes generate chloramphenicol acetyltransferase (CAT), β-galactosidase, luciferase or cell surface antigens, enzymes or markers for which assay methods are known. In control experiments without antisense oligomer, 100% of microinjected cells expressed the β-galactosidase protein at 4.5 h after injection while approximately 60% of microinjected cells expressed the TAg protein, as detected by dual label immunofluorescent labeling techniques. Target sequences in the TAg RNA included a coding sequence approximately 150 bases from the translation initiation AUG codon, sequences in the 5'-untranslated region and sequences at the AUG codon. Antisense oligomers from 9 to 20 bases in length were examined using concentrations of oligomers of between 5 nM and 25 $\mu$M and the compounds were assayed at times ranging from 4.5 to 72 hours postinjection. CV1 or Rat2 cells were microinjected using conditions essentially as described (Graessman, M., et al., ibid.).

Target Sequence Binding and Target Gene Inhibition. An oligomer (5' ATTTTC'TTC'ATTTTTC'TTC' 3' (SEQ ID NO:14)) was systematically varied, using the phosphodiester antisense oligomer, ON-11, as a control. The phosphorothioate analog, ON-12, of the same oligomer was also prepared, but had no altered bases. The corresponding oligomer having the 5-substituted bases of the invention universally substituted was prepared both in the phosphodiester, ON-13, and phosphorothioate form, ON-14; finally, the 2'-O-allyl-substituted form was tested as well.

As shown in Table 4, substituting the phosphorothioate linkage for phosphodiester decreases the affinity for target RNA but enhanced the nuclease stability. Analysis of the time course of inhibition of T antigen expression showed that ON-13 (phosphodiester linked oligomer containing U* and C*) had activity that was detectable until 6 hours after microinjection into cells at a concentration of 25 $\mu$M. By contrast, ON-14 (phosphorothioate linked oligomer containing U* and C* with the same sequence as ON-13) was active for 48 hours after microinjection of 0.5 $\mu$M oligomer into cells.

Both the 9-mer (5' C*U*U*C*AU*U*U*U* 3' (SEQ ID NO:24)) and 11-mer (ON-17) phosphorothioates were able to inhibit T antigen synthesis when they contain the 5-substituted bases of the invention. However, the 9-mer had relatively weak sequence-specific inhibitory activity.

Also tested in the foregoing assay were an oligomer (5'UT) designed to bind to the 5' untranslated region of the T antigen near the CAP site of the mRNA and an oligomer with a sequence designed to bind to the region of the start codon. These oligomers have the sequences shown:

5'UT oligomer: 5'-GCC TCC TCA CTA CTT CTG GA-3' (SEQ ID NO:26)

AUG oligomer: 5'-CAT CTT TGC AAA GCT TTT TG-3' (SEQ ID NO:27)

The phosphorothioate form of the 5'UT and AUG oligomers composed of thymine and 5-methylcytosine bases was unable to effect detectable inhibition at 20 $\mu$M. However, the phosphorothioate analogs wherein 5-propynyluracil was substituted systematically for thymine residues showed 100% inhibition at 1 $\mu$M.

Further experiments with this assay system using a T antigen target sequence in the 5' untranslated 5 region demonstrated that substitution of the modified oligomers of the invention containing phosphodiester linkages but containing 2'-O-allyl substitutions in the oligomers containing fully substituted nucleomonomers wherein C* replaces C and U* replaces T are capable of inhibiting T antigen synthesis. Table 5 shows the results obtained using the 5'UT oligomer. Oligomers 1–4 were 20-mers having the sequence shown above. Oligomer 5 had the underlined sequence shown above and 5-propynyluridine substituted for thymidine and 5-propynylcytidine substituted for cytidine.

TABLE 5

| Oligomer* | Tm | IC50 ($\mu$M) |
|---|---|---|
| 1. 2'-O—Me (U, C) | — | n.i.** |
| 2. Thioate (T, C') | 70.5 | 2.5 |
| 3. Thioate (U*, C') | 81.0 | 0.5 |

TABLE 5-continued

| Oligomer* | Tm | IC50 (μM) |
|---|---|---|
| 4. Thioate (U*, C') | >90.0 | 0.25 |
| 5. 2'-O-allyl (U*, C*) | >90.0 | 5.0 |

*Thioate or phosphorothioate linkages
**No detectable inhibition at 5 μM

As shown in Table 5 various combinations of inclusion of U* and C* along with either a phosphorothioate backbone or a 2'-O-allyl substitution provided inhibition. Although oligomer 5 is not a substrate for RNase H, inhibition of TAg expression was observed. Inhibition mediated by oligomer 5 is believed to result from the high affinity and nuclease stability that the 2'-O-allyl modification confers. Incorporation of U* and/or C* into oligomers containing full or partial 2'-O-allyl modification will provide oligomers that can be used to inhibit target gene expression.

In addition to sequences in the 5'UT, AUG codon region and exon described above, TAg sequences at TAg intron/exon junction, exon/exon junction and in an intron were targeted using 15-mer phosphorothioate oligomers that were fully substituted with U* and/or C* according to the target sequences. The oligomers contained from about 50% to about 70% of U* and/or C* bases in the oligomer. All of the oligomers effectively inhibited TAg synthesis. These results indicated that the high affinity oligomers were capable of inhibiting gene expression at locations throughout the RNA and were thus effective in spite of any secondary structure that can have been present in the TAg RNA.

EXAMPLE 8

Delivery of Olipomers into Cells

ON-15 was tested for inhibition of T antigen (TAg) expression using the method described in Example 7. ON-15 was incubated for 24 hours with CV1 cells at an extracellular concentration of 50 μM in tissue culture medium, followed by microinjection of TAg and β-galactosidase expression plasmids. 4.5 hours after injection, cells were fixed and stained for TAg expression. By comparison with microinjected ON-15, which efficiently inhibits TAg expression, ON-15 incubated in extracellular medium was much less efficient with no detectable inhibition of TAg synthesis. The experiment was repeated using ON-15 derivatized at the 5' end with fluorescein-aminohexanol (Fl-ON-15) at an extracellular concentration of 50 μM which was incubated with cells for 24 hours. Control cells were microinjected with Fl-ON-15 at an intracellular concentration of 0.5 μM along with TAg and β-galactosidase expression plasmids. Microinjected Fl-ON-15 was localized in the nucleus while Fl-ON-15 added to the extracellular medium was localized in cytoplasmic compartments that resembled endosomes and lysosomes. The same pattern of results were obtained in CV1, Rat2, HeLa, SKOV-3, BUD-8, BC3H1 and ccd45sk cell lines. Oligomers of the invention are active in different mammalian species and are thus suitable for modulating gene expression regardless of the species.

Fl-ON-15 and ON-15 were delivered to cellular cytoplasm using a commercially available cationic lipid preparation, Lipofectin™ (BRL-Gibco, cat. no. 8292SA). A Lipofectin™ concentration of 10 μM in Optimem (BRL-Gibco) was used according to manufacturer's instructions. DOTMA is the lipid present in Lipofectin™. Cells were incubated in Optimem containing either the Fl-ON-15-lipid or ON-15-lipid preparation for 4 hours, followed by incubation of the cells for 16 hours in standard medium (DMEM with 10% FBS for CV1 cells). Immunofluorescence analysis of treated cells showed that about 90% of the cells contained Fl-ON-15 localized in the nucleus. Delivery of ON-15 to cells was assayed by microinjection of TAg and β-galactosidase expression plasmids into cells after incubation with the lipid-oligomer complex. ON-15 inhibited TAg expression with an $IC_{50}$ of less than 5 nM using Lipofectin™ at a 10 μM concentration. Preparations of oligomer complexed with cationic lipid (such as Lipofectin™) were thus capable of delivering oligomers containing a label such as fluorescein and/or 5-modified pyrimidines such as U* or C* to the cellular cytoplasm, indicating that modifications incorporated into oligomers, such as base analogs or a label, do not interfere with formation cationic lipid-oligomer complexes.

In an alternative protocol, Fl-ON-15 was also delivered into cells by a transfection protocol using DMSO. CV1 cells were incubated in DMEM-10% FBS medium containing 1% DMSO and 1 μM Fl-ON-15 for 4 hours at 37° C. Fluorescence microscopy demonstrated that the oligomer was localized in the nucleus of about 20% of the treated cells.

Fl-ON-15 was synthesized by coupling a commercially available aminohexane amidite (Glen Research) to the 5'-OH of ON-15 using standard coupling conditions. The free amine was then linked to fluorescein-NHS ester (Molecular Probes) to generate Fl-ON-15. Synthesis of fluorescein-linked oligomer can also be accomplished using fluorescein amidite or fluorescein-CPG according to manufacturer's instructions (Glen Research).

EXAMPLE 9

Synthesis of 2'-O-Allyl Monomers for oligomer Synthesis

Preparation of 5-propynyl-2'-O-allyluridine nucleomonomer. 343 mg (0.50 mmole) of 14 (FIG. 4) was dissolved into anhydrous $CH_3CN$ (5 mL) and to this was added 2-pyridinealdoxime (67 mg, 0.55 mmole) and 1,1,3,3-tetramethylguanidine (75 μL, 0.6 mmole) at room temperature. After 18 hr the reaction mixture was diluted with EtOAc and washed with aq. citric acid (0.1M). The aqueous layer was extracted with EtOAc, the combined organic layers washed with saturated aq. $NaHCO_3$ (3 times), dried over $Na_2SO_4$ and evaporated. The residue was dissolved into EtOAc (5 mL) and to this was added 1M TBAF/THF (1.5 mL, 1.5 mmole), the solution stirred for 1 hr and diluted with EtOAc. The solution was washed with saturated aq. $NaHCO_3$ (2 times), the combined aqueous layer extracted with EtOAc (3 times), the combined organic phase dried over $Na_2SO_4$ and evaporated. The residue was evaporated from anhydrous pyridine (10 mL), dissolved into anhydrous pyridine (5 mL), and to this was added dimethoxytrityl chloride (200 mg, 0.6 mmole) and the solution stirred for 18 hr. The reaction mixture was evaporated to approximately 2 mL, diluted with $CH_2Cl_2$, washed with saturated aq. $NaHCO_3$, dried over $Na_2SO_4$ and evaporated. Purification by silica gel chromatography (EtOAc/Hexane, 1/1) yielded 197 mg (0.32 mmole, 64%) of 6 shown in FIG. 4.

Preparation of 5-propynyl-2'-O-allylcytidine nucleomonomer. 343 mg (0.50 mmole) of 14 was dissolved into anhydrous $CH_3CN$ (10 mL), and the solution transferred to a Parr Bomb, cooled to 0° C., and saturated with $NH_3$. This was placed in an 80° C. bath for 24 hr (75 psi), cooled to room temperature and evaporated to dryness. The residue was evaporated from anhydrous DMF (10 mL), dissolved into anhydrous DMF (5 mL), and to this was added diisobutylformamide dimethylacetal (0.2 mL, 0.84 mmole) at room temperature. After 18 hr H$_2$O (25 µL) was added, the solution evaporated, dissolved into EtOAc (5 mL) and to this was added 1M TBAF/THF (1.5 mL, 1.5 mmole). After 1 hr the reaction mixture was diluted with EtOAc, washed with saturated aq. NaHCO$_3$, dried over Na$_2$SO$_4$ and evaporated. The residue was evaporated from anhydrous pyridine (10 mL), dissolved into anhydrous pyridine (5 mL), and to this was added dimethoxytrityl chloride (200 mg, 0.6 mmole) and the solution stirred for 5 hr. The reaction mixture was evaporated to approximately 2 mL, diluted with CH$_2$Cl$_2$, washed with saturated aq. NaHCO$_3$, dried over Na$_2$SO$_4$ and evaporated. Purification by silica gel chromatography (EtOAC/Hexane, from 2/3 to 3/2) yielded 242 mg (0.32 mmole, 64%) of 8 shown in FIG. 4.

EXAMPLE 10

Formacetal Dimer Synthesis

Figure 11:
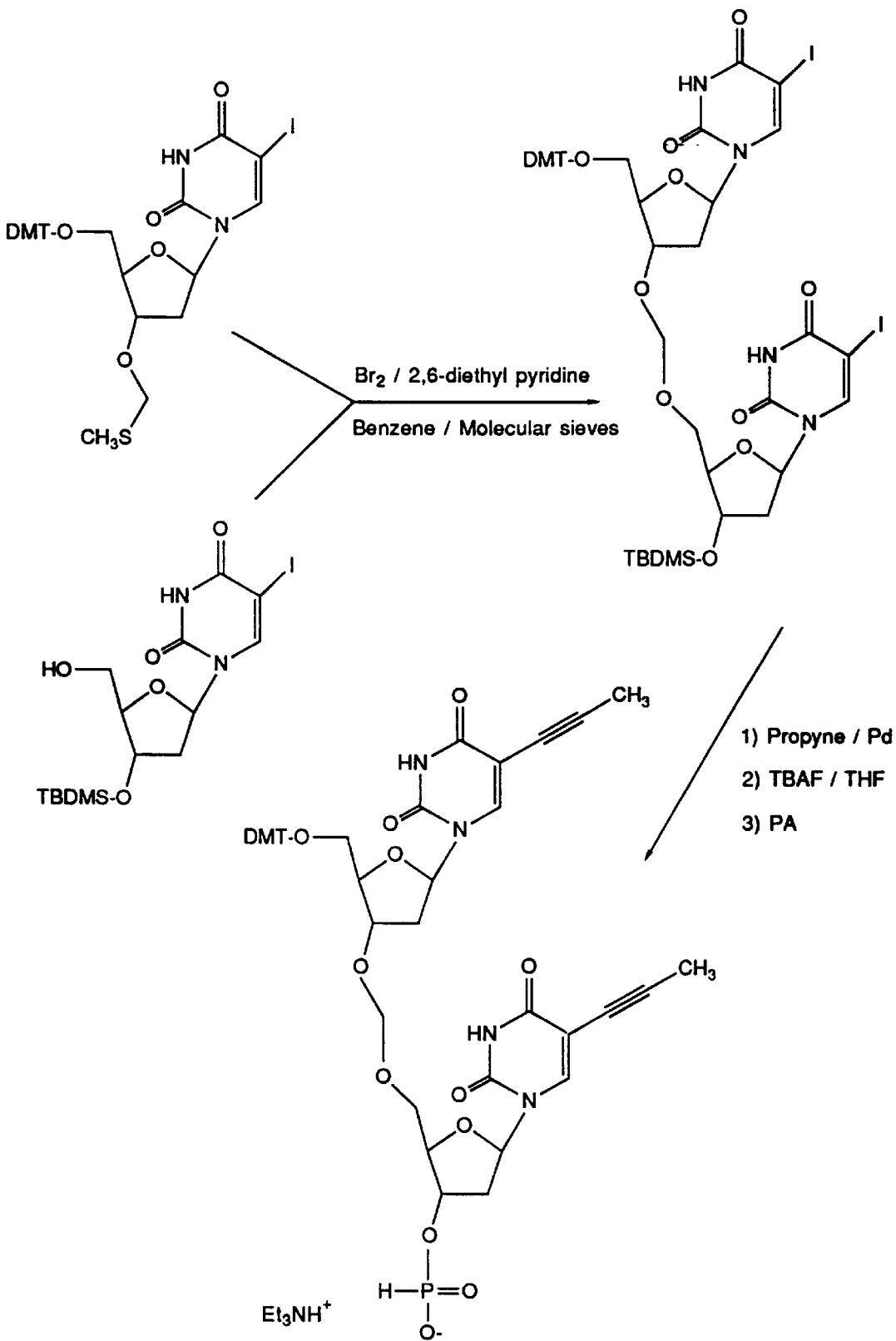
FIG. 11. Synthesis of dimer linked by a formacetal linkage (method #2).

FIG. 11 shows a synthesis scheme that was used to obtain a formacetal linked 5-propynyl-2'-deoxyuracil dimer. The synthesis protocol introduced the propynyl substituent at the level of a dimer by conversion of the 5-iodouracil precursor as shown. A similar protocol can be used to convert trimers, tetramers, pentamers or longer 5-iodo precursors to the 5-propynyl product in a similar fashion. This synthetic method gave unexpectedly high yields of the 5-propynyl product.

EXAMPLE 11

3'-Thioformacetal Dimer Synthesis

Preparation of (26): (25) was suspended into CH$_2$Cl$_2$ and paraformaldehyde (1.6 eq) was added, the suspension cooled to 0° C. and HCl (anhydrous) passed through the solution for about 10 minutes. The suspension was sealed and stored at 0–5° C. for 4 hours. The resulting solution was dried, filtered, and evaporated to yield (26).

Preparation of 10: 3'-Deoxy-3'-thioacetyl-5'-dimethoxytrityl-5-propynyl-2'-deoxyuridine was dissolved in methanolic ammonia in a flask that had been flushed ith O$_2$ and the solution was sealed and stirred for 1 hour. The solvent was removed and the residue dissolved in EtOAc and washed with NaHCO$_3$ and brine. The organic phase was dried, evaporated and purified by silica gel chromatography (MeOH/CH$_2$Cl$_2$). The resulting disulfide was dissolved into dioxane/H$_2$O followed by addition of tributylphosphine (1.0 eq) and the solution stirred for 30 minutes. The solvent was removed and crude compound 10 was used directly to prepare (27).

Preparation of (27): Compound 10 (1.1 eq) was dissolved in DMF and DIPEA (diisopropylethylamine, 2.5 eq) was added and the solution was cooled to 0° C. under Ar. A solution of compound (26)(1 eq, in DMF) was added, the solution stirred for 10 hours, diluted, extracted against H$_2$O, dried, evaporated and purified by silica gel chromatography (MeOH/CH$_2$Cl$_2$).

Preparation of 11: (27) was dissolved in methanolic ammonia and stirred in a sealed flask at room temperature for 3 hours. The solvent was removed and purified (Silica Gel, MeOH/CH$_2$Cl$_2$ (0–4% MeOH)) and the propyne moiety introduced has described in Example 1.

Preparation of 11A: 11 was phosphitylated using standard procedures.

EXAMPLE 12

5-(2-Pyridinyl)-21'-Deoxyuridine and 5-(2-Pyridinyl-2'-Deoxycytidine Synthesis

2-Trimethylstannylpyridine. A solution of 15.7 mL of 1.6 M n-butyllithium (25.1 mmol) in anhydrous ether (25 mL) was stirred under Ar at −78° C. and to this was added a solution of 2-bromopyridine (3.97 g, 25.1 mmol) in anhydrous ether (12.5 mL). The resulting orange solution was stirred for 2 h, and trimethyltin chloride in THF (26.0 mmol, 26 and, 1.0M) added over 30 min. The reaction was stirred for 1 h at −78° C. then warmed to room temperature over 1 h, filtered and the filtrate evaporated. Distillation afforded 3.1 g (51%) of the title compound as a colorless liquid which solidified in the receiver flask. B.p. 65° C./2 mm Hg; Literature B.p. 75° C./4 mm Hg.

5-(2-pyridinyl)-2'-deoxyuridine. In a 25 mL pear shaped flask was placed 5-iodo-2'-deoxyuridine (0.354 g, 1.0 mmol), 2-trimethylstannylpyridine (0.84 g, 3.5 mmol), Bis (triphenylphosphine)-palladium (II) chloride (0.070 g, 0.1 mmol), and anhydrous 1,4-dioxane (15 mL). The reaction was heated at 60° C. for 15 hrs then at 90° C. for 1 h. The solvent was evaporated and the residue purified by silica gel chromatography (10% CH$_3$OH in CH$_2$Cl$_2$ (1% NH$_3$)) to yield 0.253 g (83%) of the title compound as a white solid m.p. 201°–203° C.

5-(2-pyridinyl)-2'-deoxycytidine. In a 25 mL pear shaped flask was placed 5-iodo-2'-deoxycytidine (0.425 g, 1.2 mmol), 2-trimethylstannylpyridine (1.4 g, 5.8 mmol), Bis (triphenylphosphine)-palladium (II) chloride (0.084 g, 0.12 mmol), and anhydrous 1,4-dioxane (15 mL). The reaction was heated at 60° C. for 15 hrs then at 90° C. for 1 h. The solvent was evaporated and the residue purified by silica gel chromatography (10% CH$_3$OH in CH$_2$Cl$_2$ (1% NH$_3$)) to yield 0.173 g (47%) of the title compound as a white solid m.p. 197°–198° C.

EXAMPLE 13

Synthesis of 5-(Thienyl)-5'Dimethoxytrityl-2'Deoxyuridine

2-Trimethylstannylthionhene. To a solution of thiophene (2.1 g, 25.0 mmol) in anhydrous THF (50 mL) was added dropwise over 30 minutes at −38° C. t-butyllithium in pentane (1.6M, 16.0 mL, 25.6 mmol). The solution was stirred for 1 h at −38° C. and then cooled to −78° C. Trimethyltin chloride in THF (1M, 25.3 mL, 25.3 mmol) was added dropwise over 30 min. The reaction was then stirred for 2 h at −78° C. and then for 15 h at r.t. The solvent was evaporated and the resulting yellow solid was taken up in ether, washed with water and dried Na$_2$SO$_4$ and then evaporated to give a light brown liquid which solidified on standing.

5-(2-thienyl)-5'-dimethoxytrityl-2'-deoxyuridine. In a 50 mL flask was placed 5-iodo-dimethoxytrityl-3'-O-toluolyl-2'-deoxyuridine (2.15g, 2.77 mmol), 2-trimethylstannylthiophene (1.85 g, 7.5 mmol), Bis (triphenylphosphine)-palladium (II) chloride (0.196 g, 0.28 mmol) and anhydrous THF (30.0 mL). The was heated at 73° C. for 18 h, then cooled to room temperature. The resulting black precipitate was filtered and washed with THF. The solvent was evaporated and the green residue was dissolved in ethyl acetate (100 mL), washed with water (50 mL) and dried (Na$_2$SO$_4$). The solvent was evaporated and the residue was taken up in dioxane/conc. NH$_4$OH (1/1, 80 mL), stirred for 18 h at r.t. and evaporated. Silica gel purification yielded 0.430 g (25%) of 5-(2-thienyl)-5'-dimethoxytrityl-2'-deoxyuridine.

EXAMPLE 14

Synthesis of 5-((1-Ethynyl)-2-Pyrimidinyl)-2'-Deoxyuridine

2-Iodopyrimidine. Liquid HI (28.0 mL, 212 mmol) was tirred vigorously at 0° C. and solid 2-chloropyrimidine (7.0 g, 61 mmol) was added slowly so that the temperature did not rise above 8° C. The reaction was stirred at 5° C. for 1 h., solid potassium carbonate (14.7 g, 106 mmol) was arefully added over 0.5 h. (temperature less than 10° C.), and the reaction was decolorized by addition of a small amount of solid sodium bisulfite. The solution was extracted with eiher (5×50 mL), dried ($Na_2SO_4$), evaporated and the residue was recrystalized from hexane to afford 7.11 g (56%) of the title compound, m.p. 29°–30° C.

2-((Trimethylsilyl)ethynyl)pyrimidine. In a 50 mL flask was placed 2-iodopyrimidine (20. g, 9.7 mmol), copper (I) iodide (9.5 mg, 0.05 mmol), triethylamine (0.7 mL, 5.0 mmol), Bis(triphenylphosphine)-palladium (II) chloride (0.07 g, 0.1 mmol) and anhydrous dioxane (10 mL). The reaction was heated at 60° C. for 18 hours then at 95° C. for 8 h. The solvent was evaporated and the residue was dissolved in $CH_2Cl_2$ (200 mL), washed with $H_2O$ (40 mL), dried ($Na_2SO_4$) and evaporated. The product was purified by silica gel chromatography ($CH_2Cl_2$) to yield 1.06 g (60%) of the title compound.

2-ethynylpyrimidine. To a solution of 2-((Trimethylsilyl) ethynyl)pyrimidine (1.06 g, 6.0 mmol) in anhydrous methanol (9 mL) was added solid potassium carbonate (0.083 g, 0.6 mmol) and the reaction stirred for 2.5 h. The solid was removed by filtration, washed with methanol (10 mL) and the supernatant evaporated. The residue was dissolved in $CH_2Cl_2$ (30 mL), washed with saturated $NaHCO_3$, dried ($Na_2SO_4$) and evaporated. Silica gel chromatography (1–2% $CH_3OH$ in $CH_2Cl_2$) yielded 0.400 g (64%) of the title compound. This was coupled to 5-Iodo-2'-deoxyuridine and converted to the protected H-phosphonate as in Example 1.

EXAMPLE 15

Binding of Oligomers Containing U* and 3'-Thioformacetal or Formacetal Linkages

The following oligomers were synthesized. Unless otherwise indicated, all linkages were phosphodiester. The symbol, ●, indicates a 3'-thioformacetal linkage (3',5'), and the symbol, O, indicates a formacetal linkage (3',5').

ON-1 5' TC'TC'TC'TC'TC'TTTTT 3' (SEQ ID NO:1)

ON-23 5' TC'TC'TC'TC'TC'U*U*U*U*T 3' (SEQ ID NO:28)

ON-24 5' TC'TC'TC'TC'TC'T●TT●TT 3' (SEQ ID NO:29)

ON-25 5' TC'TC'TC'TC'TC'U*●U*U*●U*T 3' (SEQ ID NO:30)

ON-26 5' TC'TC'TC'TC'TC'U*OU*U*OU*T 3' (SEQ ID NO:31)

The oligomers were tested with respect to thermal denaturation ($T_m$) or stability after hybridization with DNA or RNA targets to form triplex or duplex structures respectively. The DNA target used was an oligomer containing a self-complementary region and having a 4 nucleotide loop at the end of the hairpin as shown. The targets were as follows:

DNA Duplex Target: 5' AGAGAGAGAGAAAAAGGA$^T$ T (SEQ ID NO:10)

3' TCTCTCTCTCTTTTTCCT $_T$ T (SEQ ID NO:11)

RNA Target: 5' AAAAAGAGAGAGAGA 3' (SEQ ID NO:12)

The assays for binding were conducted in 140 mM KCL/5 mM $Na_2HPO_4$/1 mM $MgCL_2$ at pH=7.2 for single stranded RNA or DNA (duplex hybridization) and at pH=6.6 for duplex DNA (triplex hybridization conditions). The final concentration of all oligomers was ~2 μM. $T_m$ data obtained with the oligomers is shown in Table 6.

TABLE 6

| ON | Duplex $T_m$ RNA | DNA | Triplex $T_m$ |
|---|---|---|---|
| ON-1 | 62.5 | 55.5 | 38.9 |
| ON-23 | 69.0 | 59.5 | 45.0 |
| ON-24 | 62.0 | 53.0 | 41.5 |
| ON-25 | 71.5 | 61.5 | 47.6 |
| ON-26 | 69.0 | 59.5 | 45.5 |

EXAMPLE 16

Binding of Oligomers Containing 5-(2-Pyridinyl)-2'-Deoxyuridine ($U^P$) or 5-(2-Pyridinyl)-2'-Deoxycytidine ($C^P$) and 5-(2-Thienyl)-2'-Deoxyuridine ($U^T$)

The following oligomers were synthesized. All linkages were phosphodiester.

ON-1 5' TC'TC'TC'TC'TC'TTTTT 3' (SEQ ID NO:1)

ON-28 5' TC'TC'TC'TC'TC'$U^PU^PU^PU^PU^P$ 3' (SEQ ID NO:32)

ON-29 5' TC'TC'TC'$U^PC'U^PC'U^PTU^PTU^P$ 3' (SEQ ID NO:33)

ON-30 5' T$C^P$T$C^P$T$C^P$T$C^P$T$C^P$TTTTT 3' (SEQ ID NO:34)

ON-43 5' TC'TC'TC'TC'TC'$U^TU^TU^TU^TU^T$ 3' (SEQ ID NO:35)

ON-44 5' TC'TC'TC'$U^TC'U^TC'U^TTU^TTU^T$ 3' (SEQ ID NO:36)

The oligomers were tested with respect to thermal denaturation ($T_m$) or stability after hybridization with ssDNA or ssRNA targets to form a duplex and with dsDNA to form a triplex. The DNA target used was an oligomer containing a self-complementary region and having a 4 nucleotide loop at the end of the hairpin as shown. The targets were as follows:

DNA Duplex Target: 5' AGAGAGAGAGAAAAAGGA$^T$ T (SEQ ID NO:10)

3' TCTCTCTCTCTTTTTCCT $_T$ T (SEQ ID NO:11)

DNA/RNA Target Sequence: 5' AAAAA-GAGAGAGAGA 3' (SEQ ID NO:12)

The assays for triple-helix binding were conducted in 140 mM KCL/5 mM $Na_2HPO_4$/1 mM $MgCL_2$ at pH=7.2 for single stranded RNA or DNA (duplex hybridization) and at pH=6.6 for duplex DNA (triplex hybridization conditions). The final concentration of all oligomers was ~2 μM. $T_m$ data obtained with the oligomers is shown in Table 7.

TABLE 7

| ON | Duplex $T_m$ RNA | DNA | Triplex $T_m$ |
|---|---|---|---|
| ON-1 | 62.5 | 55.0 | 39.6 |
| ON-28 | 64.0 | 54.0 | 41.8 |
| ON-29 | 62.5 | 52.0 | 31.7 |
| ON-30 | 61.5 | 46.5 | — |
| ON-43 | 64.5 | 55.0 | 31.6 |
| ON-44 | 63.5 | 52.5 | 19.9 |

EXAMPLE 17

Binding of Oligomers Containing 5-(1-Propynyl)-2'-Deoxyuridine (U*) and Carbocyclic 5-Methyl-2'Deoxycytidine(C#) or 8-Oxo-$N^6$-Methyl-2'-Deoxyadenosine (M)

The following oligomers were synthesized. All linkages were phosphodiester.

ON-1 5' TC'TC'TC'TC'TC'TTTTT 3' (SEQ ID NO:1)

ON-32 5' U*C#U*C#U*C#U*C#U*C#U*U*U*U*U* 3' (SEQ ID NO:37)

ON-33 5' TTTMTTTMMTMMTTTTT 3' (SEQ ID NO:38)

N-34 5' U*U*U*MU*U*MMU*MMU*U*U*U*U* 3' (SEQ ID NO:4)

The oligomers were tested with respect to target sequence binding by footprint analysis using DNase digestion after binding with duplex DNA to form triplex structures. Hybridization was conducted at 37° C. for about 1 hour in 140 mM KCL, 10 mM NaCl, 1 mM MgCl, 1 mM spermine hydrochloride, MOPS pH 7.2 using target DNA at approximately 1 nM. The target sequence was as follows:

DNA Duplex Target: 5' AGAGAGAGAGAAAAA 3' (SEQ ID NO:4)

3' TCTCTCTCTCTTTTT 5' (SEQ ID NO:40).

The sequence was contained on a gel purified 370-bp restriction fragment derived from a cloning vector. The concentration of ON-1 and ON-32 was varied from 0.01 to 10.0 μM. The nuclease protection results obtained with ON-1 and ON-32 indicated that ON-32 had a binding affinity for duplex DNA that was about 1000-fold greater than the affinity of ON-1 for the same target.

The ON-33 and ON-34 target sequence was as follows:

DNA Duplex Target: 5' AAAGAAAGGAGGAAAAA 3' (SEQ ID NO:41)

3' TTTCTTTCCTCCTTTTT 5' (SEQ ID NO:42).

The sequence was contained in a plasmid that was linearized by restriction enzyme digestion. The sequence is found in the promoter region of the IL-1 gene. The assays for triple-helix binding were conducted in 140 mM KCL/10 mM NaCl/1 mM MgCL$_2$/1 mM spermine hydrochloride/20 mM MOPS pH 7.2. The final concentration of the target was ~2 nM while the concentration of ON-33 and ON-34 was varied from 0.1 to 10.0 μM. The nuclease protection results obtained with ON-33, which gave full DNase protection at 0.1 μM, and ON-34, which gave full DNase protection at a concentration well below 0.1 μM, indicated that ON-34 had a binding affinity for duplex DNA that was greater than or equal to 10-fold greater than the affinity of ON-33 for the same target.

The results obtained with these oligomers indicate that the invention bases are compatible with other triplex binding competent base analogs and can thus be used to design high affinity oligomers with triplex-competent bases and base analogs as desired.

EXAMPLE 18

Duplex Formation Using Oligomers Containing 5-(1-Propynyl)-2'-O-Allyluridine (U$^X$) or 5-(1-Propynyl)-2'-O-Allylcytidine (C$^X$)

The following oligomers were synthesized. All linkages were phosphodiester. Nucleomonomers were prepared as described in Example 9. 5- Methyl-2'-O-allyluridine, T', and 5-methyl-2'-O-allylcytidine, C'', were used in addition to U$^X$ and C$^X$.

ON-1 5' TC'TC'TC'TC'TC'TTTTT 3' (SEQ ID NO:1)

ON-35 5' TC'TC'TC'TC'TC'T'T'T'T'T' 3' (SEQ ID NO:43)

ON-36 5' TC'TC'TC'TC'TC'U*U*U*U*U* 3' (SEQ ID NO:44)

ON-37 5' TC'TC'TC'TC'TC'U$^X$U$^X$U$^X$U$^X$U$^X$ 3' (SEQ ID NO:45)

ON-38 5' TC"TC"TC"TC"TC"TTTTT 3' (SEQ ID NO:46)

ON-39 5' TC*TC*TC*TC*TC*TTTTT 3' (SEQ ID NO:47)

ON-40 5' TC$^X$TC$^X$TC$^X$TC$^X$TC$^X$TTTTT 3' (SEQ ID NO:48)

The oligomers were tested with respect to thermal denaturation ($T_m$) or stability after hybridization with an RNA target to form duplex structures. The target was as follows:

RNA Target: 5' AAAAAGAGAGAGAGA 3' (SEQ ID NO:49)

The assays for duplex-helix binding was conducted in 140 mM KCL/5 mM Na$_2$HPO$_4$/1 mM MgCL$_2$ at pH=6.6 for the RNA target. The final concentration of all oligomers was ~2 μM. $T_m$ data obtained with the oligomers is shown in Table 8.

TABLE 8

| ON | $T_m$ | $\Delta T_m$ (OC/substitution) |
|---|---|---|
| ON-1 | 63.0 | — |
| ON-35 | 64.5 | +0.3 |
| ON-36 | 70.5 | +1.5 |
| ON-37 | 71.5 | +1.7 |
| ON-38 | 66.5 | +0.7 |
| ON-39 | 70.0 | +1.4 |
| ON-40 | 73.0 | +2.0 |

The results obtained from these analyses demonstrated that the invention bases can be combined with modified sugars in binding competent oligomers. Enhanced binding due to the 2'-O-allyl sugar modification and to the invention bases give significantly increased binding affinity compared to either modification alone. The 2'-O-allyl modification renders oligomers incompetent as a substrate for RNase H. Thus, RNAs bound by oligomers containing 2' modifications and the invention bases can be advantageously used as probes for RNA sequences in cellular extracts containing nucleases.

EXAMPLE 19

Triplex Formation Using Oligomers Containing U* and a Switchback Linker (X*) containing U*

The following oligomers were synthesized. All linkages were phosphodiester.

ON-41

5' U*C'U*C'U*U*U*U*U*U*C'U*U*C'U*C'U*U*U*C'X*U*U*U*U*U*U*U* 3' (SEQ ID NO:50)

ON-42

5' U*C'U*C'U*U*U*U*U*C'U*U*C'U*C'U*U*U*C'X*U*U* 3' (SEQ ID NO:51)

The DNA target sequence used was:

DNA Duplex Target: 5' AGAGAAGGGAGAA-GAGAAAGAAATTTTTTTTT 3' (SEQ ID NO:52)

3, TCTCTTTTTTCTTCTCTTTCTTTAAAAAAAAA 5' (SEQ ID NO:53)

The target sequence was introduced into an intron of the TAg gene and was used in DNase protection analysis as a linearized restriction fragment at about 2 nM. The switchback linker synthon, X*, had the structure 9 shown in FIG. 5-1 and was incorporated into ON-41 and ON-42 by standard H-phosphonate chemistry. The switchback linker was associated with 2 null base pairs (bases in the target that were not hybridized with). Full DNase protection of the target sequence was obtained using either ON-41 or ON-42 at a concentration less than 100 nM.

These results demonstrate that the invention bases are compatible with switchback linkers, such as the o-xyloso linker described here.

EXAMPLE 20

Triple Helix Formation Using Oligomers Containing U* and Phosyhorothioate Linkage Triple helix formation was demonstrated using ON-5 and the phosphorothioate form of ON-5 as described in Example 16. The results show that ON-5 has a $T_m$ of 55.8° C. and the phosphorothioate derivative has a $T_m$ of 44.9° C. Thus, the oligomer containing the phosphorothioate linkage, in combination with the bases of the invention, is binding competent in triple helix formation.

The instant invention is shown and described herein in what is considered to be the most practical and preferred embodiments. It is recognized, however, that departures can be made therefrom which are within the scope of the invention, and that modifications will occur to those skilled in the art upon reading this disclosure.

---

We claim:

1. A method to evaluate a candidate antisense oligomer for its ability to inhibit gene expression, which method comprises:

microinjecting varying amounts of said candidate antisense oligomer into a host cell along with (a) a target vector for the expression of a gene containing a target sequence for said candidate antisense oligomer, and (b) a control vector for the expression of a control gene encoding a detectable protein, wherein said control gene does not contain said target sequence; and measuring expression of the target gene and the control gene;

wherein increasing inhibition of the target gene expression, but not of the control gene expression, as the amount of said candidate antisense oligomer increases, indicates the ability of said candidate antisense oligomer to inhibit gene expression.

2. The method of claim 1 wherein said target vector is injected at about 2–4 copies per cell and said control vector is injected at about 30–50 copies per cell.

3. The method of claim 1 wherein said detectable protein is chloramphenicol acetyl transferase, luciferase or β-galactosidase.

4. The method of claim 1 wherein said host cell is a mammalian cell.

5. The method of claim 2 wherein said detectable protein is chloramphenicol acetyltransferase, luciferase or β-galactosidase.

6. The method of claim 2 wherein the candidate antisense oligomer comprises a phosphorothioate or a phosphodiester linkage.

7. The method of claim 6 wherein the candidate antisense oligomer comprises a base selected from the group consisting of adenine, guanine, cytosine, 5-methylcytosine, thymine and uracil.

8. The method of claim 6 wherein the candidate antisense oligomer comprises a base of formula (1) or (2)

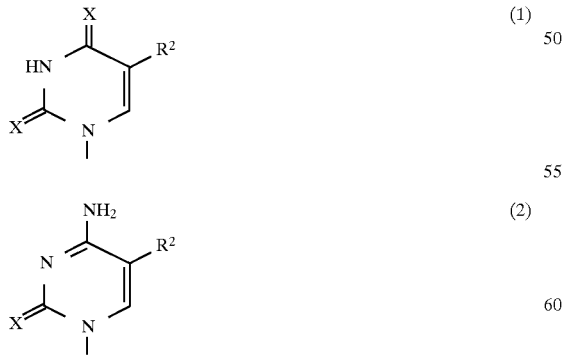

wherein each X is independently O or S; and $R^2$ is cyano, or $R^2$ is $C_{2-12}$ 1-alkynyl optionally substituted with halogen or an alkynyl group, $R^2$ is $C_{2-12}$ 1-alkenyl optionally substituted with halogen or an alkynyl group, or $R^2$ is a $C_{2-12}$ heteroaromatic group containing 5–6 ring atoms in which one to three of the ring atoms independently is nitrogen, oxygen or sulfur, whrein the heteroatromatic group is optionally substituted on a ring carbon atom by oxygen, halogen or $C_{1-4}$ alkyl or substituted on a ring nitrogen by $C_{1-4}$ alkyl, or $R^2$ is —C≡C—Z wherein Z is hydrogen or $C_{1-10}$ alkyl or $C_{1-10}$ haloalkyl with 1 to 6 halogen atoms, or Z is a (1-alkynyl)-heteroaromatic group optionally substituted on a ring carbon by oxygen or $C_{1-4}$ alkyl or optionally substituted on a ring nitrogen by $C_{1-4}$ alkyl.

9. The method of claim 8 wherein $R^2$ is 1-propynyl, 1-butynyl or 2-thiazolyl.

10. The method of claim 8 wherein the candidate antisense oligomer comprises a phosphorothioate linkage.

11. A method of inhibiting the expression of at least one selected protein in a cell, wherein the protein is translated from RNA, the method comprising the steps of:

introducing into the cell an oligomer comprising at least 8 nucleomonomers wherein at least one of the nucleomonomers comprises a base of formula (1) or (2)

wherein each X is independently O or S;

$R^2$ is cyano, or $R^2$ is $C_{2-12}$ 1-alkynyl optionally substituted with halogen or an alkynyl group, or $R^2$ is $C_{2-12}$ 1-alkenyl optionally substituted with halogen or an alkynyl group, or $R^2$ is a $C_{2-12}$ heteroaromatic group containing 5–6 ring atoms in which one to three of the ring atoms independently is nitrogen, oxygen or sulfur, wherein the heteroaromatic group is optionally substituted on a ring carbon atom by oxygen, halogen or $C_{1-4}$ alkyl or substituted on a ring nitrogen by $C_{1-4}$ alkyl, or $R^2$ is —C≡C—Z wherein Z is hydrogen or $C_{1-10}$ alkyl or $C_{1-10}$ haloalkyl with 1 to 6 halogen atoms, or Z is a (1-alkynyl)-heteroaromatic group optionally substituted on a ring carbon by oxygen or $C_{1-4}$ alkyl or optionally substituted on a ring nitrogen by $C_{1-4}$ alkyl;

Pr is $(H)_2$ or a protecting group, with the proviso that when at least one of the nucleomonomers of the oligomer comprises deoxyuridine 5-substituted by vinyl, 1-butenyl, 1-pentenyl, 1-hexenyl, 1-heptenyl, 1-octenyl, 1-propynyl, 1-butynyl, 1-hexynyl, 1-heptynyl, or 1-octynyl, then the remainder of the nucleomonomers comprising the oligomer are not solely comprised of phosphodiester linked 2'-deoxyadenosine, 2'-deoxyguanosine, 2'-deoxycytidine, thymidine or a combination thereof; and permitting the oligomer to form a duplex with the RNA whereby expression of the protein is inhibited.

12. The method of claim 11 wherein the oligomer is introduced into the cell by a method selected from the group consisting of calcium phosphate transfection, DMSO transfection, dextran transfection, cationic lipid transfection, anionic lipid transfection and liposome transfection.

13. The method of claim 11 wherein the RNA has a translocation junction, is a virally encoded RNA, or encodes a product selected from the group consisting of enzymes, hormones, serum proteins, adhesion molecules, receptor molecules, cytokines, oncogenes, growth factors, interleukins, mitogens, and MHC molecules.

14. The method of claim 13 wherein $R^2$ is selected from the group consisting of 1-propynyl, 1-butynyl and 2-thiazolyl.

15. A method of introducing an oligomer into cells, comprising:

mixing an oligomer comprising at least 8 nucleomdnomers wherein at least one of the nucleomonomers comprises a base of formula (1) or (2)

 (1)

 (2)

wherein each X is independently O or S;

$R^2$ is cyano, or $R^2$ is $C_{2-12}$ 1-alkynyl optionally substituted with halogen or an alkynyl group, or $R^2$ is $C_{2-12}$ 1-alkenyl optionally substituted with halogen or an alkynyl group, or $R^2$ is a $C_{2-12}$ heteroaromatic group containing 5–6 ring atoms in which one to three of the ring atoms independently is nitrogen, oxygen or sulfur, wherein the heteroaromatic group is optionally substituted on a ring carbon atom by oxygen, halogen or $C_{1-4}$ alkyl or substituted on a ring nitrogen by $C_{1-4}$ alkyl, or $R^2$ is —C≡C—Z wherein Z is hydrogen or $C_{1-10}$ alkyl or $C_{1-10}$ haloakyl with 1 to 6 halogen atoms, or Z is a (1-alkynyl)-heteroaromatic group olptionally substituted on a ring carbon by oxygen or $C_{1-4}$ alkyl or optionally substituted on a ring nitrogen by $C_{1-4}$ alkyl;

Pr is $(H)_2$ or a protecting group, with the proviso that when at least one of the nucleomonomers of the oligomer comprises deoxyuridine 5-substituted by vinyl, 1-butenyl, 1-pentenyl, 1-hexenyl, 1-heptenyl, 1-octenyl, 1-propynyl, 1-butynyl, 1-hexynyl, 1-heptynyl, or 1-octynyl, then the remainder of the nucleomonomers comprising the oligomer are not solely comprised of phosphodiester linked 2'-deoxyadenosine, 2'-deoxyguanosine, 2'-deoxycytidine, thymidine or a combination thereof, with a permeation enhancing agent to form a complex; and incubating the complex with the cells under conditions where the complex is introduced into the cells.

* * * * *

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 2
        ( D ) OTHER INFORMATION: /note= "This position is C'= 5-methyl-2'-deoxycytidine."

( i x ) FEATURE:
        ( A ) NAME/KEY: modified_base
        ( B ) LOCATION: 4
        ( D ) OTHER INFORMATION: /note= "This position is C'= 5-methyl-2'-deoxycytidine."

( i x ) FEATURE:
        ( A ) NAME/KEY: modified_base
        ( B ) LOCATION: 6
        ( D ) OTHER INFORMATION: /note= "This position is C'= 5-methyl-2'-deoxycytidine."

( i x ) FEATURE:
        ( A ) NAME/KEY: modified_base
        ( B ) LOCATION: 8
        ( D ) OTHER INFORMATION: /note= "This position is C'= 5-methyl-2'-deoxycytidine."

( i x ) FEATURE:
        ( A ) NAME/KEY: modified_base
        ( B ) LOCATION: 10
        ( D ) OTHER INFORMATION: /note= "This position is C'= 5-methyl-2'-deoxycytidine."

( x i ) SEQUENCE DESCRIPTION: SEQ ID NO:1:

TNTNTNTNTN TTTTT                1 5

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 2
        ( D ) OTHER INFORMATION: /note= "This position is C'= 5-methyl-2'-deoxycytidine."

( i x ) FEATURE:
  ( A ) NAME/KEY: modified_base
  ( B ) LOCATION: 4
  ( D ) OTHER INFORMATION: /note= "This position is C'=
    5-methyl-2'-deoxycytidine."

( i x ) FEATURE:
  ( A ) NAME/KEY: modified_base
  ( B ) LOCATION: 6
  ( D ) OTHER INFORMATION: /note= "This position is C'=
    5-methyl-2'-deoxycytidine."

( i x ) FEATURE:
  ( A ) NAME/KEY: modified_base
  ( B ) LOCATION: 8
  ( D ) OTHER INFORMATION: /note= "This position is C'=
    5-methyl-2'-deoxycytidine."

( i x ) FEATURE:
  ( A ) NAME/KEY: modified_base
  ( B ) LOCATION: 10
  ( D ) OTHER INFORMATION: /note= "This position is C'=
    5-methyl-2'-deoxycytidine."

( i x ) FEATURE:
  ( A ) NAME/KEY: modified_base
  ( B ) LOCATION: 11
  ( D ) OTHER INFORMATION: /note= "This position is U* =
    5-(1- propynyl)-2'-deoxyuridine."

( i x ) FEATURE:
  ( A ) NAME/KEY: modified_base
  ( B ) LOCATION: 12
  ( D ) OTHER INFORMATION: /note= "This position is U* =
    5-(1- propynyl)-2'-deoxyuridine."

( i x ) FEATURE:
  ( A ) NAME/KEY: modified_base
  ( B ) LOCATION: 13
  ( D ) OTHER INFORMATION: /note= "This position is U* =
    5-(1- propynyl)-2'-deoxyuridine."

( i x ) FEATURE:
  ( A ) NAME/KEY: modified_base
  ( B ) LOCATION: 14
  ( D ) OTHER INFORMATION: /note= "This position is U* =
    5-(1- propynyl)-2'-deoxyuridine."

( i x ) FEATURE:
  ( A ) NAME/KEY: modified_base
  ( B ) LOCATION: 15
  ( D ) OTHER INFORMATION: /note= "This position is U* =
    5-(1- propynyl)-2'-deoxyuridine."

( x i ) SEQUENCE DESCRIPTION: SEQ ID NO:2:

T N T N T N T N T N N N N N N            1 5

( 2 ) INFORMATION FOR SEQ ID NO:3:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i x ) FEATURE:
  ( A ) NAME/KEY: modified_base
  ( B ) LOCATION: 2
  ( D ) OTHER INFORMATION: /note= "This position is C'=
    5-methyl-2'-deoxycytidine."

( i x ) FEATURE:
  ( A ) NAME/KEY: modified_base
  ( B ) LOCATION: 4
  ( D ) OTHER INFORMATION: /note= "This position is C'=
    5-methyl-2'-deoxycytidine."

( i x ) FEATURE:

( A ) NAME/KEY: modified_base
                    ( B ) LOCATION: 6
                    ( D ) OTHER INFORMATION: /note= "This position is C'=
                          5-methyl-2'-deoxycytidine."

( i x ) FEATURE:
                    ( A ) NAME/KEY: modified_base
                    ( B ) LOCATION: 7
                    ( D ) OTHER INFORMATION: /note= "This position is U* =
                          5-(1- propynyl)-2'-deoxyuridine."

( i x ) FEATURE:
                    ( A ) NAME/KEY: modified_base
                    ( B ) LOCATION: 8
                    ( D ) OTHER INFORMATION: /note= "This position is C'=
                          5-methyl-2'-deoxycytidine."

( i x ) FEATURE:
                    ( A ) NAME/KEY: modified_base
                    ( B ) LOCATION: 9
                    ( D ) OTHER INFORMATION: /note= "This position is U* =
                          5-(1- propynyl)-2'-deoxyuridine."

( i x ) FEATURE:
                    ( A ) NAME/KEY: modified_base
                    ( B ) LOCATION: 10
                    ( D ) OTHER INFORMATION: /note= "This position is C'=
                          5-methyl-2'-deoxycytidine."

( i x ) FEATURE:
                    ( A ) NAME/KEY: modified_base
                    ( B ) LOCATION: 11
                    ( D ) OTHER INFORMATION: /note= "This position is U* =
                          5-(1- propynyl)-2'-deoxyuridine."

( i x ) FEATURE:
                    ( A ) NAME/KEY: modified_base
                    ( B ) LOCATION: 13
                    ( D ) OTHER INFORMATION: /note= "This position is U* =
                          5-(1- propynyl)-2'-deoxyuridine."

( i x ) FEATURE:
                    ( A ) NAME/KEY: modified_base
                    ( B ) LOCATION: 15
                    ( D ) OTHER INFORMATION: /note= "This position is U* =
                          5-(1- propynyl)-2'-deoxyuridine."

( x i ) SEQUENCE DESCRIPTION: SEQ ID NO:3:

TNTNTNNNNN NTNTN                                                                                              1 5

( 2 ) INFORMATION FOR SEQ ID NO:4:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:4:

AGAGAGAGAG AAAAA                                                                                              1 5

( 2 ) INFORMATION FOR SEQ ID NO:5:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: modified_base
                    ( B ) LOCATION: 2
                    ( D ) OTHER INFORMATION: /note= "This position is C* =
                          5-(1- propynyl)-2'-deoxycytidine."

( i x ) FEATURE:

(A) NAME/KEY: modified_base
(B) LOCATION: 4
(D) OTHER INFORMATION: /note= "This position is C* = 5-(1- propynyl)-2'-deoxycytidine."

(ix) FEATURE:
(A) NAME/KEY: modified_base
(B) LOCATION: 6
(D) OTHER INFORMATION: /note= "This position is C* = 5-(1- propynyl)-2'-deoxycytidine."

(ix) FEATURE:
(A) NAME/KEY: modified_base
(B) LOCATION: 8
(D) OTHER INFORMATION: /note= "This position is C* = 5-(1- propynyl)-2'-deoxycytidine."

(ix) FEATURE:
(A) NAME/KEY: modified_base
(B) LOCATION: 10
(D) OTHER INFORMATION: /note= "This position is C* = 5-(1- propynyl)-2'-deoxycytidine."

(xi) SEQUENCE DESCRIPTION: SEQ ID NO:5:

TNTNTNTNTN TTTTT 15

(2) INFORMATION FOR SEQ ID NO:6:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:6:

AAAAGAGAG AGAGA 15

(2) INFORMATION FOR SEQ ID NO:7:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: modified_base
(B) LOCATION: 1
(D) OTHER INFORMATION: /note= "This position is U* = 5-(1- propynyl)-2'-deoxyuridine."

(ix) FEATURE:
(A) NAME/KEY: modified_base
(B) LOCATION: 2
(D) OTHER INFORMATION: /note= "This position is C'= 5-methyl-2'-deoxycytidine."

(ix) FEATURE:
(A) NAME/KEY: modified_base
(B) LOCATION: 3
(D) OTHER INFORMATION: /note= "This position is U* = 5-(1- propynyl)-2'-deoxyuridine."

(ix) FEATURE:
(A) NAME/KEY: modified_base
(B) LOCATION: 4
(D) OTHER INFORMATION: /note= "This position is C'= 5-methyl-2'-deoxycytidine."

(ix) FEATURE:
(A) NAME/KEY: modified_base
(B) LOCATION: 5
(D) OTHER INFORMATION: /note= "This position is U* = 5-(1- propynyl)-2'-deoxyuridine."

(ix) FEATURE:

( A ) NAME/KEY: modified_base
                    ( B ) LOCATION: 6
                    ( D ) OTHER INFORMATION: /note= "This position is C'=
                            5-methyl-2'-deoxycytidine."

( i x ) FEATURE:
                    ( A ) NAME/KEY: modified_base
                    ( B ) LOCATION: 7
                    ( D ) OTHER INFORMATION: /note= "This position is U* =
                            5-(1- propynyl)-2'-deoxyuridine."

( i x ) FEATURE:
                    ( A ) NAME/KEY: modified_base
                    ( B ) LOCATION: 8
                    ( D ) OTHER INFORMATION: /note= "This position is C'=
                            5-methyl-2'-deoxycytidine."

( i x ) FEATURE:
                    ( A ) NAME/KEY: modified_base
                    ( B ) LOCATION: 9
                    ( D ) OTHER INFORMATION: /note= "This position is U* =
                            5-(1- propynyl)-2'-deoxyuridine."

( i x ) FEATURE:
                    ( A ) NAME/KEY: modified_base
                    ( B ) LOCATION: 10
                    ( D ) OTHER INFORMATION: /note= "This position is C'=
                            5-methyl-2'-deoxycytidine."

( i x ) FEATURE:
                    ( A ) NAME/KEY: modified_base
                    ( B ) LOCATION: 11
                    ( D ) OTHER INFORMATION: /note= "This position is U* =
                            5-(1- propynyl)-2'-deoxyuridine."

( i x ) FEATURE:
                    ( A ) NAME/KEY: modified_base
                    ( B ) LOCATION: 12
                    ( D ) OTHER INFORMATION: /note= "This position is U* =
                            5-(1- propynyl)-2'-deoxyuridine."

( i x ) FEATURE:
                    ( A ) NAME/KEY: modified_base
                    ( B ) LOCATION: 13
                    ( D ) OTHER INFORMATION: /note= "This position is U* =
                            5-(1- propynyl)-2'-deoxyuridine."

( i x ) FEATURE:
                    ( A ) NAME/KEY: modified_base
                    ( B ) LOCATION: 14
                    ( D ) OTHER INFORMATION: /note= "This position is U* =
                            5-(1- propynyl)-2'-deoxyuridine."

( i x ) FEATURE:
                    ( A ) NAME/KEY: modified_base
                    ( B ) LOCATION: 15
                    ( D ) OTHER INFORMATION: /note= "This position is U* =
                            5-(1- propynyl)-2'-deoxyuridine."

( x i ) SEQUENCE DESCRIPTION: SEQ ID NO:7:

NNNNNNNNN NNNNN                                                                                         1 5

( 2 ) INFORMATION FOR SEQ ID NO:8:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: modified_base
                    ( B ) LOCATION: 2
                    ( D ) OTHER INFORMATION: /note= "This position is C'=
                            5-methyl-2'-deoxycytidine."

( i x ) FEATURE:
                    ( A ) NAME/KEY: modified_base (B) LOCATION: 4
                (D) OTHER INFORMATION: /note= "This position is C'=
                    5-methyl-2'-deoxycytidine."

(ix) FEATURE:
                (A) NAME/KEY: modified_base
                (B) LOCATION: 6
                (D) OTHER INFORMATION: /note= "This position is C'=
                    5-methyl-2'-deoxycytidine."

(ix) FEATURE:
                (A) NAME/KEY: modified_base
                (B) LOCATION: 7
                (D) OTHER INFORMATION: /note= "This position is U'=
                    5-(3-methyl- 1-butynyl)uracil."

(ix) FEATURE:
                (A) NAME/KEY: modified_base
                (B) LOCATION: 8
                (D) OTHER INFORMATION: /note= "This position is C'=
                    5-methyl-2'-deoxycytidine."

(ix) FEATURE:
                (A) NAME/KEY: modified_base
                (B) LOCATION: 9
                (D) OTHER INFORMATION: /note= "This position is U'=
                    5-(3-methyl- 1-butynyl)uracil."

(ix) FEATURE:
                (A) NAME/KEY: modified_base
                (B) LOCATION: 11
                (D) OTHER INFORMATION: /note= "This position is U'=
                    5-(3-methyl- 1-butynyl)uracil."

(ix) FEATURE:
                (A) NAME/KEY: modified_base
                (B) LOCATION: 13
                (D) OTHER INFORMATION: /note= "This position is U'=
                    5-(3-methyl- 1-butynyl)uracil."

(ix) FEATURE:
                (A) NAME/KEY: modified_base
                (B) LOCATION: 15
                (D) OTHER INFORMATION: /note= "This position is U'=
                    5-(3-methyl- 1-butynyl)uracil."

(xi) SEQUENCE DESCRIPTION: SEQ ID NO:8:

T N T N T N N N N C  N T N T N                                                                                              15

(2) INFORMATION FOR SEQ ID NO:9:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 2
            (D) OTHER INFORMATION: /note= "This position is C'=
                5-methyl-2'-deoxycytidine."

(ix) FEATURE:
            (A) NAME/KEY: modified_base
            (B) LOCATION: 4
            (D) OTHER INFORMATION: /note= "This position is C'=
                5-methyl-2'-deoxycytidine."

(ix) FEATURE:
            (A) NAME/KEY: modified_base
            (B) LOCATION: 6
            (D) OTHER INFORMATION: /note= "This position is C'=
                5-methyl-2'-deoxycytidine."

(ix) FEATURE:
            (A) NAME/KEY: modified_base
            (B) LOCATION: 8

-continued ( D ) OTHER INFORMATION: /note= "This position is C'=
                        5-methyl-2'-deoxycytidine."

( i x ) FEATURE:
                    ( A ) NAME/KEY: modified_base
                    ( B ) LOCATION: 10
                    ( D ) OTHER INFORMATION: /note= "This position is C'=
                        5-methyl-2'-deoxycytidine."

( i x ) FEATURE:
                    ( A ) NAME/KEY: modified_base
                    ( B ) LOCATION: 11
                    ( D ) OTHER INFORMATION: /note= "This position is U'=
                        5-(3-methyl- 1-butynyl)uracil."

( i x ) FEATURE:
                    ( A ) NAME/KEY: modified_base
                    ( B ) LOCATION: 12
                    ( D ) OTHER INFORMATION: /note= "This position is U'=
                        5-(3-methyl- 1-butynyl)uracil."

( i x ) FEATURE:
                    ( A ) NAME/KEY: modified_base
                    ( B ) LOCATION: 13
                    ( D ) OTHER INFORMATION: /note= "This position is U'=
                        5-(3-methyl- 1-butynyl)uracil."

( i x ) FEATURE:
                    ( A ) NAME/KEY: modified_base
                    ( B ) LOCATION: 14
                    ( D ) OTHER INFORMATION: /note= "This position is U'=
                        5-(3-methyl- 1-butynyl)uracil."

( i x ) FEATURE:
                    ( A ) NAME/KEY: modified_base
                    ( B ) LOCATION: 15
                    ( D ) OTHER INFORMATION: /note= "This position is U'=
                        5-(3-methyl- 1-butynyl)uracil."

( x i ) SEQUENCE DESCRIPTION: SEQ ID NO:9:

TNTNTNTNTN NNNNN                                                                        1 5

( 2 ) INFORMATION FOR SEQ ID NO:10:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:10:

AGAGAGAGAG AAAAAGGA                                                                     1 8

( 2 ) INFORMATION FOR SEQ ID NO:11:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:11:

TCTCTCTCTC TTTTTCCT                                                                     1 8

( 2 ) INFORMATION FOR SEQ ID NO:12:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:12:

AAAAAGAGAG AGAGA 15

(2) INFORMATION FOR SEQ ID NO:13:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (ix) FEATURE:
  (A) NAME/KEY: modified_base
  (B) LOCATION: 1
  (D) OTHER INFORMATION: /note= "This position is U* = 5-(1- propynyl)-2'-deoxyuridine."

(ix) FEATURE:
  (A) NAME/KEY: modified_base
  (B) LOCATION: 2
  (D) OTHER INFORMATION: /note= "This position is C* = 5-(1- propynyl)-2'-deoxycytidine."

(ix) FEATURE:
  (A) NAME/KEY: modified_base
  (B) LOCATION: 3
  (D) OTHER INFORMATION: /note= "This position is U* = 5-(1- propynyl)-2'-deoxyuridine."

(ix) FEATURE:
  (A) NAME/KEY: modified_base
  (B) LOCATION: 4
  (D) OTHER INFORMATION: /note= "This position is C* = 5-(1- propynyl)-2'-deoxycytidine."

(ix) FEATURE:
  (A) NAME/KEY: modified_base
  (B) LOCATION: 6
  (D) OTHER INFORMATION: /note= "This position is C* = 5-(1- propynyl)-2'-deoxycytidine."

(ix) FEATURE:
  (A) NAME/KEY: modified_base
  (B) LOCATION: 7
  (D) OTHER INFORMATION: /note= "This position is U* = 5-(1- propynyl)-2'-deoxyuridine."

(ix) FEATURE:
  (A) NAME/KEY: modified_base
  (B) LOCATION: 8
  (D) OTHER INFORMATION: /note= "This position is C* = 5-(1- propynyl)-2'-deoxycytidine."

(ix) FEATURE:
  (A) NAME/KEY: modified_base
  (B) LOCATION: 9
  (D) OTHER INFORMATION: /note= "This position is U* = 5-(1- propynyl)-2'-deoxyuridine."

(ix) FEATURE:
  (A) NAME/KEY: modified_base
  (B) LOCATION: 10
  (D) OTHER INFORMATION: /note= "This position is U* = 5-(1- propynyl)-2'-deoxyuridine."

(ix) FEATURE:
  (A) NAME/KEY: modified_base
  (B) LOCATION: 11
  (D) OTHER INFORMATION: /note= "This position is C* = 5-(1- propynyl)-2'-deoxycytidine."

(ix) FEATURE:
  (A) NAME/KEY: modified_base
  (B) LOCATION: 12
  (D) OTHER INFORMATION: /note= "This position is U* = 5-(1- propynyl)-2'-deoxyuridine."

(ix) FEATURE:
  (A) NAME/KEY: modified_base
  (B) LOCATION: 13

( D ) OTHER INFORMATION: /note= "This position is U* =
5-(1- propynyl)-2'-deoxyuridine."

( i x ) FEATURE:
( A ) NAME/KEY: modified_base
( B ) LOCATION: 14
( D ) OTHER INFORMATION: /note= "This position is U* =
5-(1- propynyl)-2'-deoxyuridine."

( x i ) SEQUENCE DESCRIPTION: SEQ ID NO:13:

NCNCNCNCNN NNNNN 15

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i x ) FEATURE:
( A ) NAME/KEY: modified_base
( B ) LOCATION: 6
( D ) OTHER INFORMATION: /note= "This position is C'=
5-methyl-2'-deoxycytidine."

( i x ) FEATURE:
( A ) NAME/KEY: modified_base
( B ) LOCATION: 9
( D ) OTHER INFORMATION: /note= "This position is C'=
5-methyl-2'-deoxycytidine."

( i x ) FEATURE:
( A ) NAME/KEY: modified_base
( B ) LOCATION: 17
( D ) OTHER INFORMATION: /note= "This position is C'=
5-methyl-2'-deoxycytidine."

( i x ) FEATURE:
( A ) NAME/KEY: modified_base
( B ) LOCATION: 20
( D ) OTHER INFORMATION: /note= "This position is C'=
5-methyl-2'-deoxycytidine."

( x i ) SEQUENCE DESCRIPTION: SEQ ID NO:14:

ATTTNTTNA TTTTTNTTN 20

( 2 ) INFORMATION FOR SEQ ID NO:15:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i x ) FEATURE:
( A ) NAME/KEY: modified_base
( B ) LOCATION: 2
( D ) OTHER INFORMATION: /note= "This position is U* =
5-(1- propynyl)-2'-deoxyuridine."

( i x ) FEATURE:
( A ) NAME/KEY: modified_base
( B ) LOCATION: 3
( D ) OTHER INFORMATION: /note= "This position is U* =
5-(1- propynyl)-2'-deoxyuridine."

( i x ) FEATURE:
( A ) NAME/KEY: modified_base
( B ) LOCATION: 4
( D ) OTHER INFORMATION: /note= "This position is U* =
5-(1- propynyl)-2'-deoxyuridine."

( i x ) FEATURE:
( A ) NAME/KEY: modified_base
( B ) LOCATION: 5

(D) OTHER INFORMATION: /note= "This position is U* = 5-(1- propynyl)-2'-deoxyuridine."

(ix) FEATURE:
    (A) NAME/KEY: modified_base
    (B) LOCATION: 6
    (D) OTHER INFORMATION: /note= "This position is C'= 5-methyl-2'-deoxycytidine."

(ix) FEATURE:
    (A) NAME/KEY: modified_base
    (B) LOCATION: 7
    (D) OTHER INFORMATION: /note= "This position is U* = 5-(1- propynyl)-2'-deoxyuridine."

(ix) FEATURE:
    (A) NAME/KEY: modified_base
    (B) LOCATION: 8
    (D) OTHER INFORMATION: /note= "This position is U* = 5-(1- propynyl)-2'-deoxyuridine."

(ix) FEATURE:
    (A) NAME/KEY: modified_base
    (B) LOCATION: 9
    (D) OTHER INFORMATION: /note= "This position is C'= 5-methyl-2'-deoxycytidine."

(ix) FEATURE:
    (A) NAME/KEY: modified_base
    (B) LOCATION: 11
    (D) OTHER INFORMATION: /note= "This position is U* = 5-(1- propynyl)-2'-deoxyuridine."

(ix) FEATURE:
    (A) NAME/KEY: modified_base
    (B) LOCATION: 12
    (D) OTHER INFORMATION: /note= "This position is U* = 5-(1- propynyl)-2'-deoxyuridine."

(ix) FEATURE:
    (A) NAME/KEY: modified_base
    (B) LOCATION: 13
    (D) OTHER INFORMATION: /note= "This position is U* = 5-(1- propynyl)-2'-deoxyuridine."

(ix) FEATURE:
    (A) NAME/KEY: modified_base
    (B) LOCATION: 14
    (D) OTHER INFORMATION: /note= "This position is U* = 5-(1- propynyl)-2'-deoxyuridine."

(ix) FEATURE:
    (A) NAME/KEY: modified_base
    (B) LOCATION: 15
    (D) OTHER INFORMATION: /note= "This position is U* = 5-(1- propynyl)-2'-deoxyuridine."

(ix) FEATURE:
    (A) NAME/KEY: modified_base
    (B) LOCATION: 16
    (D) OTHER INFORMATION: /note= "This position is U* = 5-(1- propynyl)-2'-deoxyuridine."

(ix) FEATURE:
    (A) NAME/KEY: modified_base
    (B) LOCATION: 17
    (D) OTHER INFORMATION: /note= "This position is C'= 5-methyl-2'-deoxycytidine."

(ix) FEATURE:
    (A) NAME/KEY: modified_base
    (B) LOCATION: 18
    (D) OTHER INFORMATION: /note= "This position is U* = 5-(1- propynyl)-2'-deoxyuridine."

(ix) FEATURE:
    (A) NAME/KEY: modified_base
    (B) LOCATION: 19
    (D) OTHER INFORMATION: /note= "This position is U* = 5-(1- propynyl)-2'-deoxyuridine."

( i x ) FEATURE:
    ( A ) NAME/KEY: modified_base
    ( B ) LOCATION: 20
    ( D ) OTHER INFORMATION: /note= "This position is C'=
        5-methyl-2'-deoxycytidine."

( x i ) SEQUENCE DESCRIPTION: SEQ ID NO:15:

ANNNNNNNNA NNNNNNNNNN         20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 2
        ( D ) OTHER INFORMATION: /note= "This position is U* =
            5-(1- propynyl)-2'-deoxyuridine."

( i x ) FEATURE:
        ( A ) NAME/KEY: modified_base
        ( B ) LOCATION: 3
        ( D ) OTHER INFORMATION: /note= "This position is U* =
            5-(1- propynyl)-2'-deoxyuridine."

( i x ) FEATURE:
        ( A ) NAME/KEY: modified_base
        ( B ) LOCATION: 4
        ( D ) OTHER INFORMATION: /note= "This position is U* =
            5-(1- propynyl)-2'-deoxyuridine."

( i x ) FEATURE:
        ( A ) NAME/KEY: modified_base
        ( B ) LOCATION: 5
        ( D ) OTHER INFORMATION: /note= "This position is U* =
            5-(1- propynyl)-2'-deoxyuridine."

( i x ) FEATURE:
        ( A ) NAME/KEY: modified_base
        ( B ) LOCATION: 6
        ( D ) OTHER INFORMATION: /note= "This position is C* = 5
            propynyl cytosine."

( i x ) FEATURE:
        ( A ) NAME/KEY: modified_base
        ( B ) LOCATION: 7
        ( D ) OTHER INFORMATION: /note= "This position is U* =
            5-(1- propynyl)-2'-deoxyuridine."

( i x ) FEATURE:
        ( A ) NAME/KEY: modified_base
        ( B ) LOCATION: 8
        ( D ) OTHER INFORMATION: /note= "This position is U* =
            5-(1- propynyl)-2'-deoxyuridine."

( i x ) FEATURE:
        ( A ) NAME/KEY: modified_base
        ( B ) LOCATION: 9
        ( D ) OTHER INFORMATION: /note= "This position is C* =
            5-(1- propynyl)-2'-deoxycytidine."

( i x ) FEATURE:
        ( A ) NAME/KEY: modified_base
        ( B ) LOCATION: 11
        ( D ) OTHER INFORMATION: /note= "This position is U* =
            5-(1- propynyl)-2'-deoxyuridine."

( i x ) FEATURE:
        ( A ) NAME/KEY: modified_base
        ( B ) LOCATION: 12
        ( D ) OTHER INFORMATION: /note= "This position is U* =
            5-(1- propynyl)-2'-deoxyuridine."

( i x ) FEATURE:
    ( A ) NAME/KEY: modified_base
    ( B ) LOCATION: 13
    ( D ) OTHER INFORMATION: /note= "This position is U* =
        5-(1- propynyl)-2'-deoxyuridine."

( i x ) FEATURE:
    ( A ) NAME/KEY: modified_base
    ( B ) LOCATION: 14
    ( D ) OTHER INFORMATION: /note= "This position is U* =
        5-(1- propynyl)-2'-deoxyuridine."

( i x ) FEATURE:
    ( A ) NAME/KEY: modified_base
    ( B ) LOCATION: 15
    ( D ) OTHER INFORMATION: /note= "This position is U* =
        5-(1- propynyl)-2'-deoxyuridine."

( i x ) FEATURE:
    ( A ) NAME/KEY: modified_base
    ( B ) LOCATION: 16
    ( D ) OTHER INFORMATION: /note= "This position is U* =
        5-(1- propynyl)-2'-deoxyuridine."

( i x ) FEATURE:
    ( A ) NAME/KEY: modified_base
    ( B ) LOCATION: 17
    ( D ) OTHER INFORMATION: /note= "This position is C* =
        5-(1- propynyl)-2'-deoxycytidine."

( i x ) FEATURE:
    ( A ) NAME/KEY: modified_base
    ( B ) LOCATION: 18
    ( D ) OTHER INFORMATION: /note= "This position is U* =
        5-(1- propynyl)-2'-deoxyuridine."

( i x ) FEATURE:
    ( A ) NAME/KEY: modified_base
    ( B ) LOCATION: 19
    ( D ) OTHER INFORMATION: /note= "This position is U* =
        5-(1- propynyl)-2'-deoxyuridine."

( i x ) FEATURE:
    ( A ) NAME/KEY: modified_base
    ( B ) LOCATION: 20
    ( D ) OTHER INFORMATION: /note= "This position is C* =
        5-(1- propynyl)-2'-deoxycytidine."

( x i ) SEQUENCE DESCRIPTION: SEQ ID NO:16:

A N N N N N N N N A    N N N N N N N N N N                            2 0

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
    ( A ) NAME/KEY: misc_difference
    ( B ) LOCATION: replace(2, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(3, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(4, "")
    ( D ) OTHER INFORMATION: /note= "This position is U* =
        5-(1- propynyl)-2'-deoxyuridine."

( i x ) FEATURE:

(A) NAME/KEY: misc_difference
(B) LOCATION: replace(5, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(6, "")
(D) OTHER INFORMATION: /note= "This position is C* = 5-(1- propynyl)-2'-deoxycytidine."

(ix) FEATURE:
(A) NAME/KEY: misc_difference
(B) LOCATION: replace(7, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(8, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(9, "")
(D) OTHER INFORMATION: /note= "This position is C* = 5-(1- propynyl)-2'-deoxycytidine."

(ix) FEATURE:
(A) NAME/KEY: misc_difference
(B) LOCATION: replace(11, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(12, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(13, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(14, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(15, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(16, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(17, "")
(D) OTHER INFORMATION: /note= "This position is C* = 5-(1- propynyl)-2'-deoxycytidine."

(ix) FEATURE:
(A) NAME/KEY: misc_difference
(B) LOCATION: replace(18, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(19, "")

(D) OTHER INFORMATION: /note= "This position is U* = 
5-(1- propynyl)-2'-deoxyuridine."

(ix) FEATURE:
(A) NAME/KEY: misc_difference
(B) LOCATION: replace(20, "")
(D) OTHER INFORMATION: /note= "This position is C* = 
5-(1- propynyl)-2'-deoxycytidine."

(xi) SEQUENCE DESCRIPTION: SEQ ID NO:17:

ANNNNNNNNA NNNNNNNNNN                                              20

(2) INFORMATION FOR SEQ ID NO:18:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(1, "")
(D) OTHER INFORMATION: /note= "This position is C* = 
5-(1- propynyl)-2'-deoxycytidine."

(ix) FEATURE:
(A) NAME/KEY: misc_difference
(B) LOCATION: replace(2, "")
(D) OTHER INFORMATION: /note= "This position is U* = 
5-(1- propynyl)-2'-deoxyuridine."

(ix) FEATURE:
(A) NAME/KEY: misc_difference
(B) LOCATION: replace(3, "")
(D) OTHER INFORMATION: /note= "This position is U* = 
5-(1- propynyl)-2'-deoxyuridine."

(ix) FEATURE:
(A) NAME/KEY: misc_difference
(B) LOCATION: replace(4, "")
(D) OTHER INFORMATION: /note= "This position is C* = 
5-(1- propynyl)-2'-deoxycytidine."

(ix) FEATURE:
(A) NAME/KEY: misc_difference
(B) LOCATION: replace(6, "")
(D) OTHER INFORMATION: /note= "This position is U* = 
5-(1- propynyl)-2'-deoxyuridine."

(ix) FEATURE:
(A) NAME/KEY: misc_difference
(B) LOCATION: replace(7, "")
(D) OTHER INFORMATION: /note= "This position is U* = 
5-(1- propynyl)-2'-deoxyuridine."

(ix) FEATURE:
(A) NAME/KEY: misc_difference
(B) LOCATION: replace(8, "")
(D) OTHER INFORMATION: /note= "This position is U* = 
5-(1- propynyl)-2'-deoxyuridine."

(ix) FEATURE:
(A) NAME/KEY: misc_difference
(B) LOCATION: replace(9, "")
(D) OTHER INFORMATION: /note= "This position is U* = 
5-(1- propynyl)-2'-deoxyuridine."

(ix) FEATURE:
(A) NAME/KEY: misc_difference
(B) LOCATION: replace(10, "")
(D) OTHER INFORMATION: /note= "This position is U* = 
5-(1- propynyl)-2'-deoxyuridine."

(ix) FEATURE:
(A) NAME/KEY: misc_difference
(B) LOCATION: replace(11, "")
(D) OTHER INFORMATION: /note= "This position is U* =

5-(1- propynyl)-2'-deoxyuridine."

( i x ) FEATURE:
    ( A ) NAME/KEY: misc_difference
    ( B ) LOCATION: replace(12, "")
    ( D ) OTHER INFORMATION: /note= "This position is C* =
        5-(1- propynyl)-2'-deoxycytidine."

( i x ) FEATURE:
    ( A ) NAME/KEY: misc_difference
    ( B ) LOCATION: replace(13, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(14, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(15, "")
    ( D ) OTHER INFORMATION: /note= "This position is C* =
        5-(1- propynyl)-2'-deoxycytidine."

( x i ) SEQUENCE DESCRIPTION: SEQ ID NO:18:

NNNNANNNNN NNNNN          15

( 2 ) INFORMATION FOR SEQ ID NO:19:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i x ) FEATURE:
    ( A ) NAME/KEY: misc_difference
    ( B ) LOCATION: replace(1, "")
    ( D ) OTHER INFORMATION: /note= "This position is C* =
        5-(1- propynyl)-2'-deoxycytidine."

( i x ) FEATURE:
    ( A ) NAME/KEY: misc_difference
    ( B ) LOCATION: replace(2, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(3, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(4, "")
    ( D ) OTHER INFORMATION: /note= "This position is C* =
        5-(1- propynyl)-2'-deoxycytidine."

( i x ) FEATURE:
    ( A ) NAME/KEY: misc_difference
    ( B ) LOCATION: replace(6, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(7, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(8, "")
    ( D ) OTHER INFORMATION: /note= "This position is U* =
        5-(1- propynyl)-2'-deoxyuridine."

( i x ) FEATURE:
      ( A ) NAME/KEY: misc_difference
      ( B ) LOCATION: replace(9, "")
      ( D ) OTHER INFORMATION: /note= "This position is U* =
          5-(1- propynyl)-2'-deoxyuridine."

( i x ) FEATURE:
      ( A ) NAME/KEY: misc_difference
      ( B ) LOCATION: replace(10, "")
      ( D ) OTHER INFORMATION: /note= "This position is U* =
          5-(1- propynyl)-2'-deoxyuridine."

( i x ) FEATURE:
      ( A ) NAME/KEY: misc_difference
      ( B ) LOCATION: replace(11, "")
      ( D ) OTHER INFORMATION: /note= "This position is U* =
          5-(1- propynyl)-2'-deoxyuridine."

( i x ) FEATURE:
      ( A ) NAME/KEY: misc_difference
      ( B ) LOCATION: replace(12, "")
      ( D ) OTHER INFORMATION: /note= "This position is C* =
          5-(1- propynyl)-2'-deoxycytidine."

( i x ) FEATURE:
      ( A ) NAME/KEY: misc_difference
      ( B ) LOCATION: replace(13, "")
      ( D ) OTHER INFORMATION: /note= "This position is U* =
          5-(1- propynyl)-2'-deoxyuridine."

( x i ) SEQUENCE DESCRIPTION: SEQ ID NO:19:

NNNNANNNNN NNN                                                  13

( 2 ) INFORMATION FOR SEQ ID NO:20:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i x ) FEATURE:
      ( A ) NAME/KEY: misc_difference
      ( B ) LOCATION: replace(1, "")
      ( D ) OTHER INFORMATION: /note= "This position is C* =
          5-(1- propynyl)-2'-deoxycytidine."

( i x ) FEATURE:
      ( A ) NAME/KEY: misc_difference
      ( B ) LOCATION: replace(2, "")
      ( D ) OTHER INFORMATION: /note= "This position is U* =
          5-(1- propynyl)-2'-deoxyuridine."

( i x ) FEATURE:
      ( A ) NAME/KEY: misc_difference
      ( B ) LOCATION: replace(3, "")
      ( D ) OTHER INFORMATION: /note= "This position is U* =
          5-(1- propynyl)-2'-deoxyuridine."

( i x ) FEATURE:
      ( A ) NAME/KEY: misc_difference
      ( B ) LOCATION: replace(4, "")
      ( D ) OTHER INFORMATION: /note= "This position is C* =
          5-(1- propynyl)-2'-deoxycytidine."

( i x ) FEATURE:
      ( A ) NAME/KEY: misc_difference
      ( B ) LOCATION: replace(6, "")
      ( D ) OTHER INFORMATION: /note= "This position is U* =
          5-(1- propynyl)-2'-deoxyuridine."

( i x ) FEATURE:
      ( A ) NAME/KEY: misc_difference
      ( B ) LOCATION: replace(7, "")
      ( D ) OTHER INFORMATION: /note= "This position is U* =
          5-(1- propynyl)-2'-deoxyuridine."

( i x ) FEATURE:
 ( A ) NAME/KEY: misc_difference
 ( B ) LOCATION: replace(8, "")
 ( D ) OTHER INFORMATION: /note= "This position is U* = 5-(1- propynyl)-2'-deoxyuridine."

( i x ) FEATURE:
 ( A ) NAME/KEY: misc_difference
 ( B ) LOCATION: replace(9, "")
 ( D ) OTHER INFORMATION: /note= "This position is U* = 5-(1- propynyl)-2'-deoxyuridine."

( i x ) FEATURE:
 ( A ) NAME/KEY: misc_difference
 ( B ) LOCATION: replace(10, "")
 ( D ) OTHER INFORMATION: /note= "This position is U* = 5-(1- propynyl)-2'-deoxyuridine."

( i x ) FEATURE:
 ( A ) NAME/KEY: misc_difference
 ( B ) LOCATION: replace(11, "")
 ( D ) OTHER INFORMATION: /note= "This position is U* = 5-(1- propynyl)-2'-deoxyuridine."

( x i ) SEQUENCE DESCRIPTION: SEQ ID NO:20:

NNNNANNNNN N  11

( 2 ) INFORMATION FOR SEQ ID NO:21:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i x ) FEATURE:
  ( A ) NAME/KEY: misc_difference
  ( B ) LOCATION: replace(1, "")
  ( D ) OTHER INFORMATION: /note= "This position is C* = 5-(1- propynyl)-2'-deoxycytidine."

( i x ) FEATURE:
  ( A ) NAME/KEY: misc_difference
  ( B ) LOCATION: replace(2, "")
  ( D ) OTHER INFORMATION: /note= "This position is U* = 5-(1- propynyl)-2'-deoxyuridine."

( i x ) FEATURE:
  ( A ) NAME/KEY: misc_difference
  ( B ) LOCATION: replace(3, "")
  ( D ) OTHER INFORMATION: /note= "This position is U* = 5-(1- propynyl)-2'-deoxyuridine."

( i x ) FEATURE:
  ( A ) NAME/KEY: misc_difference
  ( B ) LOCATION: replace(4, "")
  ( D ) OTHER INFORMATION: /note= "This position is C* = 5-(1- propynyl)-2'-deoxycytidine."

( i x ) FEATURE:
  ( A ) NAME/KEY: misc_difference
  ( B ) LOCATION: replace(6, "")
  ( D ) OTHER INFORMATION: /note= "This position is U* = 5-(1- propynyl)-2'-deoxyuridine."

( i x ) FEATURE:
  ( A ) NAME/KEY: misc_difference
  ( B ) LOCATION: replace(7, "")
  ( D ) OTHER INFORMATION: /note= "This position is U* = 5-(1- propynyl)-2'-deoxyuridine."

( i x ) FEATURE:
  ( A ) NAME/KEY: misc_difference
  ( B ) LOCATION: replace(9, "")
  ( D ) OTHER INFORMATION: /note= "This position is U* = 5-(1- propynyl)-2'-deoxyuridine."

( i x ) FEATURE:

( A ) NAME/KEY: misc_difference
                    ( B ) LOCATION: replace(10, "")
                    ( D ) OTHER INFORMATION: /note= "This position is U* =
                            5-(1- propynyl)-2'-deoxyuridine."

( i x ) FEATURE:
                    ( A ) NAME/KEY: misc_difference
                    ( B ) LOCATION: replace(11, "")
                    ( D ) OTHER INFORMATION: /note= "This position is U* =
                            5-(1- propynyl)-2'-deoxyuridine."

( i x ) FEATURE:
                    ( A ) NAME/KEY: misc_difference
                    ( B ) LOCATION: replace(12, "")
                    ( D ) OTHER INFORMATION: /note= "This position is C* =
                            5-(1- propynyl)-2'-deoxycytidine."

( i x ) FEATURE:
                    ( A ) NAME/KEY: misc_difference
                    ( B ) LOCATION: replace(13, "")
                    ( D ) OTHER INFORMATION: /note= "This position is U* =
                            5-(1- propynyl)-2'-deoxyuridine."

( i x ) FEATURE:
                    ( A ) NAME/KEY: misc_difference
                    ( B ) LOCATION: replace(14, "")
                    ( D ) OTHER INFORMATION: /note= "This position is U* =
                            5-(1- propynyl)-2'-deoxyuridine."

( i x ) FEATURE:
                    ( A ) NAME/KEY: misc_difference
                    ( B ) LOCATION: replace(15, "")
                    ( D ) OTHER INFORMATION: /note= "This position is C* =
                            5-(1- propynyl)-2'-deoxycytidine."

( x i ) SEQUENCE DESCRIPTION: SEQ ID NO:21:

NNNNANNANN NNNNN                                                                                        1 5

( 2 ) INFORMATION FOR SEQ ID NO:22:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: misc_difference
                    ( B ) LOCATION: replace(1, "")
                    ( D ) OTHER INFORMATION: /note= "This position is C* =
                            5-(1- propynyl)-2'-deoxycytidine."

( i x ) FEATURE:
                    ( A ) NAME/KEY: misc_difference
                    ( B ) LOCATION: replace(2, "")
                    ( D ) OTHER INFORMATION: /note= "This position is U* =
                            5-(1- propynyl)-2'-deoxyuridine."

( i x ) FEATURE:
                    ( A ) NAME/KEY: misc_difference
                    ( B ) LOCATION: replace(3, "")
                    ( D ) OTHER INFORMATION: /note= "This position is U* =
                            5-(1- propynyl)-2'-deoxyuridine."

( i x ) FEATURE:
                    ( A ) NAME/KEY: misc_difference
                    ( B ) LOCATION: replace(4, "")
                    ( D ) OTHER INFORMATION: /note= "This position is U* =
                            5-(1- propynyl)-2'-deoxyuridine."

( i x ) FEATURE:
                    ( A ) NAME/KEY: misc_difference
                    ( B ) LOCATION: replace(5, "")
                    ( D ) OTHER INFORMATION: /note= "This position is C* =
                            5-(1- propynyl)-2'-deoxycytidine."

( i x ) FEATURE:
                    ( A ) NAME/KEY: misc_difference ( B ) LOCATION: replace(6, "")
                    ( D ) OTHER INFORMATION: /note= "This position is U* =
                        5-(1- propynyl)-2'-deoxyuridine."

( i x ) FEATURE:
                    ( A ) NAME/KEY: misc_difference
                    ( B ) LOCATION: replace(7, "")
                    ( D ) OTHER INFORMATION: /note= "This position is U* =
                        5-(1- propynyl)-2'-deoxyuridine."

( i x ) FEATURE:
                    ( A ) NAME/KEY: misc_difference
                    ( B ) LOCATION: replace(8, "")
                    ( D ) OTHER INFORMATION: /note= "This position is C* =
                        5-(1- propynyl)-2'-deoxycytidine."

( i x ) FEATURE:
                    ( A ) NAME/KEY: misc_difference
                    ( B ) LOCATION: replace(9, "")
                    ( D ) OTHER INFORMATION: /note= "This position is U* =
                        5-(1- propynyl)-2'-deoxyuridine."

( i x ) FEATURE:
                    ( A ) NAME/KEY: misc_difference
                    ( B ) LOCATION: replace(10, "")
                    ( D ) OTHER INFORMATION: /note= "This position is U* =
                        5-(1- propynyl)-2'-deoxyuridine."

( i x ) FEATURE:
                    ( A ) NAME/KEY: misc_difference
                    ( B ) LOCATION: replace(12, "")
                    ( D ) OTHER INFORMATION: /note= "This position is C* =
                        5-(1- propynyl-2'-deoxycytidine."

( i x ) FEATURE:
                    ( A ) NAME/KEY: misc_difference
                    ( B ) LOCATION: replace(13, "")
                    ( D ) OTHER INFORMATION: /note= "This position is U* =
                        5-(1- propynyl)-2'-deoxyuridine."

( i x ) FEATURE:
                    ( A ) NAME/KEY: misc_difference
                    ( B ) LOCATION: replace(14, "")
                    ( D ) OTHER INFORMATION: /note= "This position is U* =
                        5-(1- propynyl)-2'-deoxyuridine."

( i x ) FEATURE:
                    ( A ) NAME/KEY: misc_difference
                    ( B ) LOCATION: replace(15, "")
                    ( D ) OTHER INFORMATION: /note= "This position is C* =
                        5-(1- propynyl)-2'-deoxycytidine."

( x i ) SEQUENCE DESCRIPTION: SEQ ID NO:22:

NNNNNNNNN ANNNN                                                                                            1 5

( 2 ) INFORMATION FOR SEQ ID NO:23:

( i ) SEQUENCE CHARACTERISTICS:
                    ( A ) LENGTH: 23 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: misc_difference
                    ( B ) LOCATION: replace(1, "")
                    ( D ) OTHER INFORMATION: /note= "This position is U* =
                        5-(1- propynyl)-2'-deoxyuridine."

( i x ) FEATURE:
                    ( A ) NAME/KEY: misc_difference
                    ( B ) LOCATION: replace(2, "")
                    ( D ) OTHER INFORMATION: /note= "This position is U* =
                        5-(1- propynyl)-2'-deoxyuridine."

( i x ) FEATURE:
                    ( A ) NAME/KEY: misc_difference
                    ( B ) LOCATION: replace(4, "")

( D ) OTHER INFORMATION: /note= "This position is C'=
    5-methyl-2'-deoxycytidine."

( i x ) FEATURE:
    ( A ) NAME/KEY: misc_difference
    ( B ) LOCATION: replace(5, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(7, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(8, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(9, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(10, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(11, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(13, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(14, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(16, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(18, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(19, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(20, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(23, "")
    ( D ) OTHER INFORMATION: /note= "This position is U* =
        5-(1- propynyl)-2'-deoxyuridine."

( x i ) SEQUENCE DESCRIPTION: SEQ ID NO:23:

NNGNNGNNNN NANNANANNN AAN  23

( 2 ) INFORMATION FOR SEQ ID NO:24:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note= "This position is C* = 5-(1- propynyl)-2'-deoxycytidine."

( i x ) FEATURE:
        ( A ) NAME/KEY: misc_difference
        ( B ) LOCATION: replace(2, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(3, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(4, "")
        ( D ) OTHER INFORMATION: /note= "This position is C* = 5-(1- propynyl)-2'-deoxycytidine."

( i x ) FEATURE:
        ( A ) NAME/KEY: misc_difference
        ( B ) LOCATION: replace(6, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(7, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(8, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(9, "")
        ( D ) OTHER INFORMATION: /note= "This position is U* = 5-(1- propynyl)-2'-deoxyuridine."

( x i ) SEQUENCE DESCRIPTION: SEQ ID NO:24:

NNNNANNNN  9

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(2, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(4, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(5, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(7, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(8, "")
    ( D ) OTHER INFORMATION: /note= "This position is C'= 5-methyl-2'-deoxycytidine."

( i x ) FEATURE:
    ( A ) NAME/KEY: misc_difference
    ( B ) LOCATION: replace(9, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(10, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(11, "")
    ( D ) OTHER INFORMATION: /note= "This position is C'= 5-methyl-2'-deoxycytidine."

( i x ) FEATURE:
    ( A ) NAME/KEY: misc_difference
    ( B ) LOCATION: replace(12, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(13, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(14, "")
    ( D ) OTHER INFORMATION: /note= "This position is C'= 5-methyl-2'-deoxycytidine."

( i x ) FEATURE:
    ( A ) NAME/KEY: misc_difference
    ( B ) LOCATION: replace(15, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(16, "")
    ( D ) OTHER INFORMATION: /note= "This position is U* = 5-(1- propynyl)-2'-deoxyuridine."

( i x ) FEATURE:

(A) NAME/KEY: misc_difference
                (B) LOCATION: replace(17, "")
                (D) OTHER INFORMATION: /note= "This position is U* =
                    5-(1- propynyl)-2'-deoxyuridine."

(ix) FEATURE:
                (A) NAME/KEY: misc_difference
                (B) LOCATION: replace(18, "")
                (D) OTHER INFORMATION: /note= "This position is U* =
                    5-(1- propynyl)-2'-deoxyuridine."

(ix) FEATURE:
                (A) NAME/KEY: misc_difference
                (B) LOCATION: replace(19, "")
                (D) OTHER INFORMATION: /note= "This position is C'=
                    5-methyl-2'-deoxycytidine."

(ix) FEATURE:
                (A) NAME/KEY: misc_difference
                (B) LOCATION: replace(20, "")
                (D) OTHER INFORMATION: /note= "This position is U* =
                    5-(1- propynyl)-2'-deoxyuridine."

(xi) SEQUENCE DESCRIPTION: SEQ ID NO:25:

NNANNANNNN NNNNNNNNNN                                                                20

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:26:

GCCTCCTCAC TACTTCTGGA                                                                20

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:27:

CATCTTTGCA AAGCTTTTTG                                                                20

(2) INFORMATION FOR SEQ ID NO:28:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ix) FEATURE:
            (A) NAME/KEY: misc_difference
            (B) LOCATION: replace(2, "")
            (D) OTHER INFORMATION: /note= "This position is C'=
                5-methyl-2'-deoxycytidine."

(ix) FEATURE:
            (A) NAME/KEY: misc_difference
            (B) LOCATION: replace(4, "")
            (D) OTHER INFORMATION: /note= "This position is C'=
                5-methyl-2'-deoxycytidine."

(ix) FEATURE:
            (A) NAME/KEY: misc_difference
            (B) LOCATION: replace(6, "")
            (D) OTHER INFORMATION: /note= "This position is C'=
                5-methyl-2'-deoxycytidine."

( i x ) FEATURE:
    ( A ) NAME/KEY: misc_difference
    ( B ) LOCATION: replace(8, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(10, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(11, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(12, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(13, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(14, "")
    ( D ) OTHER INFORMATION: /note= "This position is U* =
        5-(1- propynyl)-2'-deoxyuridine."

( x i ) SEQUENCE DESCRIPTION: SEQ ID NO:28:

TNTNTNTNTN NNNNT              15

( 2 ) INFORMATION FOR SEQ ID NO:29:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(2, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(4, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(6, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(8, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(10, "")
        ( D ) OTHER INFORMATION: /note= "This position is C'=
            5-methyl-2'-deoxycytidine."

( i x ) FEATURE:

(A) NAME/KEY: misc_difference
(B) LOCATION: replace(11..12, "")
(D) OTHER INFORMATION: /note= "This position indicates a
    3'- thioformacetal linkage (3',5')."

(ix) FEATURE:
(A) NAME/KEY: misc_difference
(B) LOCATION: replace(13..14, "")
(D) OTHER INFORMATION: /note= "This position indicates a
    3'- thioformacetal linkage (3',5')."

(xi) SEQUENCE DESCRIPTION: SEQ ID NO:29:

TNTNTNTNTN TTTTT                                                                    15

(2) INFORMATION FOR SEQ ID NO:30:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(2, "")
(D) OTHER INFORMATION: /note= "This position is C'=
    5-methyl-2'-deoxycytidine."

(ix) FEATURE:
(A) NAME/KEY: misc_difference
(B) LOCATION: replace(4, "")
(D) OTHER INFORMATION: /note= "This position is C'=
    5-methyl-2'-deoxycytidine."

(ix) FEATURE:
(A) NAME/KEY: misc_difference
(B) LOCATION: replace(6, "")
(D) OTHER INFORMATION: /note= "This position is C'=
    5-methyl-2'-deoxycytidine."

(ix) FEATURE:
(A) NAME/KEY: misc_difference
(B) LOCATION: replace(8, "")
(D) OTHER INFORMATION: /note= "This position is C'=
    5-methyl-2'-deoxycytidine."

(ix) FEATURE:
(A) NAME/KEY: misc_difference
(B) LOCATION: replace(10, "")
(D) OTHER INFORMATION: /note= "This position is C'=
    5-methyl-2'-deoxycytidine."

(ix) FEATURE:
(A) NAME/KEY: misc_difference
(B) LOCATION: replace(11, "")
(D) OTHER INFORMATION: /note= "This position is U* =
    5-(1- propynyl)-2'-deoxyuridine."

(ix) FEATURE:
(A) NAME/KEY: misc_difference
(B) LOCATION: replace(11..12, "")
(D) OTHER INFORMATION: /note= "This position indicates a
    3'- thioformacetal linkage (3',5')."

(ix) FEATURE:
(A) NAME/KEY: misc_difference
(B) LOCATION: replace(12, "")
(D) OTHER INFORMATION: /note= "This position is U* =
    5-(1- propynyl)-2'-deoxyuridine."

(ix) FEATURE:
(A) NAME/KEY: misc_difference
(B) LOCATION: replace(13, "")
(D) OTHER INFORMATION: /note= "This position is U* =
    5-(1- propynyl)-2'-deoxyuridine."

(ix) FEATURE:
(A) NAME/KEY: misc_difference ( B ) LOCATION: replace(13..14, "")
( D ) OTHER INFORMATION: /note= "This position indicates a
3'- thioformacetal linkage (3',5')."

( i x ) FEATURE:
( A ) NAME/KEY: misc_difference
( B ) LOCATION: replace(14, "")
( D ) OTHER INFORMATION: /note= "This position is U* =
5-(1- propynyl)-2'-deoxyuridine."

( x i ) SEQUENCE DESCRIPTION: SEQ ID NO:30:

T N T N T N T N T N   N N N N T                                                                                                           1 5

( 2 ) INFORMATION FOR SEQ ID NO:31:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i x ) FEATURE:
( A ) NAME/KEY: misc_difference
( B ) LOCATION: replace(2, "")
( D ) OTHER INFORMATION: /note= "This position is C'=
5-methyl-2'-deoxycytidine."

( i x ) FEATURE:
( A ) NAME/KEY: misc_difference
( B ) LOCATION: replace(4, "")
( D ) OTHER INFORMATION: /note= "This position is C'=
5-methyl-2'-deoxycytidine."

( i x ) FEATURE:
( A ) NAME/KEY: misc_difference
( B ) LOCATION: replace(6, "")
( D ) OTHER INFORMATION: /note= "This position is C'=
5-methyl-2'-deoxycytidine."

( i x ) FEATURE:
( A ) NAME/KEY: misc_difference
( B ) LOCATION: replace(8, "")
( D ) OTHER INFORMATION: /note= "This position is C'=
5-methyl-2'-deoxycytidine."

( i x ) FEATURE:
( A ) NAME/KEY: misc_difference
( B ) LOCATION: replace(10, "")
( D ) OTHER INFORMATION: /note= "This position is C'=
5-methyl-2'-deoxycytidine."

( i x ) FEATURE:
( A ) NAME/KEY: misc_difference
( B ) LOCATION: replace(11, "")
( D ) OTHER INFORMATION: /note= "This position is U* =
5-(1- propynyl)-2'-deoxyuridine."

( i x ) FEATURE:
( A ) NAME/KEY: misc_difference
( B ) LOCATION: replace(11..12, "")
( D ) OTHER INFORMATION: /note= "This position indicates a
formacetal linkage (3',5')."

( i x ) FEATURE:
( A ) NAME/KEY: misc_difference
( B ) LOCATION: replace(12, "")
( D ) OTHER INFORMATION: /note= "This position is U* =
5-(1- propynyl)-2'-deoxyuridine."

( i x ) FEATURE:
( A ) NAME/KEY: misc_difference
( B ) LOCATION: replace(13, "")
( D ) OTHER INFORMATION: /note= "This position is U* =
5-(1- propynyl)-2'-deoxyuridine."

( i x ) FEATURE:
( A ) NAME/KEY: misc_difference
( B ) LOCATION: replace(13..14, "")

(D) OTHER INFORMATION: /note= "This position indicates a
    formacetal linkage (3',5')."

(ix) FEATURE:
    (A) NAME/KEY: misc_difference
    (B) LOCATION: replace(14, "")
    (D) OTHER INFORMATION: /note= "This position is U* =
        5-(1- propynyl)-2'-deoxyuridine."

(xi) SEQUENCE DESCRIPTION: SEQ ID NO:31:

TNTNTNTNTN NNNNT    15

(2) INFORMATION FOR SEQ ID NO:32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
    (A) NAME/KEY: misc_difference
    (B) LOCATION: replace(2, "")
    (D) OTHER INFORMATION: /note= "This position is C'=
        5-methyl-2'-deoxycytidine."

(ix) FEATURE:
    (A) NAME/KEY: misc_difference
    (B) LOCATION: replace(4, "")
    (D) OTHER INFORMATION: /note= "This position is C'=
        5-methyl-2'-deoxycytidine."

(ix) FEATURE:
    (A) NAME/KEY: misc_difference
    (B) LOCATION: replace(6, "")
    (D) OTHER INFORMATION: /note= "This position is C'=
        5-methyl-2'-deoxycytidine."

(ix) FEATURE:
    (A) NAME/KEY: misc_difference
    (B) LOCATION: replace(8, "")
    (D) OTHER INFORMATION: /note= "This position is C'=
        5-methyl-2'-deoxycytidine."

(ix) FEATURE:
    (A) NAME/KEY: misc_difference
    (B) LOCATION: replace(10, "")
    (D) OTHER INFORMATION: /note= "This position is C'=
        5-methyl-2'-deoxycytidine."

(ix) FEATURE:
    (A) NAME/KEY: misc_difference
    (B) LOCATION: replace(11, "")
    (D) OTHER INFORMATION: /note= "This position is U
        superscript P = 5-(2-Pyridinyl)-2'-Deoxyuridine."

(ix) FEATURE:
    (A) NAME/KEY: misc_difference
    (B) LOCATION: replace(12, "")
    (D) OTHER INFORMATION: /note= "This position is U
        superscript P = 5-(2-Pyridinyl)-2'-Deoxyuridine."

(ix) FEATURE:
    (A) NAME/KEY: misc_difference
    (B) LOCATION: replace(13, "")
    (D) OTHER INFORMATION: /note= "This position is U
        superscript P = 5-(2-Pyridinyl)-2'-Deoxyuridine."

(ix) FEATURE:
    (A) NAME/KEY: misc_difference
    (B) LOCATION: replace(14, "")
    (D) OTHER INFORMATION: /note= "This position is U
        superscript P = 5-(2-Pyridinyl)-2'-Deoxyuridine."

(ix) FEATURE:
    (A) NAME/KEY: misc_difference
    (B) LOCATION: replace(15, "")
    (D) OTHER INFORMATION: /note= "This position is U superscript P = 5-(2-Pyridinyl)-2'-Deoxyuridine."

( x i ) SEQUENCE DESCRIPTION: SEQ ID NO:32:

TNTNTNTNTN NNNNN 15

( 2 ) INFORMATION FOR SEQ ID NO:33:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(2, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(4, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(6, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(7, "")
        ( D ) OTHER INFORMATION: /note= "This position is U
            superscript P = 5-(2-Pyridinyl)-2'-Deoxyuridine."

( i x ) FEATURE:
        ( A ) NAME/KEY: misc_difference
        ( B ) LOCATION: replace(8, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(9, "")
        ( D ) OTHER INFORMATION: /note= "This position is U
            superscript P = 5-(2-Pyridinyl)-2'-Deoxyuridine."

( i x ) FEATURE:
        ( A ) NAME/KEY: misc_difference
        ( B ) LOCATION: replace(10, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(11, "")
        ( D ) OTHER INFORMATION: /note= "This position is U
            superscript P = 5-(2-Pyridinyl)-2'-Deoxyuridine."

( i x ) FEATURE:
        ( A ) NAME/KEY: misc_difference
        ( B ) LOCATION: replace(13, "")
        ( D ) OTHER INFORMATION: /note= "This position is U
            superscript P = 5-(2-Pyridinyl)-2'-Deoxyuridine."

( i x ) FEATURE:
        ( A ) NAME/KEY: misc_difference
        ( B ) LOCATION: replace(15, "")
        ( D ) OTHER INFORMATION: /note= "This position is U
            superscript P = 5-(2-Pyridinyl)-2'-Deoxyuridine."

( x i ) SEQUENCE DESCRIPTION: SEQ ID NO:33:

TNTNTNNNNN NTNTN 15

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(2, "")
        ( D ) OTHER INFORMATION: /note= "This position is C
            superscript P = 5-(2-Pyridinyl)-2'-Deoxycytidine."

( i x ) FEATURE:
        ( A ) NAME/KEY: misc_difference
        ( B ) LOCATION: replace(4, "")
        ( D ) OTHER INFORMATION: /note= "This position is C
            superscript P = 5-(2-Pyridinyl)-2'-Deoxycytidine."

( i x ) FEATURE:
        ( A ) NAME/KEY: misc_difference
        ( B ) LOCATION: replace(6, "")
        ( D ) OTHER INFORMATION: /note= "This position is C
            superscript P = 5-(2-Pyridinyl)-2'-Deoxycytidine."

( i x ) FEATURE:
        ( A ) NAME/KEY: misc_difference
        ( B ) LOCATION: replace(8, "")
        ( D ) OTHER INFORMATION: /note= "This position is C
            superscript P = 5-(2-Pyridinyl)-2'-Deoxycytidine."

( i x ) FEATURE:
        ( A ) NAME/KEY: misc_difference
        ( B ) LOCATION: replace(10, "")
        ( D ) OTHER INFORMATION: /note= "This position is C
            superscript P = 5-(2-Pyridinyl)-2'-Deoxycytidine."

( x i ) SEQUENCE DESCRIPTION: SEQ ID NO:34:

T N T N T N T N T   T T T T T                        1 5

( 2 ) INFORMATION FOR SEQ ID NO:35:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(2, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(4, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(6, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(8, "")
        ( D ) OTHER INFORMATION: /note= "This position is C'=
            5-methyl-2'-deoxycytidine."

( i x ) FEATURE:
        ( A ) NAME/KEY: misc_difference
        ( B ) LOCATION: replace(10, "")
        ( D ) OTHER INFORMATION: /note= "This position is C'=
            5-methyl-2'-deoxycytidine."

( i x ) FEATURE:
   ( A ) NAME/KEY: misc_difference
   ( B ) LOCATION: replace(11, "")
   ( D ) OTHER INFORMATION: /note= "This position is U superscript T = 5-(2-Thienyl)-2'-Deoxyuridine."

( i x ) FEATURE:
   ( A ) NAME/KEY: misc_difference
   ( B ) LOCATION: replace(12, "")
   ( D ) OTHER INFORMATION: /note= "This position is U superscript T = 5-(2-Thienyl)-2'-Deoxyuridine."

( i x ) FEATURE:
   ( A ) NAME/KEY: misc_difference
   ( B ) LOCATION: replace(13, "")
   ( D ) OTHER INFORMATION: /note= "This position is U superscript T = 5-(2-Thienyl)-2'-Deoxyuridine."

( i x ) FEATURE:
   ( A ) NAME/KEY: misc_difference
   ( B ) LOCATION: replace(14, "")
   ( D ) OTHER INFORMATION: /note= "This position is U superscript T = 5-(2-Thienyl)-2'-Deoxyuridine."

( i x ) FEATURE:
   ( A ) NAME/KEY: misc_difference
   ( B ) LOCATION: replace(15, "")
   ( D ) OTHER INFORMATION: /note= "This position is U superscript T = 5-(2-Thienyl)-2'-Deoxyuridine."

( x i ) SEQUENCE DESCRIPTION: SEQ ID NO:35:

TNTNTNTNTN NNNNN   15

( 2 ) INFORMATION FOR SEQ ID NO:36:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i x ) FEATURE:
      ( A ) NAME/KEY: misc_difference
      ( B ) LOCATION: replace(2, "")
      ( D ) OTHER INFORMATION: /note= "This position is C'= 5-methyl-2'-deoxycytidine."

( i x ) FEATURE:
      ( A ) NAME/KEY: misc_difference
      ( B ) LOCATION: replace(4, "")
      ( D ) OTHER INFORMATION: /note= "This position is C'= 5-methyl-2'-deoxycytidine."

( i x ) FEATURE:
      ( A ) NAME/KEY: misc_difference
      ( B ) LOCATION: replace(6, "")
      ( D ) OTHER INFORMATION: /note= "This position is C'= 5-methyl-2'-deoxycytidine."

( i x ) FEATURE:
      ( A ) NAME/KEY: misc_difference
      ( B ) LOCATION: replace(7, "")
      ( D ) OTHER INFORMATION: /note= "This position is U superscript T = 5-(2-Thienyl)-2'-Deoxyuridine."

( i x ) FEATURE:
      ( A ) NAME/KEY: misc_difference
      ( B ) LOCATION: replace(8, "")
      ( D ) OTHER INFORMATION: /note= "This position is C'= 5-methyl-2'-deoxycytidine."

( i x ) FEATURE:
      ( A ) NAME/KEY: misc_difference
      ( B ) LOCATION: replace(9, "")
      ( D ) OTHER INFORMATION: /note= "This position is U superscript T = 5-(2-Thienyl)-2'-Deoxyuridine."

(ix) FEATURE:
- (A) NAME/KEY: misc_difference
- (B) LOCATION: replace(10, "")
- (D) OTHER INFORMATION: /note= "This position is C'= 5-methyl-2'-deoxycytidine."

(ix) FEATURE:
- (A) NAME/KEY: misc_difference
- (B) LOCATION: replace(11, "")
- (D) OTHER INFORMATION: /note= "This position is U superscript T = 5-(2-Thienyl)-2'-Deoxyuridine."

(ix) FEATURE:
- (A) NAME/KEY: misc_difference
- (B) LOCATION: replace(13, "")
- (D) OTHER INFORMATION: /note= "This position is U superscript T = 5-(2-Thienyl)-2'-Deoxyuridine."

(ix) FEATURE:
- (A) NAME/KEY: misc_difference
- (B) LOCATION: replace(15, "")
- (D) OTHER INFORMATION: /note= "This position is U superscript T = 5-(2-Thienyl)-2'-Deoxyuridine."

(xi) SEQUENCE DESCRIPTION: SEQ ID NO:36:

TNTNTNNNNN NTNTN        15

(2) INFORMATION FOR SEQ ID NO:37:

(i) SEQUENCE CHARACTERISTICS:
- (A) LENGTH: 15 base pairs
- (B) TYPE: nucleic acid
- (C) STRANDEDNESS: single
- (D) TOPOLOGY: linear (ix) FEATURE:
- (A) NAME/KEY: misc_difference
- (B) LOCATION: replace(1, "")
- (D) OTHER INFORMATION: /note= "This position is U* = 5-(1- propynyl)-2'-deoxyuridine."

(ix) FEATURE:
- (A) NAME/KEY: misc_difference
- (B) LOCATION: replace(2, "")
- (D) OTHER INFORMATION: /note= "This position is C#= Carbocyclic 5-Methyl-2'Deoxycytidine."

(ix) FEATURE:
- (A) NAME/KEY: misc_difference
- (B) LOCATION: replace(3, "")
- (D) OTHER INFORMATION: /note= "This position is U* = 5-(1- propynyl)-2'-deoxyuridine."

(ix) FEATURE:
- (A) NAME/KEY: misc_difference
- (B) LOCATION: replace(4, "")
- (D) OTHER INFORMATION: /note= "This position is C#= Carbocyclic 5-Methyl-2'Deoxycytidine."

(ix) FEATURE:
- (A) NAME/KEY: misc_difference
- (B) LOCATION: replace(5, "")
- (D) OTHER INFORMATION: /note= "This position is U* = 5-(1- propynyl)-2'-deoxyuridine."

(ix) FEATURE:
- (A) NAME/KEY: misc_difference
- (B) LOCATION: replace(6, "")
- (D) OTHER INFORMATION: /note= "This position is C#= Carbocyclic 5-Methyl-2'Deoxycytidine."

(ix) FEATURE:
- (A) NAME/KEY: misc_difference
- (B) LOCATION: replace(7, "")
- (D) OTHER INFORMATION: /note= "This position is U* = 5-(1- propynyl)-2'-deoxyuridine."

(ix) FEATURE:

(A) NAME/KEY: misc_difference
                    (B) LOCATION: replace(8, "")
                    (D) OTHER INFORMATION: /note= "This position is C#=
                        Carbocyclic 5-Methyl-2'Deoxycytidine."

(ix) FEATURE:
                    (A) NAME/KEY: misc_difference
                    (B) LOCATION: replace(9, "")
                    (D) OTHER INFORMATION: /note= "This position is U* =
                        5-(1- propynyl)-2'-deoxyuridine."

(ix) FEATURE:
                    (A) NAME/KEY: misc_difference
                    (B) LOCATION: replace(10, "")
                    (D) OTHER INFORMATION: /note= "This position is C#=
                        Carbocyclic 5-Methyl-2'-Deoxycytidine."

(ix) FEATURE:
                    (A) NAME/KEY: misc_difference
                    (B) LOCATION: replace(11, "")
                    (D) OTHER INFORMATION: /note= "This position is U* =
                        5-(1- propynyl)-2'-deoxyuridine"

(ix) FEATURE:
                    (A) NAME/KEY: misc_difference
                    (B) LOCATION: replace(12, "")
                    (D) OTHER INFORMATION: /note= "This position is U* =
                        5-(1- propynyl)-2'-deoxyuridine."

(ix) FEATURE:
                    (A) NAME/KEY: misc_difference
                    (B) LOCATION: replace(13, "")
                    (D) OTHER INFORMATION: /note= "This position is U* =
                        5-(1- propynyl)-2'-deoxyuridine."

(ix) FEATURE:
                    (A) NAME/KEY: misc_difference
                    (B) LOCATION: replace(14, "")
                    (D) OTHER INFORMATION: /note= "This position is U* =
                        5-(1- propynyl)-2'-deoxyuridine."

(ix) FEATURE:
                    (A) NAME/KEY: misc_difference
                    (B) LOCATION: replace(15, "")
                    (D) OTHER INFORMATION: /note= "This position is U* =
                        5-(1- propynyl)-2'-deoxyuridine."

(xi) SEQUENCE DESCRIPTION: SEQ ID NO:37:

NNNNNNNNN NNNNN                                                                                         15

(2) INFORMATION FOR SEQ ID NO:38:

(i) SEQUENCE CHARACTERISTICS:
                    (A) LENGTH: 17 base pairs
                    (B) TYPE: nucleic acid
                    (C) STRANDEDNESS: single
                    (D) TOPOLOGY: linear (ix) FEATURE:
                    (A) NAME/KEY: misc_difference
                    (B) LOCATION: replace(4, "")
                    (D) OTHER INFORMATION: /note= "This position is 8-Oxo-N
                        superscript 6-Methyl-2'-Deoxyadenosine."

(ix) FEATURE:
                    (A) NAME/KEY: misc_difference
                    (B) LOCATION: replace(8, "")
                    (D) OTHER INFORMATION: /note= "This position is 8-Oxo-N
                        superscript 6-Methyl-2'-Deoxyadenosine."

(ix) FEATURE:
                    (A) NAME/KEY: misc_difference
                    (B) LOCATION: replace(9, "")
                    (D) OTHER INFORMATION: /note= "This position is 8-Oxo-N
                        superscript 6-Methyl-2'-Deoxyadenosine."

(ix) FEATURE:
                    (A) NAME/KEY: misc_difference (B) LOCATION: replace(11, "")
(D) OTHER INFORMATION: /note= "This position is 8-Oxo-N superscript 6-Methyl-2'-Deoxyadenosine."

(ix) FEATURE:
(A) NAME/KEY: misc_difference
(B) LOCATION: replace(12, "")
(D) OTHER INFORMATION: /note= "This position is 8-Oxo-N superscript 6-Methyl-2'Deoxyadenosine."

(xi) SEQUENCE DESCRIPTION: SEQ ID NO:38:

TTTNTTTNNT NNTTTTT 17

(2) INFORMATION FOR SEQ ID NO:39:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(1, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(2, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(3, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(4, "")
(D) OTHER INFORMATION: /note= "This position is M = 8-Oxo-N superscript 6-Methyl-2'-Deoxyadenosine."

(ix) FEATURE:
(A) NAME/KEY: misc_difference
(B) LOCATION: replace(5, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(6, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(7, "")
(D) OTHER INFORMATION: /note= "This position is U* = 5-(1- propynyl)-2'-deoxyuridine."

(ix) FEATURE:
(A) NAME/KEY: misc_difference
(B) LOCATION: replace(8, "")
(D) OTHER INFORMATION: /note= "This position is M = 8-Oxo-N superscript 6-Methyl-2'-Deoxyadenosine."

(ix) FEATURE:
(A) NAME/KEY: misc_difference
(B) LOCATION: replace(9, "")
(D) OTHER INFORMATION: /note= "This position is M = 8-Oxo-N superscript 6-Methyl-2'-Deoxyadenosine."

(ix) FEATURE:
(A) NAME/KEY: misc_difference
(B) LOCATION: replace(10, "")

(D) OTHER INFORMATION: /note= "This position is U* = 5-(1- propynyl)-2'-deoxyuridine."

(ix) FEATURE:
 (A) NAME/KEY: misc_difference
 (B) LOCATION: replace(11, "")
 (D) OTHER INFORMATION: /note= "This position is M = 8-Oxo-N superscript 6-Methyl-2'-Deoxyadenosine."

(ix) FEATURE:
 (A) NAME/KEY: misc_difference
 (B) LOCATION: replace(12, "")
 (D) OTHER INFORMATION: /note= "This position is M = 8-Oxo-N superscript 6-Methyl-2'-Deoxyadenosine."

(ix) FEATURE:
 (A) NAME/KEY: misc_difference
 (B) LOCATION: replace(13, "")
 (D) OTHER INFORMATION: /note= "This position is U* = 5-(1- propynyl)-2'-deoxyuridine."

(ix) FEATURE:
 (A) NAME/KEY: misc_difference
 (B) LOCATION: replace(14, "")
 (D) OTHER INFORMATION: /note= "This position is U* = 5-(1- propynyl)-2'-deoxyuridine."

(ix) FEATURE:
 (A) NAME/KEY: misc_difference
 (B) LOCATION: replace(15, "")
 (D) OTHER INFORMATION: /note= "This position is U* = 5-(1- propynyl)-2'-deoxyuridine."

(ix) FEATURE:
 (A) NAME/KEY: misc_difference
 (B) LOCATION: replace(16, "")
 (D) OTHER INFORMATION: /note= "This position is U* = 5-(1- propynyl)-2'-deoxyuridine."

(ix) FEATURE:
 (A) NAME/KEY: misc_difference
 (B) LOCATION: replace(17, "")
 (D) OTHER INFORMATION: /note= "This position is U* = 5-(1- propynyl)-2'-deoxyuridine."

(xi) SEQUENCE DESCRIPTION: SEQ ID NO:39:

NNNNNNNNN NNNNNN  17

(2) INFORMATION FOR SEQ ID NO:40:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO:40:

TCTCTCTCTC TTTTT  15

(2) INFORMATION FOR SEQ ID NO:41:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:41:

AAAGAAAGGA GGAAAAA  17

(2) INFORMATION FOR SEQ ID NO:42:

(i) SEQUENCE CHARACTERISTICS:
  (A) LENGTH: 17 base pairs

-continued (B) TYPE: nucleic acid
            (C) STRANDEDNESS: single
            (D) TOPOLOGY: linear (x i) SEQUENCE DESCRIPTION: SEQ ID NO:42:

TTTCTTTCCT CCTTTT                                                                    17

(2) INFORMATION FOR SEQ ID NO:43:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (i x) FEATURE:
            (A) NAME/KEY: modified_base
            (B) LOCATION: 2
            (D) OTHER INFORMATION: /note= "This position is C'=
                5-methyl-2'-deoxycytidine."

(i x) FEATURE:
            (A) NAME/KEY: modified_base
            (B) LOCATION: 4
            (D) OTHER INFORMATION: /note= "This position is C'=
                5-methyl-2'-deoxycytidine."

(i x) FEATURE:
            (A) NAME/KEY: modified_base
            (B) LOCATION: 6
            (D) OTHER INFORMATION: /note= "This position is C'=
                5-methyl-2'-deoxycytidine."

(i x) FEATURE:
            (A) NAME/KEY: modified_base
            (B) LOCATION: 8
            (D) OTHER INFORMATION: /note= "This position is C'=
                5-methyl-2'-deoxycytidine."

(i x) FEATURE:
            (A) NAME/KEY: modified_base
            (B) LOCATION: 10
            (D) OTHER INFORMATION: /note= "This position is C'=
                5-methyl-2'-deoxycytidine."

(i x) FEATURE:
            (A) NAME/KEY: misc_difference
            (B) LOCATION: replace(11, "")
            (D) OTHER INFORMATION: /note= "This position is
                5-Methyl-2'-O-allyluridine."

(i x) FEATURE:
            (A) NAME/KEY: misc_difference
            (B) LOCATION: replace(12, "")
            (D) OTHER INFORMATION: /note= "This position is T'=
                5-Methyl-2'-O-allyluridine."

(i x) FEATURE:
            (A) NAME/KEY: misc_difference
            (B) LOCATION: replace(13, "")
            (D) OTHER INFORMATION: /note= "This position is T'=
                5'-Methyl- 2'-O-allyluridine."

(i x) FEATURE:
            (A) NAME/KEY: misc_difference
            (B) LOCATION: replace(14, "")
            (D) OTHER INFORMATION: /note= "This position is T'=
                5-Methyl-2'-O-allylcytidine."

(i x) FEATURE:
            (A) NAME/KEY: misc_difference
            (B) LOCATION: replace(15, "")
            (D) OTHER INFORMATION: /note= "This position is T'=
                5-Methyl-2'-O-allyluridine."

(x i) SEQUENCE DESCRIPTION: SEQ ID NO:43:

TNTNTNTNTN TTTTT                                                                     15

( 2 ) INFORMATION FOR SEQ ID NO:44:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 2
        ( D ) OTHER INFORMATION: /note= "This position is C'= 5-methyl-2'-deoxycytidine."

( i x ) FEATURE:
        ( A ) NAME/KEY: modified_base
        ( B ) LOCATION: 4
        ( D ) OTHER INFORMATION: /note= "This position is C'= 5-methyl-2'-deoxycytidine."

( i x ) FEATURE:
        ( A ) NAME/KEY: modified_base
        ( B ) LOCATION: 6
        ( D ) OTHER INFORMATION: /note= "This position is C'= 5-methyl-2'-deoxycytidine."

( i x ) FEATURE:
        ( A ) NAME/KEY: modified_base
        ( B ) LOCATION: 8
        ( D ) OTHER INFORMATION: /note= "This position is C'= 5-methyl-2'-deoxycytidine."

( i x ) FEATURE:
        ( A ) NAME/KEY: modified_base
        ( B ) LOCATION: 10
        ( D ) OTHER INFORMATION: /note= "This position is C'= 5-methyl-2'-deoxycytidine."

( i x ) FEATURE:
        ( A ) NAME/KEY: misc_difference
        ( B ) LOCATION: replace(11, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(12, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(13, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(14, "")
        ( D ) OTHER INFORMATION: /note= "This position is U* = 5-(1- propynyl)-2'-deoxyuridine."

( i x ) FEATURE:
        ( A ) NAME/KEY: misc_difference
        ( B ) LOCATION: replace(15, "")
        ( D ) OTHER INFORMATION: /note= "This position is U* = 5-(1- propynyl)-2'-deoxyuridine."

( x i ) SEQUENCE DESCRIPTION: SEQ ID NO:44:

TNTNTNTNTN TTTTT        15

( 2 ) INFORMATION FOR SEQ ID NO:45:

( i ) SEQUENCE CHARACTERISTICS:
        ( A ) LENGTH: 15 base pairs
        ( B ) TYPE: nucleic acid ( C ) STRANDEDNESS: single
( D ) TOPOLOGY: linear ( i x ) FEATURE:
    ( A ) NAME/KEY: modified_base
    ( B ) LOCATION: 2
    ( D ) OTHER INFORMATION: /note= "This position is C'=
        5-methyl-2'-deoxycytidine."

( i x ) FEATURE:
    ( A ) NAME/KEY: modified_base
    ( B ) LOCATION: 4
    ( D ) OTHER INFORMATION: /note= "This position is C'=
        5-methyl-2'-deoxycytidine."

( i x ) FEATURE:
    ( A ) NAME/KEY: modified_base
    ( B ) LOCATION: 6
    ( D ) OTHER INFORMATION: /note= "This position is C'=
        5-methyl-2'-deoxycytidine."

( i x ) FEATURE:
    ( A ) NAME/KEY: modified_base
    ( B ) LOCATION: 8
    ( D ) OTHER INFORMATION: /note= "This position is C'=
        5-methyl-2'-deoxycytidine."

( i x ) FEATURE:
    ( A ) NAME/KEY: modified_base
    ( B ) LOCATION: 10
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(11, "")
    ( D ) OTHER INFORMATION: /note= "This position is U
        superscript X = 5-(1-Propynyl)-2'-O-Allyluridine."

( i x ) FEATURE:
    ( A ) NAME/KEY: misc_difference
    ( B ) LOCATION: replace(12, "")
    ( D ) OTHER INFORMATION: /note= "This position is U
        superscript X = 5-(1-Propynyl)-2'-O-Allyluridine."

( i x ) FEATURE:
    ( A ) NAME/KEY: misc_difference
    ( B ) LOCATION: replace(13, "")
    ( D ) OTHER INFORMATION: /note= "This position is U
        superscript X = 5-(1-Propynyl)-2'-O-Allyluridine."

( i x ) FEATURE:
    ( A ) NAME/KEY: misc_difference
    ( B ) LOCATION: replace(14, "")
    ( D ) OTHER INFORMATION: /note= "This position is U
        superscript X = 5-(1-Propynyl)-2'-O-Allyluridine."

( i x ) FEATURE:
    ( A ) NAME/KEY: misc_difference
    ( B ) LOCATION: replace(15, "")
    ( D ) OTHER INFORMATION: /note= "This position is U
        superscript X = 5-(1-Propynyl)-2'-O-Allyluridine."

( x i ) SEQUENCE DESCRIPTION: SEQ ID NO:45:

T N T N T N T N T N    T T T T T                                                  1 5

( 2 ) INFORMATION FOR SEQ ID NO:46:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 2
        ( D ) OTHER INFORMATION: /note= "This position is C''=

5-methyl-2'-O-allylcytidine."

( i x ) FEATURE:
    ( A ) NAME/KEY: modified_base
    ( B ) LOCATION: 4
    ( D ) OTHER INFORMATION: /note= "This position is C''=
        5-methyl-2'-O-allylcytidine."

( i x ) FEATURE:
    ( A ) NAME/KEY: modified_base
    ( B ) LOCATION: 6
    ( D ) OTHER INFORMATION: /note= "This position is C''=
        5-methyl-2'-O-allylcytidine."

( i x ) FEATURE:
    ( A ) NAME/KEY: modified_base
    ( B ) LOCATION: 8
    ( D ) OTHER INFORMATION: /note= "This position is C''=
        5-methyl-2'-O-allylcytidine."

( i x ) FEATURE:
    ( A ) NAME/KEY: modified_base
    ( B ) LOCATION: 10
    ( D ) OTHER INFORMATION: /note= "This position is C''=
        5-methyl-2'-O-allylcytidine."

( x i ) SEQUENCE DESCRIPTION: SEQ ID NO:46:

TNTNTNTNTN TTTTT        15

( 2 ) INFORMATION FOR SEQ ID NO:47:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
    ( A ) NAME/KEY: modified_base
    ( B ) LOCATION: 2
    ( D ) OTHER INFORMATION: /note= "This position is C* =
        5-(1- propynyl)-2'-deoxycytidine."

( i x ) FEATURE:
    ( A ) NAME/KEY: modified_base
    ( B ) LOCATION: 4
    ( D ) OTHER INFORMATION: /note= "This position is C* =
        5-(1- propynyl)-2'-deoxycytidine."

( i x ) FEATURE:
    ( A ) NAME/KEY: modified_base
    ( B ) LOCATION: 6
    ( D ) OTHER INFORMATION: /note= "This position is C* =
        5-(1- propynyl)-2'-deoxycytidine."

( i x ) FEATURE:
    ( A ) NAME/KEY: modified_base
    ( B ) LOCATION: 8
    ( D ) OTHER INFORMATION: /note= "This position is C* =
        5-(1- propynyl)-2'-deoxycytidine."

( i x ) FEATURE:
    ( A ) NAME/KEY: modified_base
    ( B ) LOCATION: 10
    ( D ) OTHER INFORMATION: /note= "This position is C* =
        5-(1- propynyl)-2'-deoxycytidine."

( x i ) SEQUENCE DESCRIPTION: SEQ ID NO:47:

TNTNTNTNTN TTTTT        15

( 2 ) INFORMATION FOR SEQ ID NO:48:

( i ) SEQUENCE CHARACTERISTICS:
        ( A ) LENGTH: 15 base pairs
        ( B ) TYPE: nucleic acid
        ( C ) STRANDEDNESS: single (D) TOPOLOGY: linear (ix) FEATURE:
    (A) NAME/KEY: modified_base
    (B) LOCATION: 2
    (D) OTHER INFORMATION: /note= "This position is C superscript X = 5-(1-Propynyl)-2'-O-Allylcytidine."

(ix) FEATURE:
    (A) NAME/KEY: modified_base
    (B) LOCATION: 4
    (D) OTHER INFORMATION: /note= "This position is C superscript X = 5-(1-Propynyl)-2'-O-Allylcytidine."

(ix) FEATURE:
    (A) NAME/KEY: modified_base
    (B) LOCATION: 6
    (D) OTHER INFORMATION: /note= "This position is C superscript X = 5-(1-Propynyl)-2'-O-Allylcytidine."

(ix) FEATURE:
    (A) NAME/KEY: modified_base
    (B) LOCATION: 8
    (D) OTHER INFORMATION: /note= "This position is C superscript X = 5-(1-Propynyl)-2'-O-Allylcytidine."

(ix) FEATURE:
    (A) NAME/KEY: modified_base
    (B) LOCATION: 10
    (D) OTHER INFORMATION: /note= "This position is C superscript X = 5-(1-Propynyl)-2'-O-Allylcytidine."

(xi) SEQUENCE DESCRIPTION: SEQ ID NO:48:

TNTNTNTNTN TTTTT 15

(2) INFORMATION FOR SEQ ID NO:49:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:49:

AAAAAGAGAG AGAGA 15

(2) INFORMATION FOR SEQ ID NO:50:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(1, "")
        (D) OTHER INFORMATION: /note= "This position is U* = 5-(1- propynyl)-2'-deoxyuridine."

(ix) FEATURE:
        (A) NAME/KEY: misc_difference
        (B) LOCATION: replace(2, "")
        (D) OTHER INFORMATION: /note= "This position is C'= 5-methyl-2'-deoxycytidine."

(ix) FEATURE:
        (A) NAME/KEY: misc_difference
        (B) LOCATION: replace(3, "")
        (D) OTHER INFORMATION: /note= "This position is U* = 5-(1- propynyl)-2'-deoxyuridine."

(ix) FEATURE:
        (A) NAME/KEY: misc_difference
        (B) LOCATION: replace(4, "")
        (D) OTHER INFORMATION: /note= "This position is C'=

-continued 5-methyl-2'-deoxycytidine."

( i x ) FEATURE:
    ( A ) NAME/KEY: misc_difference
    ( B ) LOCATION: replace(5, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(6, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(7, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(8, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(9, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(10, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(11, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(12, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(13, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(14, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(15, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(16, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(17, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(18, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(19, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(20, "")
    ( D ) OTHER INFORMATION: /note= "This position is C'=
        5-methyl-2'-deoxycytidine."

( i x ) FEATURE:
    ( A ) NAME/KEY: misc_difference
    ( B ) LOCATION: replace(21, "")
    ( D ) OTHER INFORMATION: /note= "This position is X* =
        switchback linker synthon."

( i x ) FEATURE:
    ( A ) NAME/KEY: misc_difference
    ( B ) LOCATION: replace(22, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(23, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(24, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(25, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(26, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(27, "")
    ( D ) OTHER INFORMATION: /note= "This position is U* =
        5-(1- propynyl)-2'-deoxyuridine."

( i x ) FEATURE:
    ( A ) NAME/KEY: misc_difference
    ( B ) LOCATION: replace(28, "")
    ( D ) OTHER INFORMATION: /note= "This position is U* =
        5-(1- propynyl)-2'-deoxyuridine."

( x i ) SEQUENCE DESCRIPTION: SEQ ID NO:50:

NNNNNNNNN NNNNNNNNN NNNNNNN    28

( 2 ) INFORMATION FOR SEQ ID NO:51:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i x ) FEATURE:

- continued ( A ) NAME/KEY: misc_difference
    ( B ) LOCATION: replace(1, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(2, "")
    ( D ) OTHER INFORMATION: /note= "This position is C'= 5-methyl-2'-deoxycytidine."

( i x ) FEATURE:
    ( A ) NAME/KEY: misc_difference
    ( B ) LOCATION: replace(3, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(4, "")
    ( D ) OTHER INFORMATION: /note= "This position is C'= 5-methyl-2'-deoxycytidine."

( i x ) FEATURE:
    ( A ) NAME/KEY: misc_difference
    ( B ) LOCATION: replace(5, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(6, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(7, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(8, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(9, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(10, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(11, "")
    ( D ) OTHER INFORMATION: /note= "This position is C'= 5-methyl-2'-deoxycytidine."

( i x ) FEATURE:
    ( A ) NAME/KEY: misc_difference
    ( B ) LOCATION: replace(12, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(13, "")
    ( D ) OTHER INFORMATION: /note= "This position is U* = 5-(1- propynyl)-2'-deoxyuridine."

( i x ) FEATURE:
    ( A ) NAME/KEY: misc_difference
    ( B ) LOCATION: replace(14, "")

(D) OTHER INFORMATION: /note= "This position is C'=
5-methyl-2'-deoxycytidine."

(ix) FEATURE:
(A) NAME/KEY: misc_difference
(B) LOCATION: replace(15, "")
(D) OTHER INFORMATION: /note= "This position is U* =
5-(1- propynyl)-2'-deoxyuridine."

(ix) FEATURE:
(A) NAME/KEY: misc_difference
(B) LOCATION: replace(16, "")
(D) OTHER INFORMATION: /note= "This position is C'=
5-methyl-2'-deoxycytosine."

(ix) FEATURE:
(A) NAME/KEY: misc_difference
(B) LOCATION: replace(17, "")
(D) OTHER INFORMATION: /note= "This position is U* =
5-(1- propynyl)-2'-deoxyuridine."

(ix) FEATURE:
(A) NAME/KEY: misc_difference
(B) LOCATION: replace(18, "")
(D) OTHER INFORMATION: /note= "This position is U* =
5-(1- propynyl)-2'-deoxyuridine."

(ix) FEATURE:
(A) NAME/KEY: misc_difference
(B) LOCATION: replace(19, "")
(D) OTHER INFORMATION: /note= "This position is U* =
5-(1- propynyl)-2'-deoxyuridine."

(ix) FEATURE:
(A) NAME/KEY: misc_difference
(B) LOCATION: replace(20, "")
(D) OTHER INFORMATION: /note= "This position is C'=
5-methyl-2'-deoxycytidine."

(ix) FEATURE:
(A) NAME/KEY: misc_difference
(B) LOCATION: replace(21, "")
(D) OTHER INFORMATION: /note= "This position is X* =
switchback linker synthon."

(ix) FEATURE:
(A) NAME/KEY: misc_difference
(B) LOCATION: replace(22, "")
(D) OTHER INFORMATION: /note= "This position is U* =
5-(1- propynyl)-2'-deoxyuridine."

(ix) FEATURE:
(A) NAME/KEY: misc_difference
(B) LOCATION: replace(23, "")
(D) OTHER INFORMATION: /note= "This position is U* =
5-(1- propynyl)-2'-deoxyuridine."

(xi) SEQUENCE DESCRIPTION: SEQ ID NO:51:

NNNNNNNNN NNNNNNNNN NNN    23

(2) INFORMATION FOR SEQ ID NO:52:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:52:

AGAGAAGGGA GAAGAGAAAG AAATTTTTTT TT    32

(2) INFORMATION FOR SEQ ID NO:53:

(i) SEQUENCE CHARACTERISTICS:
(A) LENGTH: 32 base pairs
(B) TYPE: nucleic acid ( C ) STRANDEDNESS: single
( D ) TOPOLOGY: linear ( x i ) SEQUENCE DESCRIPTION: SEQ ID NO:53:

TCTCTTTTT CTTCTCTTTC TTTAAAAAAA AA                                    32